(12) United States Patent
Xiong et al.

(10) Patent No.: US 11,306,125 B2
(45) Date of Patent: Apr. 19, 2022

(54) PCSK9 ANTAGONISTS BICYCLO-COMPOUNDS

(71) Applicant: Merck Sharp & Dohme Corp., Rahway, NJ (US)

(72) Inventors: Yusheng Xiong, Plainsboro, NJ (US); Thomas Joseph Tucker, North Wales, PA (US); Chengwei Wu, Ambler, PA (US); Elisabetta Bianchi, Rome (IT); Danila Branca, Pomezia (IT); Angela Dawn Kerekes, Plainfield, NJ (US); Abbas M. Walji, Lansdale, PA (US); Hubert B. Josien, Jersey City, NJ (US); Fa-Xiang Ding, Staten Island, NJ (US); Hyewon Youm, Berkeley Heights, NJ (US); Alessia Santoprete, Rome (IT); Raffaele Ingenito, Pomezia (IT)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 17/253,815

(22) PCT Filed: Jun. 20, 2019

(86) PCT No.: PCT/US2019/038158
§ 371 (c)(1),
(2) Date: Dec. 18, 2020

(87) PCT Pub. No.: WO2019/246352
PCT Pub. Date: Dec. 26, 2019

(65) Prior Publication Data
US 2021/0214395 A1    Jul. 15, 2021

Related U.S. Application Data

(60) Provisional application No. 62/688,020, filed on Jun. 21, 2018.

(51) Int. Cl.
*C07K 7/56* (2006.01)
*A61K 38/00* (2006.01)

(52) U.S. Cl.
CPC ............... *C07K 7/56* (2013.01); *A61K 38/00* (2013.01)

(58) Field of Classification Search
CPC .. C07K 7/56; A61K 38/00; A61P 3/06; C07D 487/18; C07D 498/22
See application file for complete search history.

(56) References Cited

U.S. PATENT DOCUMENTS

| 4,393,046 A | 7/1983 | Baylis et al. |
| 2010/0041102 A1 | 2/2010 | Sitlani et al. |
| 2012/0219558 A1 | 8/2012 | Ni et al. |
| 2013/0158021 A1 | 6/2013 | Dong et al. |
| 2013/0281366 A1 | 10/2013 | Pingali et al. |
| 2017/0081383 A1 | 3/2017 | Gruber |
| 2017/0189470 A1 | 7/2017 | Wang et al. |
| 2018/0023071 A1 | 1/2018 | Basak |

FOREIGN PATENT DOCUMENTS

| WO | WO 2010/144038 A1 | 12/2010 |
| WO | WO 2012/040259 A2 | 3/2012 |
| WO | WO 2017/181061 A1 | 10/2017 |
| WO | WO 2017/220701 A1 | 12/2017 |
| WO | WO 2018/053517 A1 | 3/2018 |

(Continued)

OTHER PUBLICATIONS

Josephson et al, Drug Discovery Today, vol. 19, No. 4, Apr. 2014, 388-399 (Year: 2014).*

(Continued)

*Primary Examiner* — Sudhakar Katakam
(74) *Attorney, Agent, or Firm* — Lathrop GPM LLP; Brian C. Trinque

(57) ABSTRACT

Disclosed are compounds of Formula I, or a salt thereof cyclic polypeptide of Formula I: Formula I where A, B, E, $R^4$, and $R^8$ are as defined herein, which compounds have properties for antagonizing PCSK9. Also described are pharmaceutical formulations comprising the compounds of Formula I or their salts, and methods of treating cardiovascular disease and conditions related to PCSK9 activity, e.g. atherosclerosis, hypercholesterolemia, coronary heart disease, metabolic syndrome, acute coronary syndrome, or related cardiovascular disease and cardiometabolic conditions (I)

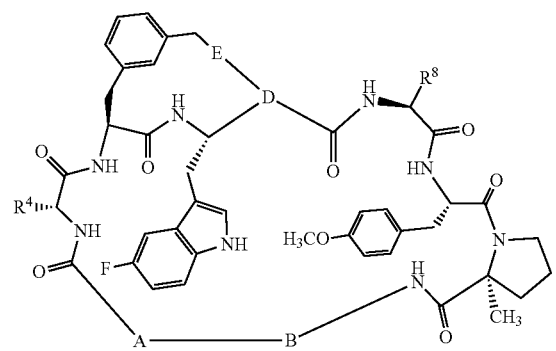

15 Claims, No Drawings

(56) References Cited

FOREIGN PATENT DOCUMENTS

| WO | WO 2019/246349 A1 | 12/2019 |
|---|---|---|
| WO | WO 2019/246352 A1 | 12/2019 |
| WO | WO 2019/246386 A1 | 12/2019 |
| WO | WO 2019/246387 A1 | 12/2019 |
| WO | WO 2019/246405 A1 | 12/2019 |
| WO | WO 2020/009805 A3 | 1/2020 |

OTHER PUBLICATIONS

Zhang et al, Nature structure & molecular biology, vol. 24, No. 10, Oct. 2017, 848-856 (Year: 2017).*
Zhang et al, The Journal of Biological Chemistry, vol. 289, No. 2, Jan. 10, 2014, 942-955 (Year: 2014).*
PCT/US2019/038220 WO 2019/246386, Jun. 20, 2019 Dec. 26, 2019, Alonso Ricardo.
PCT/US2019/038221 WO 2019/246387, Jun. 20, 2019 Dec. 26, 2019, Alonso Ricardo.
U.S. Appl. No. 17/253,783 2021/0163538, filed Dec. 18, 2020 Jun. 3, 2021, Alonso Ricardo.
PCT/US2019/038247 WO 2020/009805, Jun. 20, 2019 Apr. 2, 2019, Alonso Ricardo.
U.S. Appl. No. 17/253,864 2021/0284694, filed Dec. 18, 2020 Sep. 16, 2021, Alonso Ricardo.
PCT/US2019/038250 WO 2019/246405, Jun. 20, 2019 Dec. 26, 2019, Alonso Ricardo.
U.S. Appl. No. 16/446,940 2019/0389909, filed Jun. 20, 2019 Dec. 26, 2019, Harold B. Wood.
PCT/US2019/038155 WO 2019/246349, Jun. 20, 2019 Dec. 26, 2019, Harold B. Wood.
PCT/US2019/038158 WO 2019/246352, Jun. 20, 2019 Dec. 26, 2019, Yusheng Xiong.
U.S. Appl. No. 17/005,686 2021/0069288, filed Aug. 28, 2020 Mar. 11, 2021, Hubert Josien.
PCT/US2020/048342 WO 2021/041770, Aug. 28, 2020 Apr. 3, 2021, Hubert Josien.
PCT/US2020/066046 WO 2021/127460, Dec. 18, 2020 Jun. 24, 2021, Hubert Josien.

Chaudhary et al., "PCSK9 inhibitors: A new era of lipid lowering therapy", World Journal of Cardiology, Feb. 26, 2017, vol. 9, No. 2, pp. 76-91.
Elbitar et al., "Proprotein convertase subtilisin/kexin 9 (PCSK9) inhibitors and the future of dyslipidemia therapy: an updated patent review (2011-2015)", Expert Opinion on Therapeutic Patents, 2016, 26(12): 1377-1392.
He et al. "Lowering serum lipids via PcSK9-targeting drugs: current advances and future perspectives", ACTA Pharmacologica Sinica, Jan. 23, 2017, vol. 38, pp. 301-311.
International Search Report and Written Opinion in related PCT Application No. PCT/US2020/048342, dated Nov. 18, 2020, 11 pages.
International Search Report and Written Opinion in related PCT Application No. PCT/US2019/038220, dated Nov. 5, 2019, 11 pages.
International Search Report and Written Opinion in related PCT Application No. PCT/US2019/038155, dated Nov. 15, 2019, 6 pages.
International Search Report and Written Opinion in related PCT Application No. PCT/US2019/038221, dated Nov. 18, 2019, 12 pages.
International Search Report and Written Opinion in related PCT Application No. PCT/US2019/038247, dated Apr. 20, 2020, 13 pages.
International Search Report and Written Opinion in related PCT Application No. PCT/US2019/038250, dated Sep. 17, 2019, 7 pages.
International Search Report and Written Opinion in related PCT Application No. PCT/US2019/038158, dated Dec. 26, 2019, 7 pages.
Umemura et al., Characterization of the biosynthetic gene cluster for the ribosomally synthesized cyclic peptide ustiloxin B in *Aspergillus flavus*, Fungal Genetics and Biology, 2014, vol. 68, pp. 23-30.
Zhang et al., "Identification of a Small Peptide That Inhibits PCSK9 Protein Binding to the Low Density Lipoprotein Receptor", The Journal of Biological Chemistry, Jan. 10, 2014, vol. 289, No. 2, pp. 942-955.
International Search Report and Written Opinion in related PCT Application No. PCT/US2020/066046, dated Mar. 2, 2021, 3 pages.

\* cited by examiner

PCSK9 ANTAGONISTS BICYCLO-COMPOUNDS

CROSS REFERENCE TO RELATED APPLICATION

This application is a 35 U.S.C. § 371 filing of International Patent Application No. PCT/US2019/038158, filed Jun. 20, 2019, which claims priority to U.S. Application No. 62/688,020, filed Jun. 21, 2018, which is incorporated herein by reference in its entirety.

BACKGROUND OF THE INVENTION

The identification of compounds and/or agents that are effective in the treatment of cardiovascular affliction is highly desirable. In clinical trials, reductions in LDL cholesterol levels have been directly related to the rate of coronary events; Law et al., 2003 *BMJ* 326:1423-1427. The moderate lifelong reduction in plasma LDL cholesterol levels was found to correlate with a substantial reduction in the incidence of coronary events; Cohen et al., 2006 *N. Engl. J. Med.* 354:1264-1272. This was the case even in populations with a high prevalence of non-lipid-related cardiovascular risk factors; supra. Accordingly, there is great benefit to be reaped from the managed control of LDL cholesterol levels.

Proprotein convertase subtilisin-kexin type 9 (hereinafter called "PCSK9"), also known as neural apoptosis-regulated convertase 1 ("NARC-1"), is a proteinase K-like subtilase identified as the $9^{th}$ member of the secretory subtilase family; see Seidah et al., 2003 *PNAS* 100:928-933. PCSK9 belongs to the mammalian proprotein convertase family of serine proteases and contains an N-terminal signal sequence, a prodomain, a catalytic domain, and a C-terminal domain; see Seidah et al., 2012 *Nat. Rev. Drug Discov.* 11:367-383. A study of PCSK9 transcriptional regulation demonstrated that it is regulated by sterol regulatory element-binding proteins ("SREBP"), as seen with other genes involved in cholesterol metabolism; Maxwell et al., 2003 *J. Lipid Res.* 44:2109-2119, as is typical of other genes implicated in lipoprotein metabolism; Dubuc et al., 2004 *Arterioscler. Thromb. Vasc. Biol.* 24:1454-1459. Statins have been shown to upregulate PCSK9 expression in a manner attributed to the cholesterol-lowering effects of the drugs; supra. Moreover, it has been shown that PCSK9 promoters possess two conserved sites involved in cholesterol regulation, a sterol regulatory element and an Sp1 site; supra.

While in the endoplasmic reticulum, PCSK9 performs as its only catalytic activity an autocleavage between residues Gln-152 and Ser-153; see Naureckiene et al., 2003 *Arch. Biochem. Biophys.* 420:55-67; Seidah et al., 2003 *Proc. Natl Acad. Sci. U.S.A* 100:928-933. The prodomain remains tightly associated with the catalytic domain during subsequent trafficking through the trans-Gogli network. The maturation via autocleavage has been demonstrated to be critical for PCSK9 secretion and subsequent extracellular function (see Benjannet et al., 2012 *J. Biol. Chem.* 287:33745-33755). Accordingly, several lines of evidence demonstrate that PCSK9, in particular, lowers the amount of hepatic LDLR protein and thus compromises the liver's ability to remove LDL cholesterol from the circulation.

Adenovirus-mediated overexpression of PCSK9 in the liver of mice results in the accumulation of circulating LDL-C due to a dramatic loss of hepatic LDLR protein, with no effect on LDLR mRNA levels; Benjannet et al., 2004 *J. Biol. Chem.* 279:48865-48875; Maxwell & Breslow, 2004 *PNAS* 101:7100-7105; Park etai, 2004 *J. Biol. Chem.* 279: 50630-50638; and Lalanne etai, 2005 *J. Lipid Res.* 46:1312-1319. The effect of PCSK9 overexpression on raising circulating LDL-C levels in mice is completely dependent on the expression of LDLR, again, indicating that the regulation of LDL-C by PCSK9 is mediated through downregulation of LDLR protein. In agreement with these findings, mice lacking PCSK9 or in which PCSK9 mRNA has been lowered by antisense oligonucleotide inhibitors have higher levels of hepatic LDLR protein and a greater ability to clear circulating LDL-C; Rashid etai, 2005 *PNAS* 102:5374-5379; and Graham etai, 2007 *J. Lipid Res.* 48(4):763-767. In addition, lowering PCSK9 levels in cultured human hepatocytes by siRNA also results in higher LDLR protein levels and an increased ability to take up LDL-C; Benjannet et al., 2004 *J. Biol Chem.* 279:48865-48875; and Lalanne et al., 2005 *J. Lipid Res.* 46:1312-1319. Together, these data indicate that PCSK9 action leads to increased LDL-C by lowering LDLR protein levels.

A number of mutations in the gene PCSK9 have also been conclusively associated with autosomal dominant hypercholesterolemia ("ADH"), an inherited metabolism disorder characterized by marked elevations of low density lipoprotein ("LDL") particles in the plasma which can lead to premature cardiovascular failure; see Abifadel et al., 2003 *Nature Genetics* 34:154-156; Timms et al, 2004 *Hum. Genet.* 114:349-353; Leren, 2004 *Clin. Genet.* 65:419-422. A later-published study on the S127R mutation of Abifadel et al., supra, reported that patients carrying such a mutation exhibited higher total cholesterol and apoB100 in the plasma attributed to (1) an overproduction of apoB100-containing lipoproteins, such as low density lipoprotein ("LDL"), very low density lipoprotein ("VLDL") and intermediate density lipoprotein ("IDL"), and (2) an associated reduction in clearance or conversion of said lipoproteins; Ouguerram et al., 2004 Arterioscler. Thromb. Vasc. Biol. 24:1448-1453.

Accordingly, there can be no doubt that PCSK9 plays a role in the regulation of LDL. The expression or upregulation of PCSK9 is associated with increased plasma levels of LDL cholesterol, and the corresponding inhibition or lack of expression of PCSK9 is associated with reduced LDL cholesterol plasma levels. Decreased levels of LDL cholesterol associated with sequence variations in PCSK9 have been found to confer protection against coronary heart disease; Cohen, 2006 *N. Eng. J. Med.* 354:1264-1272.

Thus, identification of compounds and/or agents effective in the treatment of cardiovascular affliction is highly desirable, including antagonism of PCSK9's role in LDL regulation, however, in general, because PCSK9 circulates in blood and has modest binding affinity to cell surface LDL receptors here-to-fore attempts to utilize this mechanism in treatment of diseases related to high serum LDL levels have been focused on the use of large biomolecules, for example, antibodies. Accordingly, there is scant publication reflecting activity toward this target using small peptides or small molecules to inhibit PCSK9, see for example, Zhang et al., 2014 J. Biol. Chemistry, 289(2): 942-955. Moreover, there is a paucity of compounds which are amenable to formulation into a dosage form for utilizing an oral administration route of dosing such compounds, a route which would be highly desirable for the provision of therapy for conditions in which regulation of the activities of PCSK9 could play a role.

The present invention advances these interests by providing antagonists of PCSK9 which are believed to be of use for inhibiting the activities of PCSK9 and the corresponding role PCSK9 plays in various conditions for which the administration of a PCSK9 antagonist provides therapy.

SUMMARY OF THE INVENTION

In one aspect the invention provides a compound of Formula I:

Formula I

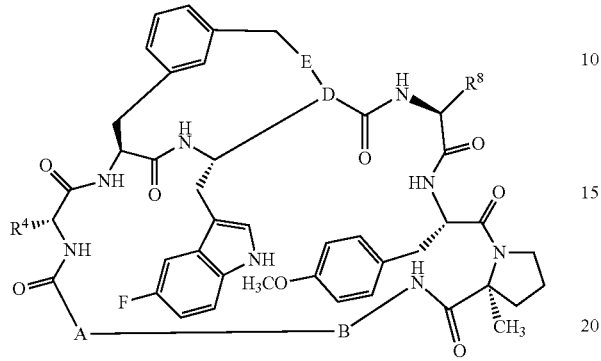

wherein:

R$^4$ is:
- (a) linear, branched or cyclic alkyl of up to 6 carbon atoms, and in some embodiments is preferably —CH$_3$ or —CH(CH$_3$)$_2$
- (b) —(CH$_2$)$_x$—R$^{13B}$, wherein: x is 1-4, and R$^{13B}$ is —NH$_2$ or —N$^+$H$_3$; (c) —(CH$_2$)$_x$—R$^{13C}$, wherein: x is 1-4, and R$^{13C}$ is —N(R$^{13D}$)$_2$ or —N$^+$(R$^{13D}$)$_3$ wherein R$^{13D}$ is a linear or branched alkyl of up to 4 carbon atoms, and in some embodiments is preferably —CH$_3$;
- (d) —CH$_2$NH—C(O)—O—C(CH$_3$)$_3$; or
- (e) —CH$_2$—NH—C(O)—[(CH$_2$)$_2$—O—]$_y$—(CH$_2$)$_2$—R$^{13E}$, wherein: y is 1 to 6, and in some embodiments is preferably 2, and R$^{13E}$ is —NH$_2$, —N$^+$H$_3$, or —N$^+$(CH$_3$)$_3$;

R$^8$ is a moiety of the formula:

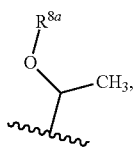

wherein R$^{8a}$ is —H, or a linear, branched or cyclic alkyl of up to four carbon atoms, and in some embodiments is preferably —CH$_3$, or —C(CH$_3$)$_3$;

A is (a) —CH$_2$—; or
(b) a moiety of the formula:

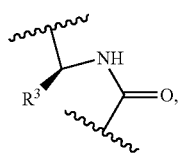

wherein R$^3$ is:
- (i) linear, branched or cyclic alkyl of up to 6 carbon atoms, and in some embodiments is preferably —CH$_3$ or —CH(CH$_3$)$_2$;
- (ii) —(CH$_2$)$_z$—R$^{14A}$, wherein: z is 1-4, and R$^{14A}$ is —NH$_2$ or —N$^+$H$_3$;
- (iii) —(CH$_2$)$_z$—R$^{14B}$, wherein: z is 1-4, and R$^{14B}$ is —N(CH$_3$)$_2$ or —N$^+$(CH$_3$)$_3$; or
- (iv) —CH$_2$—NH—C(O)—[(CH$_2$)$_2$—O—]$_{y'}$—(CH$_2$)$_2$—R$^{14C}$, wherein, y' is 1 to 6, and in some embodiments is preferably 2, and R$^{14C}$ is —NH$_2$, —N$^+$H$_3$, or —N$^+$(CH$_3$)$_3$;

B is:
(a) a moiety of the formula:

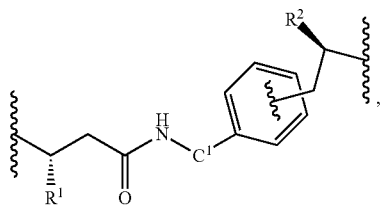

wherein:

R$^1$ is —H or —NH—C(O)—CH$_3$;

R$^2$ is —H or —C(O)—R$^{15A}$, wherein R$^{15A}$ is —NH$_2$, —N$^+$H$_3$, or —N$^+$(CH$_3$)$_3$; and C$^1$ is —CH$_2$— or —(CH$_2$)$_2$—O—; or (b) a moiety of the formula:

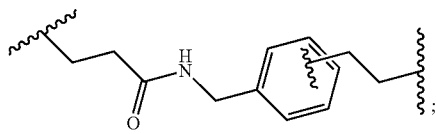

D is:
(a) a moiety of the formula:

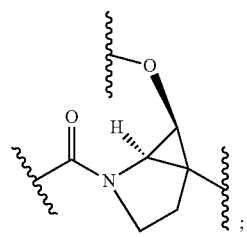 [SMILES: *O[C@@H]1[C@@H]2N(C(*)=O)CCC12*]

(b) a moiety of the formula:

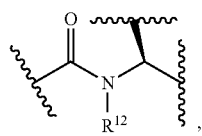

wherein R$^{12}$ is —H or —CH$_3$; and

E is:
(a) a moiety of the formula:
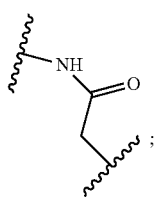 [SMILES: *CC(=O)N*]
(b) a moiety of the formula:
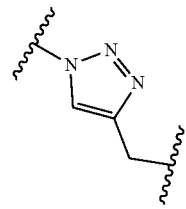 [SMILES: *Cc1cn(*)nn1]
or a pharmaceutically acceptable salt thereof.
In one aspect the present invention is a compound of the formula:
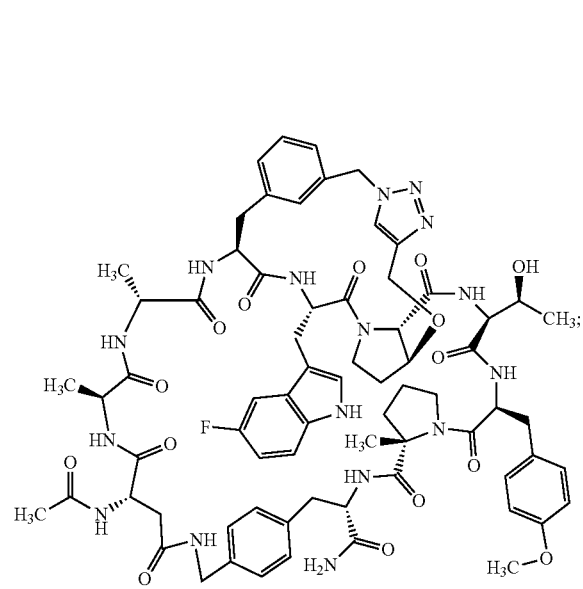
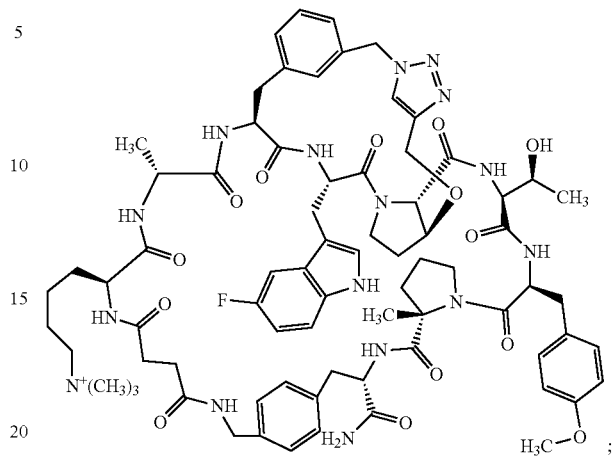
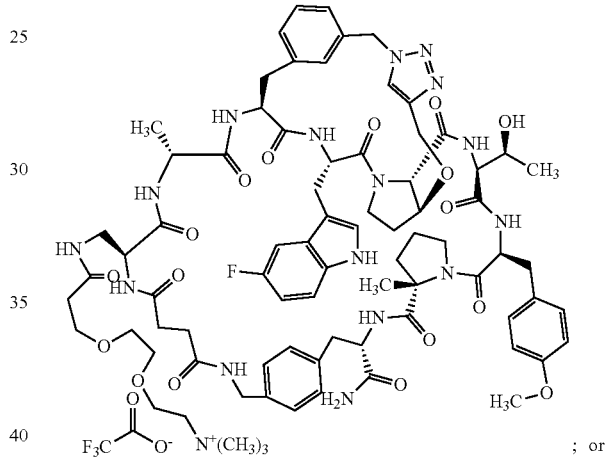
or a pharmaceutically acceptable salt thereof.
In one aspect the present invention is a compound of the formula:
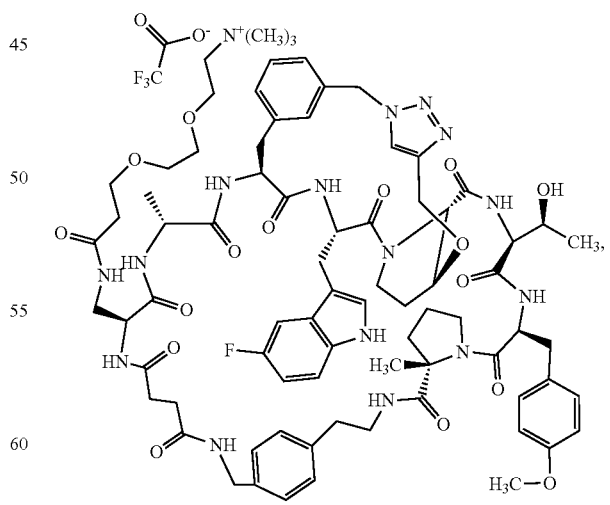

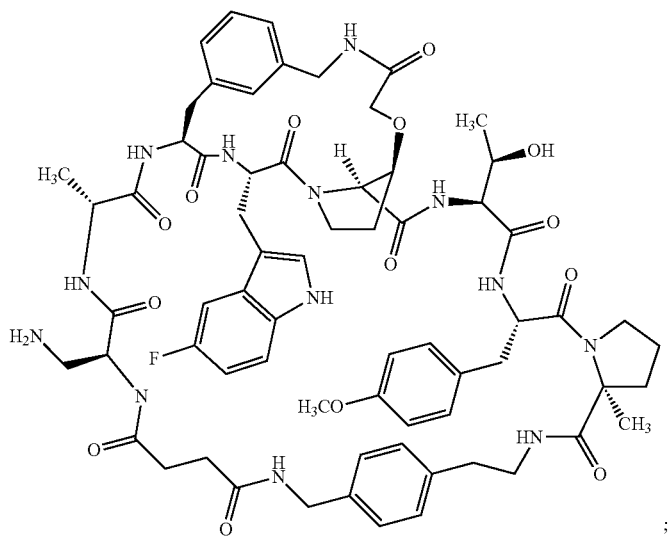
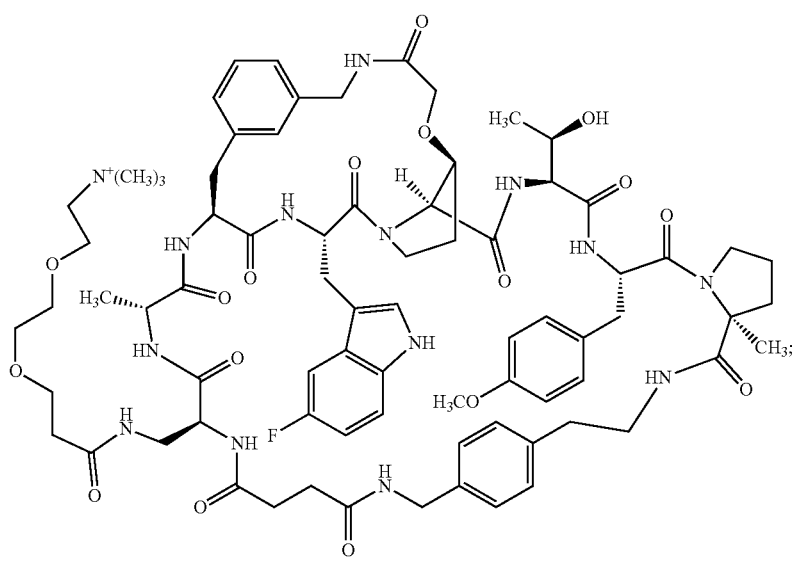
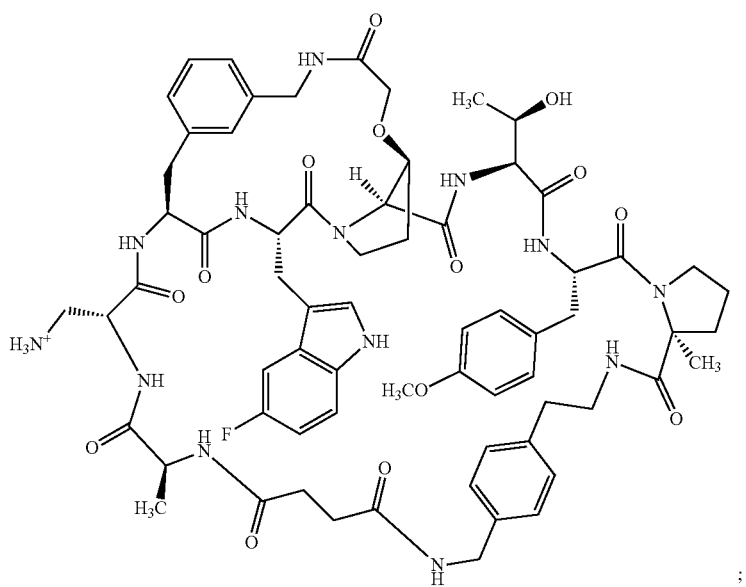

-continued
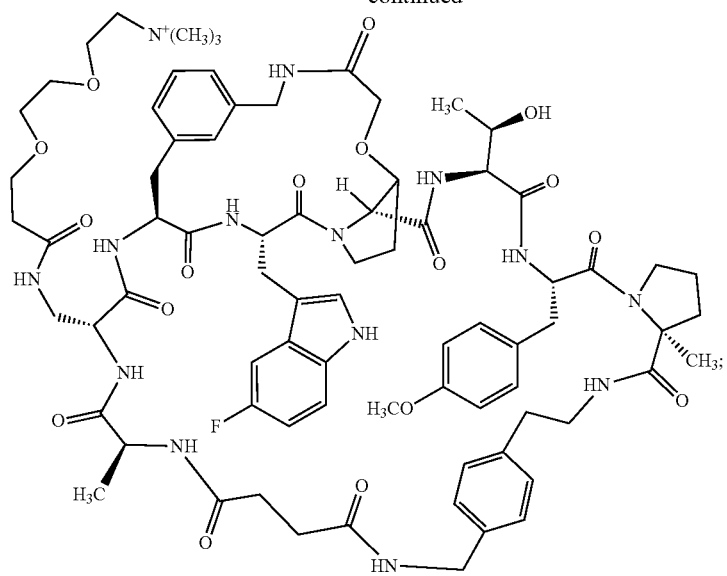
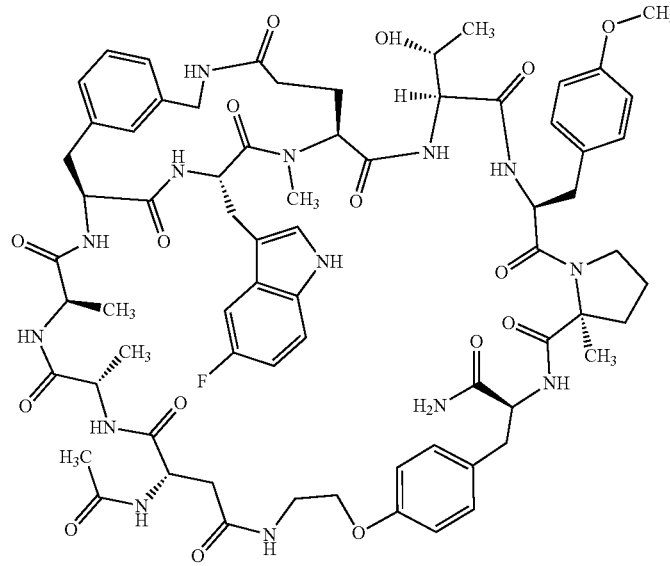
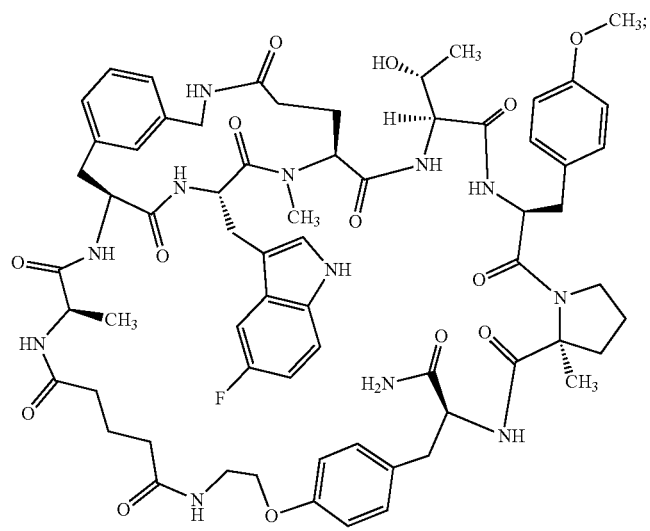

-continued
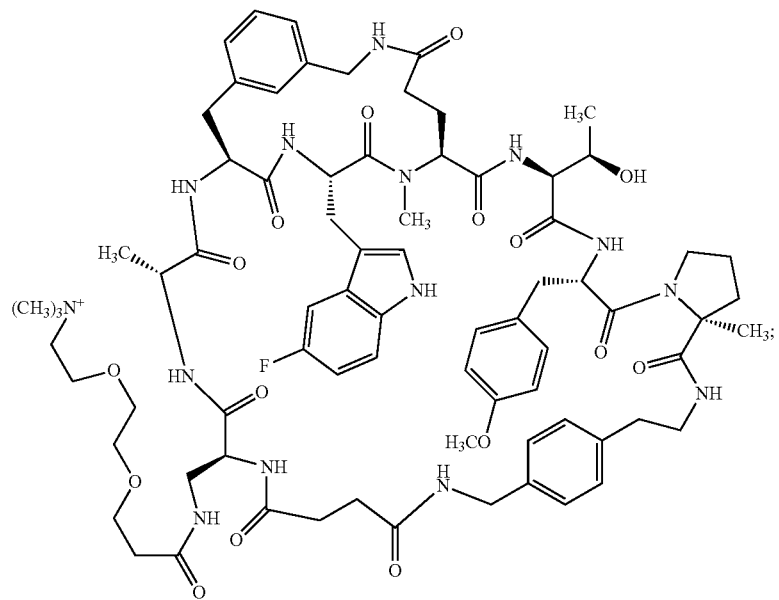
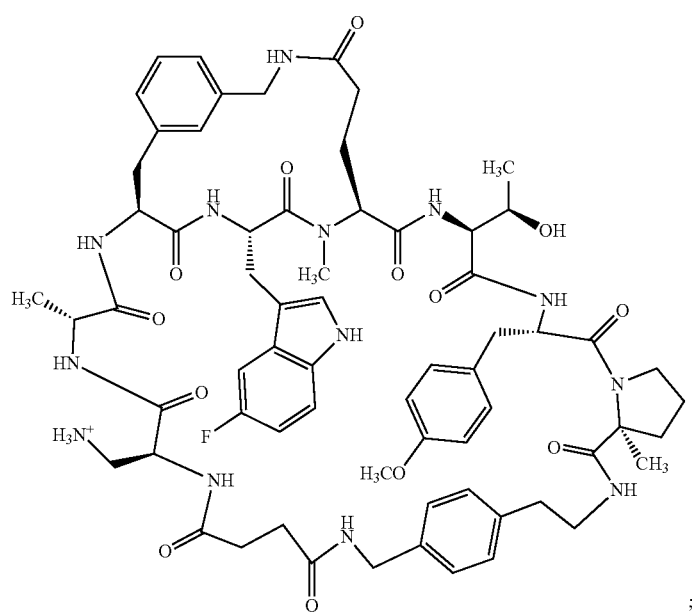

-continued
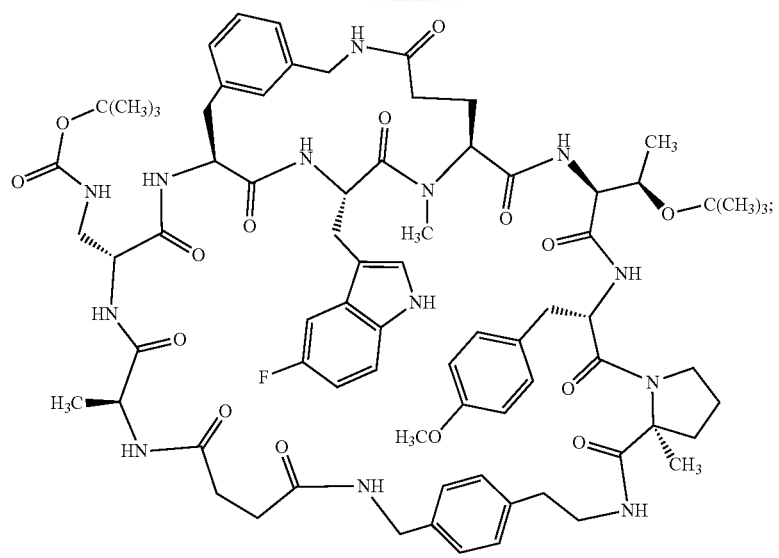
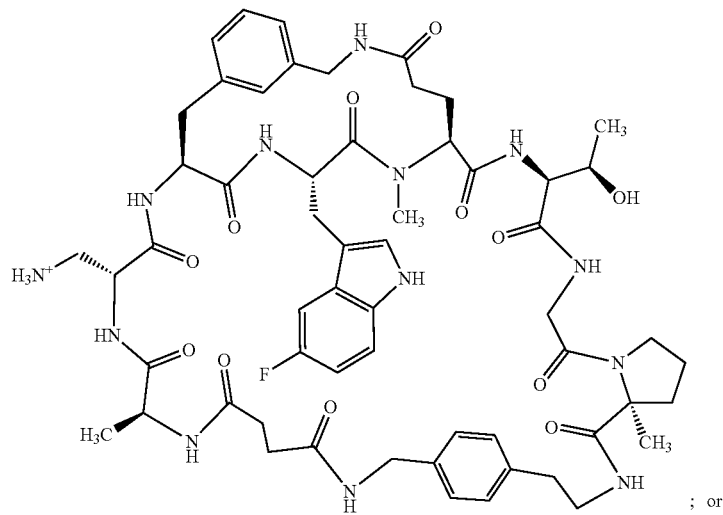
; or
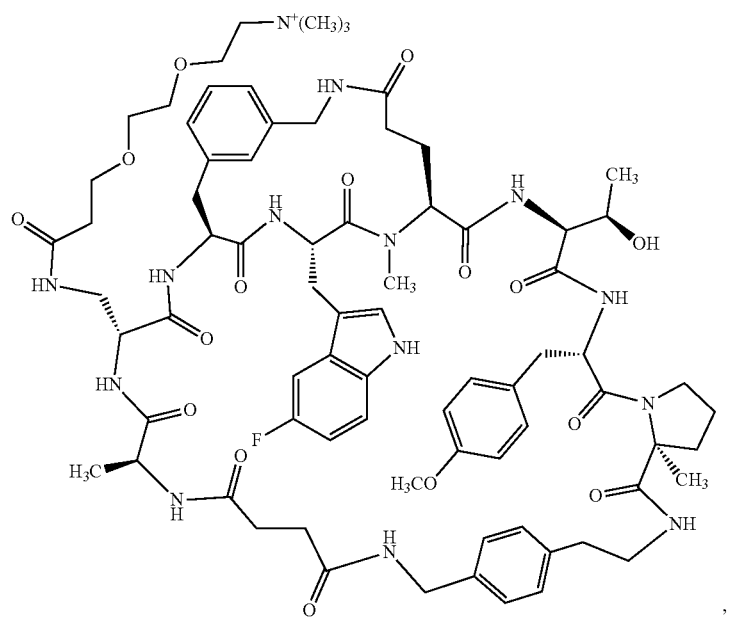
, or a pharmaceutically acceptable salt thereof.

In one embodiment the present invention provides pharmaceutical compositions comprising a compound of the invention, for example, a compound of Formula I, and at least one pharmaceutical excipient, preferably a composition directed to oral administration.

In one aspect the present invention provides a method of antagonizing PCSK9 in the provision of therapy for disease states related to PCSK9 activity, for example, atherosclerosis, hypercholesterolemia, coronary heart disease, metabolic syndrome, acute coronary syndrome, or related cardiovascular disease and cardiometabolic conditions, by administering to a subject in need thereof a therapeutically effective amount of a compound of Formula I, or a salt thereof, preferably in the form of a pharmaceutical composition.

DETAILED-DESCRIPTION OF THE INVENTION

In the description that follows conventional structural representation is employed and includes conventional stereochemical notation for certain asymmetric carbon centers.

Thus, structural representation of compounds of the invention includes conventional stereochemical notation for some asymmetric carbon centers shown in the example compounds. Accordingly, in such instances, solid black "wedge" bonds represent bonds projecting from the plane of the reproduction medium, "hashed wedge" bonds representing descending bonds into the plane of the reproduction medium, and a "wavy" line appended to a carbon bearing a double bond indicates both possible cis and trans orientations are included. As is conventional, plain solid lines represent all spatial configurations for the depicted bonding. Accordingly, where no specific stereochemical notation is supplied the representation contemplates all stereochemical and spatial orientations of the structural features.

As is shown in the examples of the invention, and mentioned above, particular asymmetric carbon centers are structurally represented using conventional "Solid Wedge" and "Hash Wedge" bonding representation. For the most part, absolute configuration has not been determined for the example compounds, but has been assigned by analogy to specific example compounds which were prepared using the same or analogous reaction conditions and starting reagents of known stereochemical configurations, were isolated under the same chromatographic conditions, and for which absolute stereochemistry was determined by X-ray crystallography. Accordingly, specific assignment of the configurations structurally represented herein is meant to identify the specific compounds prepared and is not put forth as being the product of absolute structural determination unless otherwise noted in the data presented.

It will be appreciated that were isomeric mixtures are obtained, the preparation of individual stereoisomers in significant percentages of enantiomeric excess can be carried out, if desired, by separation of a mixture by customary methods, for example by chromatography or crystallization, by the use of stereochemically uniform starting materials for the synthesis or by stereoselective synthesis. Optionally a derivatization can be carried out before a separation of stereoisomers. The separation of a mixture of stereoisomers can be carried out at an intermediate step during the synthesis of a compound of Formula I or it can be done on a final racemic product.

Where indicated herein, absolute stereochemistry is determined by X-ray crystallography of crystalline products or crystalline intermediates which are derivatized, if necessary, with a reagent containing a stereogenic center of known configuration. Unless a particular isomer, salt, solvate (including hydrates) or solvated salt of such racemate, enantiomer, or diastereomer is indicated, the present invention includes all such isomers, as well as salts, solvates (including hydrates) and solvated salts of such racemates, enantiomers, diastereomers and mixtures thereof.

The present invention also embraces isotopically-labeled compounds of the present invention which are structurally identical to those recited herein, but for the fact that a statistically significant percentage of one or more atoms in that form of the compound are replaced by an atom having an atomic mass or mass number different from the atomic mass or mass number of the most abundant isotope usually found in nature, thus altering the naturally occurring abundance of that isotope present in a compound of the invention. The present invention is meant to include all suitable isotopic variations of the compounds of Formula I.

Examples of isotopes that can be preferentially incorporated into compounds of the invention include isotopes of hydrogen, carbon, nitrogen, oxygen, phosphorus, iodine, fluorine and chlorine, for example, but not limited to: $^{2}H$, $^{3}H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, and $^{36}Cl$, $^{123}I$ and $^{125}I$. It will be appreciated that other isotopes may be incorporated by known means also.

In particular, certain isotopically-labeled compounds of the invention (e.g., those labeled with $^{3}H$, $^{11}C$ and $^{14}C$) are recognized as being particularly useful in compound and/or substrate tissue distribution assays using a variety of known techniques. Additionally, compounds of the invention contemplate isotopic substitution include different isotopic forms of hydrogen (H), including protium ($^{1}H$) and deuterium ($^{2}H$ or D). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within Formula I can be prepared without undue experimentation by conventional techniques well known to those skilled in the art or by processes analogous to those described in the Schemes and Examples herein using appropriate isotopically-enriched reagents and/or intermediates.

In describing the compounds of the invention the term "linear-alkyl" or "branched-alkyl" means saturated carbon chains which may be linear or branched or combinations thereof, unless the carbon chain is defined otherwise. Examples of linear alkyl or branched alkyl groups include methyl, ethyl, propyl, isopropyl, butyl, sec- and tert-butyl, pentyl, hexyl, heptyl, octyl, nonyl, and the like. The term "Cycloalkyl" means a saturated monocyclic, bicyclic or bridged carbocyclic ring, having a specified number of carbon atoms. Examples of cycloalkyl include cyclopropyl, cyclobutyl, cyclopentyl, cyclohexyl, cycloheptyl and the like. Where an alkyl moiety is specified by the number of carbon atoms, for example, " . . . a linear, branched, or cyclic alkyl of up to four carbon atoms" means all 4 carbon alkyl moieties, and includes methyl, ethyl, propyl, isopropyl, n-butyl, secondary-butyl, iso-butyl, tertiarybutyl, cyclo propyl, methyl-cyclopropyl-, -methylene-cyclopropyl and cyclobutyl.

Where a wavy line terminates a conventional bond (as opposed to connecting two atoms within a structure) it indicates a point of bonding to a structure, e.g.:

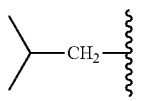

indicates a the secondary-butyl moiety is bonded via the methylene group via the bond terminated with the wavey line. Where an alphabetical notation is used to depict a substituent moiety, a dash is employed to indicate the point of bonding to the indicated substrate, e.g.: —CH$_2$—C(O)—CH$_2$Cl indicates the acetyl chloride moiety is bonded via the methylene portion of the moiety.

When any variable (e.g., n, R$^a$, R$^b$, etc.) occurs more than one time in any constituent or in Formula I, its definition on each occurrence is independent of its definition at every other occurrence unless otherwise specified at the point of definition. One of ordinary skill in the art will recognize that choice of combinations of the various substituents defined in a structural representation, i.e. R$^1$, R$^4$, etc., are to be chosen in conformity with well-known principles of chemical structure connectivity and stability, and combinations of substituents and/or variables are permissible only if such combinations result in stable compounds.

A "stable" compound is a compound which can be prepared and isolated and whose structure and properties remain or can be caused to remain essentially unchanged for a period of time sufficient to allow use of the compound for the purposes described herein (e.g., therapeutic administration to a subject). The compounds of the present invention are limited to stable compounds embraced by Formula I.

Where any variable or moiety is expressed in the form of a range, eg (—CH$_2$—)$_{1-4}$, both of the extrema of the specified range are included (i.e. 1 and 4 in the example) as well as all of the whole number values in between (i.e. 2 and 3 in the example).

The term "Halogen" includes fluorine, chlorine, bromine and iodine unless specified otherwise at the point of use.

As the term is used herein, "subjects" (alternatively "patients") refers to an animal, preferably a mammal, and in particular a human or a non-human animal including livestock animals and domestic animals including, but not limited to, cattle, horses, sheep, swine, goats, rabbits, cats, dogs, and other mammals in need of treatment. In some embodiments the subject is preferably a human. As used herein, the term "administration" and variants thereof (e.g., "administering" a compound) in reference to a compound of Formula I means providing the compound, or a pharmaceutically acceptable salt thereof, to a subject in need of treatment.

As mentioned above, in one aspect the present invention includes the provision of compounds of Formula I, or a pharmaceutically acceptable salt thereof, which have properties that antagonize PCSK9 function.

In some embodiments, it is preferred for the compounds of Formula I to have the structure of Formula II, or a pharmaceutically acceptable salt thereof:

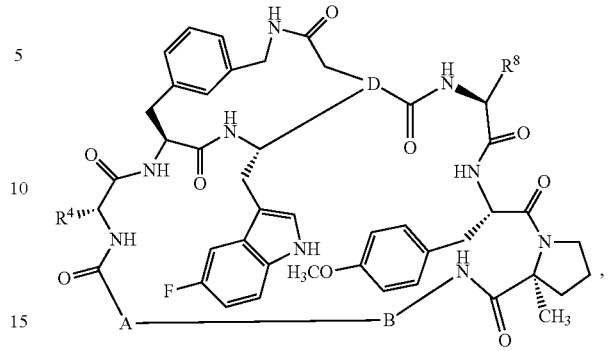

Formula II wherein: A, B, D, R$^4$, and R$^8$ are as defined above.

In some embodiments R$^4$ is preferably: (a) —CH$_3$; (b) —CH(CH$_3$)$_2$; (c) —(CH$_2$)$_x$—R$^{13b}$, wherein: x is 1-4, and R$^{13b}$ is —NH$_2$ or —N$^+$H3; (d) —CH$_2$NH—C(O)—O—C(CH$_3$)$_3$; or (iv) —CH$_2$—NH—C(O)—[(CH$_2$)$_2$—O—]$_2$—(CH$_2$)$_2$—R$^{13c}$, wherein R$^{13c}$ is —NH$_2$, —N$^+$H$_3$, or —N$^+$(CH$_3$)$_3$.

In some embodiments R$^8$ is a moiety of the formula:

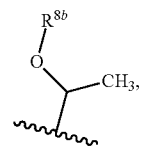

wherein R$^{8b}$ is —H, —CH$_3$, or —C(CH$_3$)$_3$.

In some embodiments wherein A is a moiety of the formula:

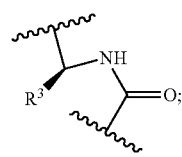

R$^3$ is preferably (i) —CH$_3$; (ii) —CH(CH$_3$)$_2$; (iii) —(CH$_2$)$_z$—R$^{13a}$, wherein: z is 1-4, in some embodiments, preferably 4, and R$^{13a}$ is -NH$_2$, —N$^+$H$_3$ or —N$^+$(CH$_3$)$_3^-$; or (iv) —CH$_2$—NH—C(O)—[(CH$_2$)$_2$—O—]$_2$—(CH$_2$)$_2$—R$^{13c}$, wherein R$^{13c}$ is —NH$_2$, —N$^+$H$_3$, or —N$^+$(CH$_3$)$_3$.

In some embodiments wherein B is a moiety pf the formula

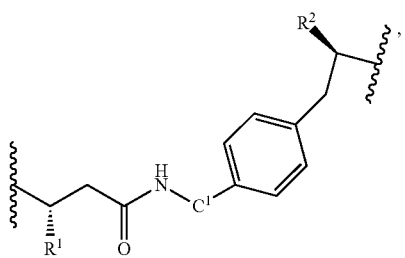

wherein $C^1$ is as defined above, $R^1$ is preferably —H or —NH—C(O)—CH$_3$; and $R^2$ is preferably —H or —C(O)—NH$_2$.

In some embodiments, it is preferred for the compounds of Formula I to have the structure of Formula III, or a pharmaceutically acceptable salt thereof:

Formula III

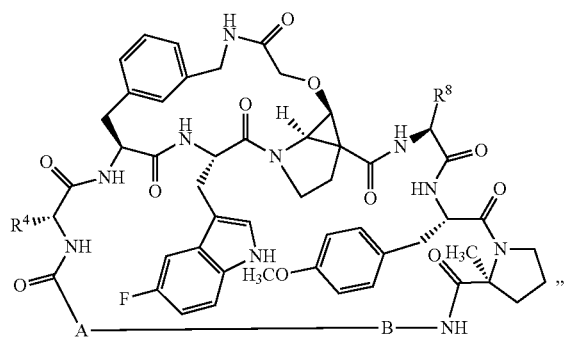

wherein $R^4$, $R^8$, A and B are as defined above, or a pharmaceutically acceptable salt thereof.

In some embodiments, it is preferred for the compounds of Formula I to have the structure of Formula IV, or a pharmaceutically acceptable salt thereof:

Formula IV

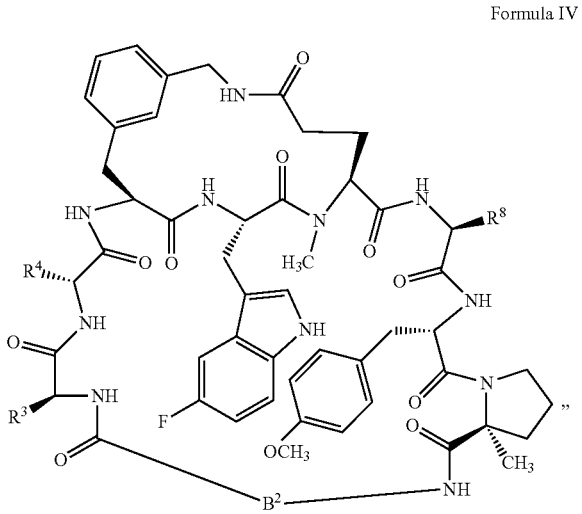

wherein:
$R^3$, $R^4$, and $R^8$, are as defined above; and
$B^2$ is:
(a) a moiety of the formula:

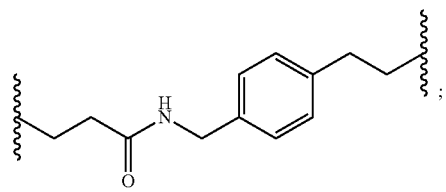 [SMILES: *CCC(=O)NCc1ccc(CC*)cc1]

or (b) a moiety of the formula:

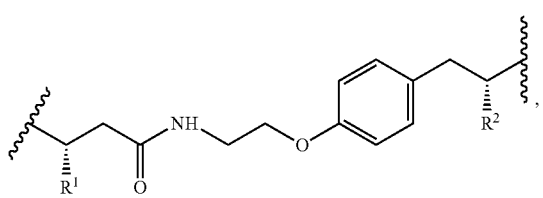

wherein:
$R^1$ is —H or —NH—C(O)—CH$_3$;
$R^2$ is —H or —C(O)—R$^{16A}$ NH$_2$ R$^{16A}$ is —NH$_2$, —N$^+$H$_3$, —N(CH$_3$)$_2$, or —N$^+$(CH$_3$)$_3$,
or a pharmaceutically acceptable salt thereof.

Also provided herein as compounds of Formula I are compounds Ex-B01, Ex-B02, Ex-B03, Ex-B04, Ex-C01, Ex-C02, Ex-C03, Ex-C04, Ex-C05, Ex-C06, Ex-C07, Ex-OT-03, Ex-OT-04, Ex-OT-05, and Ex-OT-06, or any pharmaceutically acceptable salt thereof. These compounds are also referred to herein as "compounds of the invention."

The term "salt(s)", and its use in the phrase "pharmaceutically acceptable salts" employed herein, includes any of the following: acidic salts formed with inorganic and/or organic acids, basic salts formed with inorganic and/or organic bases, zwitterionic and quaternary ammonium complexes. Salts of compounds of the invention may be formed by methods known to those of ordinary skill in the art, for example, by reacting a compound of the invention with an amount of acid or base, such as an equivalent amount, in a medium such as one in which the salt precipitates or in aqueous medium followed by lyophilization.

Compounds of the invention contain tri-coordinate nitrogen atoms, for example, primary, secondary or tertiary amino moieties, wherein the lone pair of electrons residing on the nitrogen atom may be protonated with an appropriate acid or alkylated with an appropriate reagent, for example, alkyl bromide, under the appropriate reaction conditions to provide tetracoordinate charged nitrogen stabilized by an anion generated in the process, for example, a halogen ion or conjugate base. Accordingly, compounds of the invention may be prepared in the form of a free-base or isolated in the form of a quaternary complex or a salt complex. In some instances where there is an appropriate acidic proton proximal to a basic nitrogen formation of a zwitterionic complex is possible. As the term is employed herein, salts of the inventive compounds, whether acidic salts formed with inorganic and/or organic acids, basic salts formed with inorganic and/or organic bases, salts formed which include zwitterionic character, for example, where a compound contains both a basic moiety, for example, but not limited to, a nitrogen atom, for example, an amine, pyridine or imidazole, and an acidic moiety, for example, but not limited to a carboxylic acid, and quaternary ammonium complexes are included in the scope of the inventive compounds described herein.

Accordingly, structural representation of compounds of the invention, whether in a free-base form, a salt form, a zwiterionic form or a quaternary ammonium form, also include all other forms of such compounds discussed above. Thus, one aspect of the invention is the provision of compounds of the invention in the form of a pharmaceutically acceptable salt, zwitterionic complex or quaternary ammonium complex. Those skilled in the art will recognize those instances in which the compounds of the invention may form such complexes, including where a tetracoordinate nitrogen can be quaternized or protonated and the charged nitrogen form stabilized by an associated anion. The term "pharmaceutically acceptable salt" refers to a salt (including a quaternary ammonium complex and an inner salt such as a zwitterion complex) which possesses effectiveness similar to or greater than a free-base form of the compound and which is not biologically or otherwise undesirable (e.g., is neither toxic nor otherwise deleterious to the recipient thereof).

The formation of pharmaceutically useful salts from basic (or acidic) pharmaceutical compounds are discussed, for example, by S. Berge et al., Journal of Pharmaceutical Sciences (1977) 66(1) 1-19; P. Gould, International J. of Pharmaceutics (1986) 33 201-217; Anderson et al, The Practice of Medicinal Chemistry (1996), Academic Press, New York; in The Orange Book (Food & Drug Administration, Washington, D.C. on their website); and P. Heinrich Stahl, Camille G. Wermuth (Eds.), Handbook of Pharmaceutical Salts: Properties, Selection, and Use, (2002) Int'l. Union of Pure and Applied Chemistry, pp. 330-331. These disclosures are incorporated herein by reference.

The present invention contemplates all available salts, including salts which are generally recognized as safe for use in preparing pharmaceutical formulations and those which may be formed presently within the ordinary skill in the art and are later classified as being "generally recognized as safe" for use in the preparation of pharmaceutical formulations, termed herein as "pharmaceutically acceptable salts". Examples of pharmaceutically acceptable acid addition salts include, but are not limited to, acetates, including trifluoroacetate salts, adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, 2-hydroxyethanesulfonates, lactates, maleates, methanesulfonates, methyl sulfates, 2-naphthalenesulfonates, nicotinates, nitrates, oxalates, pamoates, pectinates, persulfates, 3-phenylpropionates, phosphates, picrates, pivalates, propionates, salicylates, succinates, sulfates, sulfonates (such as those mentioned herein), tartarates, thiocyanates, toluenesulfonates (also known as tosylates,) undecanoates, and the like.

Examples of pharmaceutically acceptable basic salts include, but are not limited to, ammonium salts, alkali metal salts such as sodium, lithium, and potassium salts, alkaline earth metal salts such as calcium and magnesium salts, aluminum salts, zinc salts, salts with organic bases (for example, organic amines) such as benzathines, diethylamine, dicyclohexylamines, hydrabamines (formed with N,N-bis(dehydroabietyl)ethylenediamine), N-methyl-D-glucamines, N-methyl-D-glucamides, t-butyl amines, piperazine, phenylcyclohexyl-amine, choline, tromethamine, and salts with amino acids such as arginine, lysine and the like. Basic nitrogen-containing groups may be converted to an ammonium ion or quaternized with agents such as lower alkyl halides (e.g. methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myristyl and stearyl chlorides, bromides and iodides), aralkyl halides (e.g. benzyl and phenethyl bromides), and others.

In general, salts of compounds are intended to be pharmaceutically acceptable salts within the scope of the invention.

The term "purified", "in purified form" or "in isolated and purified form" for a compound refers to the physical state of said compound after being isolated from a synthetic process or natural source or combination thereof. Thus, the term "purified", "in purified form" or "in isolated and purified form" for a compound refers to the physical state of said compound after being obtained from a purification process or processes described herein or well known to the skilled artisan, and in sufficient purity to be characterized by standard analytical techniques described herein or well known to the skilled artisan. Compounds of the invention include any form of the compound including in situ in a reaction mixture as well as in isolated and purified form obtained by routine techniques. Also included are polymorphic forms of the compounds of the invention and solvates and prodrugs thereof.

Certain compounds of the invention may exist in different tautomeric forms, for example, but are not limited to, ketone/enol tautomeric forms, imine-enamine tautomeric forms, and for example heteroaromatic forms such as the following moieties:

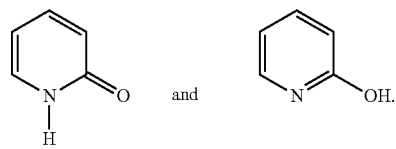 [SMILES: O=c1cccc[nH]1 ; "and" ; Oc1ccccn1]

In the same manner, unless indicated otherwise, presenting a structural representation of any tautomeric form of a compound which exhibits tautomerism is meant to include all such tautomeric forms of the compound. Accordingly, where compounds of the invention, their salts, and solvates and prodrugs thereof, may exist in different tautomeric forms or in equilibrium among such forms, all such forms of the compound are embraced by, and included within the scope of the invention.

In another aspect, the present invention provides pharmaceutical compositions comprising one or more compounds of the invention. As used herein, the term "pharmaceutical composition" comprises at least one pharmaceutically active compound and at least one excipient, and is intended to encompass both the combination of the specified ingredients in the specified amounts, and any product which results, directly or indirectly, from combination of the specified ingredients in the specified amounts.

As will be appreciated by the ordinarily skilled artisan, excipients are any constituent which adapts the composition to a particular route of administration or aids the processing of a composition into a dosage form without itself exerting an active pharmaceutical effect. In general compositions comprise more than one excipient depending upon the route of administration and the characteristics of the active being administered. Examples of excipients which impart to the composition properties which make it easier to handle or process include, but are not limited to, lubricants or pressing aids in powdered medicaments intended to be tableted, and emulsion stabilizers in compositions in which the active is present in the form of an emulsion. Examples of excipients which adapt a composition to a desired route of administration are, for example, but not limited to, for oral administration, absorption enhancers promoting absorption from the gastrointestinal tract, for transdermal ortransmucosal administration, penetration enhancers, for example, those employed in adhesive skin "patch" or compositions for buccal administration.

Notwithstanding the function excipients perform in a composition, excipients are collectively termed herein "a carrier". Typically, formulations may comprise up to about 95 percent active ingredient and the balance carrier, although formulations with different ratios may be prepared. In general, acceptable pharmaceutical compositions contain a suitable concentration of the active that an effective amount of the PCSK9 antagonist can be provided in an individual dosage form of acceptable volume based upon the route of administration such that it can provide a therapeutic serum level of the active for an acceptable period of time in a subject to whom the composition is administered and the composition will retain biological activity during storage within an acceptable temperature range for an acceptable period of time.

Pharmaceutical composition, as used herein, refers both to a bulk composition, that is, formulated material that has not yet been formed into individual dosage units for administration, and the composition contained within individual dosage units.

While compositions of the invention may be employed in bulk form, it will be appreciated that for most applications compositions will be incorporated into a dosage form providing individual units suitable for administration to a patient, each dosage form comprising an amount of the selected composition which contains an effective amount of said one or more compounds of Formula I. Examples of suitable dosage forms include, but are not limited to, dosage forms adapted for: (i) oral administration, e.g., a liquid, gel, powder, solid or semi-solid pharmaceutical composition which is loaded into a capsule or pressed into a tablet and may comprise additionally one or more coatings which modify its release properties, for example, coatings which impart delayed release or formulations which have extended release properties; (ii) a dosage form adapted for administration through tissues of the oral cavity, for example, a rapidly dissolving tablet, a lozenge, a solution, a gel, a sachet or a needle array suitable for providing intramucosal administration; (iii) a dosage form adapted for administration via the mucosa of the nasal or upper respiratory cavity, for example a solution, suspension or emulsion formulation for dispersion in the nose or airway; (iv) a dosage form adapted for transdermal administration, for example, a patch, cream or gel; (v) a dosage form adapted for intradermal administration, for example, a microneedle array; (vi) a dosage form adapted for intravenous (IV) infusion, for example, over a prolonged period using an I.V. infusion pump; (vii) a dosage form adapted for intramuscular administration (IM), for example, an injectable solution or suspension, and which may be adapted to form a depot having extended release properties; (viii) a dosage form adapted for drip intravenous administration (IV), for example, a solution or suspension, for example, as an IV solution or a concentrate to be injected into a saline IV bag; (ix) a dosage form adapted for subcutaneous administration, including administration over an extended time period by implanting a rod or other device which diffuses the compound into the surround tissue and thereby provides a continuous serum therapeutic level; or (x) a dosage form adapted for delivery via rectal or vaginal mucosa, for example, a suppository.

Pharmaceutical compositions can be solid, semi-solid or liquid. Solid, semi-solid and liquid form preparations can be adapted to a variety of modes of administration, examples of which include, but are not limited to, powders, dispersible granules, mini-tablets, beads, which can be used, for example, for tableting, encapsulation, or direct administration. In addition, liquid form preparations include, but are not limited to, solutions, suspensions and emulsions which for example, but not exclusively, can be employed in the preparation of formulations intended for ingestion, inhalation or intravenous administration (IV), for example, but not limited to, administration via drip IV or infusion pump, intramuscular injection (IM), for example, of a bolus which is released over an extended duration, direct IV injection, or adapted to subcutaneous routes of administration.

Other routes of administration which may be contemplated include intranasal administration, or for administration to some other mucosal membrane. Formulations prepared for administration to various mucosal membranes may also include additional components adapting them for such administration, for example, viscosity modifiers.

Although in some embodiments, compositions suitable for use in a solid oral dosage form, for example, a tablet or quick-melt mouth-dissolving formulation are preferable routes of administration for a compound of the invention or a salt thereof, a composition of the invention may be formulated for administration via other routes mentioned above. Examples include aerosol preparations, for example, suitable for administration via inhalation or via nasal mucosa, may include solutions and solids in powder form, which may be in combination with a pharmaceutically acceptable propellant, for example, an inert compressed gas, e.g. nitrogen. Also included are solid form preparations which are intended to be converted, shortly before use, to a suspension or a solution, for example, for oral or parenteral administration. Examples of such solid forms include, but are not limited to, freeze dried formulations and liquid formulations adsorbed into a solid absorbent medium.

For example, the compounds of the invention may also be deliverable transdermally ortransmucosally, for example, from a liquid, suppository, cream, foam, gel, or rapidly dissolving solid form. It will be appreciated that transdermal compositions can take also the form of creams, lotions, aerosols and/or emulsions and can be provided in a unit dosage form which includes a transdermal patch of any know in the art, for example, a patch which incorporates either a matrix comprising the pharmaceutically active compound or a reservoir which comprises a solid or liquid form of the pharmaceutically active compound.

Examples of pharmaceutically acceptable carriers and methods of manufacture for various compositions mentioned above may be found in A. Gennaro (ed.), Remington: The Science and Practice of Pharmacy, 20$^{th}$ Edition, (2000), Lippincott Williams & Wilkins, Baltimore, Md. Additional examples of publications addressing formulation issues may be found in: Pharmaceutical compositions may be formulated by any number of strategies known in the art, see, e.g., McGoff and Scher, 2000 *Solution Formulation of Proteins/Peptides*: In—McNally, E. J., ed. Protein Formulation and Delivery. New York, N.Y.: Marcel Dekker; pp. 139-158; Akers & Defilippis, 2000, *Peptides and Proteins as Parenteral Solutions*. In—Pharmaceutical Formulation Development of Peptides and Proteins. Philadelphia, Pa.: Taylor and Francis; pp. 145-177; Akers et al., 2002, *Pharm. Biotechnol.* 14:47-127.

In another aspect the present invention provides methods of employing PCSK9-specific antagonist compounds described herein for antagonizing PCSK9 function; said methods of which are further described below. Use of the term "antagonizing" throughout the present application refers to providing to the affected tissue(s) a substance which opposes the action of, inhibits, counteracts, neutralizes or curtails one or more functions of PCSK9 in the affected tissues. Inhibition or antagonism of one or more of PCSK9-associated functional properties can be readily determined according to methodologies known to the art (see, e.g., Barak & Webb, 1981 *J. Cell Biol.* 90:595-604; Stephan & Yurachek, 1993 *J. Lipid Res.* 34:325330; and McNamara et al., 2006 *Clinica Chimica Acta* 369:158-167) as well as those described herein. Inhibition or antagonism will effectuate a decrease in PCSK9 activity relative to that seen in the absence of the antagonist or, for example, that seen when a control antagonist of irrelevant specificity is present. Preferably, a PCSK9-specific antagonist in accordance with the present invention antagonizes PCSK9 functioning to the point that there is a decrease of at least 10%, of the measured parameter including but not limited to the activities disclosed herein, and more preferably, a decrease of at least 20%, 30%, 40%, 50%, 60%, 70%, 80%, 90% and 95% of the measured parameter. Such inhibition/antagonism of PCSK9 functioning is particularly effective in those instances where PCSK9 functioning is contributing at least in part to a particular phenotype, disease, disorder or condition which is negatively impacting the subject.

In one aspect, the present invention provides a method for antagonizing the activity of PCSK9, which comprises contacting a cell, population of cells or tissue sample capable of being affected by PCSK9 (i.e., which expresses and/or comprises LDL receptors) with a PCSK9-specific antagonist disclosed herein under conditions that allow said antagonist to bind to PCSK9 when present and inhibit PCSK9's inhibition of cellular LDL uptake. In some embodiments of the present invention include such methods wherein the cell is a human cell. Additional embodiments of the present invention include such methods wherein the cell is a murine cell.

In one aspect, the present invention provides a method for antagonizing the activity of PCSK9 in a subject, which comprises administering to the subject a therapeutically effective amount of a PCSK9-specific antagonist of the present invention. In some embodiments, the methods for antagonizing PCSK9 function are for the treatment, as defined herein, of a PCSK9-associated disease, disorder or condition or, alternatively, for providing therapy in a disease, disorder or condition that could benefit from the effects of a PCSK9 antagonist.

The present invention, thus, contemplates the use of PCSK9-specific antagonists described herein in various methods of treatment where antagonizing PCSK9 function is desirable. As used herein, the term "method of treatment" relates to a course of action resulting in a change in at least one symptom of a disease state which can be prophylactic or therapeutic in nature. In some embodiments, the present invention relates to a method of treatment for a condition associated with/attributed to PCSK9 activity, or a condition where the functioning of PCSK9 is contraindicated for a particular subject, the method comprising administering to the subject a therapeutically effective amount of a PCSK9-antagonist compound of the present invention. In some embodiments, the condition may be atherosclerosis, hypercholesterolemia, coronary heart disease, metabolic syndrome, acute coronary syndrome or related cardiovascular disease and cardiometabolic conditions, or may be a disease state or condition in which PCSK9 activity is contraindicated.

Methods of treatment in accordance with the present invention comprise administering to an individual a therapeutically (or prophylactically) effective amount of a PCSK9-specific antagonist of the present invention. Use of the terms "therapeutically effective" or "prophylactically effective" in reference to an amount refers to the amount necessary at the intended dosage to achieve the desired therapeutic/prophylactic effect for the period of time desired. The desired effect may be, for example, the alleviation, amelioration, reduction or cessation of at least one symptom associated with the treated condition. These amounts will vary, as the skilled artisan will appreciate, according to various factors, including but not limited to the disease state, age, sex and weight of the individual, and the ability of the PCSK9-specific antagonist to elicit the desired effect in the individual. The response may be documented by in vitro assay, in vivo non-human animal studies, and/or further supported from clinical trials.

In some embodiments it is preferred to administer a PCSK9 antagonist compound of the invention in the form of a pharmaceutical composition as described herein.

Dosing of antagonist therapeutics is well within the realm of the skilled artisan, see, e.g., Lederman et al., 1991 *Int. J. Cancer* 47:659-664; Bagshawe et al., 1991 *Antibody, Immunoconjugates and Radiopharmaceuticals* 4:915-922, and will vary based on a number of factors, for example, but not limited to, those mentioned above, including the condition of the patient, the area being treated, the route of administration, and the treatment desired, for example, prophylaxis or acute treatment and the like. A physician or veterinarian of ordinary skill can readily determine and prescribe the effective therapeutic amount of the antagonist.

The subject may be in need of, or desire, treatment for an existing disease or medical condition. As used herein, the subject "in need" of treatment of an existing condition encompasses both a determination of need by a medical professional as well as the desire of the subject for such treatment. When a compound or a salt thereof is provided in combination with one or more other active agents, "administration" and its variants are each understood to include provision of the compound or its salt and the other agents contemporaneously or simultaneously or over a course of separate administrations over a period of time. When the agents of a combination are administered at the same time, they can be administered together in a single composition or they can be administered separately. It is understood that a "combination" of active agents can be a single composition containing all of the active agents or multiple compositions each containing one or more of the active agents. In the case of two active agents a combination can be either a single composition comprising both agents or two separate compositions each comprising one of the agents; in the case of three active agents a combination can be either a single composition comprising all three agents, three separate compositions each comprising one of the agents, or two compositions one of which comprises two of the agents and the other comprises the third agent; and so forth.

The compositions and combinations of the present invention are suitably administered in effective amounts. The term "effective amount" means the amount of active compound sufficient to antagonize PCSK9 and thereby elicit the response being sought (i.e., induce a therapeutic response in the treatment or management of conditions associated with or impacted by PCSK9 function, including, but not limited to atherosclerosis, hypercholesterolemia, coronary heart disease, metabolic syndrome, acute coronary syndrome, and related cardiovascular disease and cardiometabolic conditions in an animal or human).

The actual dosage employed may be varied depending upon the requirements of the patient and the severity of the condition being treated. Determination of the proper dosage regimen for a particular situation is within the skill in the art, for example, as described in the standard literature, for example, as described in the "Physicians' Desk Reference" (PDR), e.g., 1996 edition (Medical Economics Company, Montvale, N.J. 07645-1742, USA), the Physician's Desk Reference, 56th Edition, 2002 (published by Medical Economics company, Inc. Montvale, N.J. 07645-1742), or the Physician's Desk Reference, 57th Edition, 2003 (published by Thompson PDR, Montvale, N.J. 07645-1742); the disclosures of which is incorporated herein by reference thereto. For convenience, the total daily dosage may be divided and administered in portions during the day as required or delivered continuously.

The PCSK9-specific antagonist may be administered to an individual by any route of administration appreciated in the art, including but not limited to oral administration, administration by injection (specific embodiments of which include intravenous, subcutaneous, intraperitoneal or intramuscular injection), or administration by inhalation, intranasal, or topical administration, either alone or in combination with other agents designed to assist in the treatment of the individual. The PCSK9-specific antagonist may also be administered by injection devices, injector pens, needleless devices; and subcutaneous patch delivery systems. The route of administration should be determined based on a number of considerations appreciated by the skilled artisan including, but not limited to, the desired physiochemical characteristics of the treatment.

One or more additional pharmacologically active agents may be administered in combination with a compound of Formula I. An additional active agent (or agents) is intended to mean a pharmaceutically active agent (or agents) that is active in the body, including pro-drugs that convert to pharmaceutically active form after administration, which are different from the compound of Formula I, and also includes free-acid, free-base and pharmaceutically acceptable salts of said additional active agents. Generally, any suitable additional active agent or agents, including but not limited to anti-hypertensive agents, anti-atherosclerotic agents such as a lipid modifying compound, anti-diabetic agents and/or antiobesity agents may be used in any combination with the compound of Formula I in a single dosage formulation (a fixed dose drug combination), or may be administered to the subject in one or more separate dosage formulations which allows for concurrent or sequential administration of the active agents (co-administration of the separate active agents).

Examples of additional active agents which may be employed include but are not limited to angiotensin converting enzyme inhibitors (e.g., alacepril, benazepril, captopril, ceronapril, cilazapril, delapril, enalapril, enalaprilat, fosinopril, imidapril, lisinopril, moveltipril, perindopril, quinapril, ramipril, spirapril, temocapril, ortrandolapril), angiotensin II receptor antagonists (e.g., losartan i.e., COZAAR®, valsartan, candesartan, olmesartan, telmesartan and any of these drugs used in combination with hydrochlorothiazide such as HYZAAR®); neutral endopeptidase inhibitors (e.g., thiorphan and phosphoramidon), aldosterone antagonists, aldosterone synthase inhibitors, renin inhibitors (e.g. urea derivatives of di- and tri-peptides (See U.S. Pat. No. 5,116,835), amino acids and derivatives (U.S. Pat. Nos. 5,095,119 and 5,104,869), amino acid chains linked by non-peptidic bonds (U.S. Pat. No. 5,114,937), di- and tri-peptide derivatives, peptidyl amino diols and peptidyl beta-aminoacyl aminodiol carbamates, and small molecule renin inhibitors (including diol sulfonamides and sulfinyls), N-morpholino derivatives, N-heterocyclic alcohols and pyrolimidazolones; also, pepstatin derivatives and fluoro- and chloro-derivatives of statone-containing peptides, enalkrein, RO 42-5892, A 65317, CP 80794, ES 1005, ES 8891, SQ 34017, aliskiren (2(S),4(S),5(S),7(S)-N-(2-carbamoyl-2-methylpropyl)-5-amino-4-hydroxy-2,7-diisopropyl-8-[4-methoxy-3-(3-methoxypropoxy)-phenyl]-octanamid hemifumarate) SPP600, SPP630 and SPP635), endothelin receptor antagonists, phosphodiesterase-5 inhibitors (e.g. sildenafil, tadalfil and vardenafil), vasodilators, calcium channel blockers (e.g., amlodipine, nifedipine, veraparmil, diltiazem, gallopamil, niludipine, nimodipins, nicardipine), potassium channel activators (e.g., nicorandil, pinacidil, cromakalim, minoxidil, aprilkalim, loprazolam), diuretics (e.g., hydrochlorothiazide), sympatholitics, beta-adrenergic blocking drugs (e.g., propranolol, atenolol, bisoprolol, carvedilol, metoprolol, ormetoprolol tartate), alpha adrenergic blocking drugs (e.g., doxazocin, prazocin or alpha methyldopa) central alpha adrenergic agonists, peripheral vasodilators (e.g. hydralazine); lipid lowering agents e.g., HMG-CoA reductase inhibitors such as simvastatin and lovastatin which are marketed as ZOCOR® and MEVACOR® in lactone pro-drug form and function as inhibitors after administration, and pharmaceutically acceptable salts of dihydroxy open ring acid HMG-CoA reductase inhibitors such as atorvastatin (particularly the calcium salt sold in LIPITOR®), rosuvastatin (particularly the calcium salt sold in CRESTOR®), pravastatin (particularly the sodium salt sold in PRAVACHOL®), fluvastatin (particularly the sodium salt sold in LESCOL®), crivastatin, and pitavastatin; a cholesterol absorption inhibitor such as ezetimibe (ZETIA®) and ezetimibe in combination with any other lipid lowering agents such as the HMG-CoA reductase inhibitors noted above and particularly with simvastatin (VYTORIN®) or with atorvastatin calcium; niacin in immediate-release or controlled release forms and/or with an HMG-CoA reductase inhibitor; niacin receptor agonists such as acipimox and acifran, as well as niacin receptor partial agonists; metabolic altering agents including insulin and insulin mimetics (e.g., insulin degludec, insulin glargine, insulin lispro), dipeptidyl peptidase-IV (DPP-4) inhibitors (e.g., sitagliptin, alogliptin, omarigliptin, linagliptin, vildagliptin); insulin sensitizers, including (i) PPARγ agonists, such as the glitazones (e.g. pioglitazone, AMG 131, MBX2044, mitoglitazone, lobeglitazone, IDR-105, rosiglitazone, and balaglitazone), and other PPAR ligands, including (1) PPARα/γ dual agonists (e.g., ZYH2, ZYH1, GFT505, chiglitazar, muraglitazar, aleglitazar, sodelglitazar, and naveglitazar); (2) PPARa agonists such as fenofibric acid derivatives (e.g., gemfibrozil, clofibrate, ciprofibrate, fenofibrate, bezafibrate), (3) selective PPARγ modulators (SPPARγM's), (e.g., such as those disclosed in WO 02/060388, WO 02/08188, WO 2004/019869, WO 2004/020409, WO 2004/020408, and WO 2004/066963); and (4) PPARγ partial agonists; (ii) biguanides, such as metformin and its pharmaceutically acceptable salts, in particular, metformin hydrochloride, and extended-release formulations thereof, such as Glumetza™, Fortamet™, and GlucophageXR™; and (iii) protein tyrosine phosphatase-1 B (PTP-1B) inhibitors (e.g., ISIS-113715 and TTP814); insulin or insulin analogs (e.g., insulin detemir, insulin glulisine, insulin degludec, insulin glargine, insulin lispro and inhalable formulations of each); leptin and leptin derivatives and agonists; amylin and amylin analogs (e.g., pramlintide); sulfonylurea and non-sulfonylurea insulin secretagogues (e.g., tolbutamide, glyburide, glipizide, glimepiride, mitiglinide, meglitinides, nateglinide and repaglinide); α-glucosidase inhibitors (e.g., acarbose, voglibose and miglitol); glucagon receptor antagonists (e.g., MK-3577, MK-0893, LY-2409021 and KT6-971); incretin mimetics, such as GLP-1, GLP-1 analogs, derivatives, and mimetics; and GLP-1 receptor agonists (e.g., dulaglutide, semaglutide, albiglutide, exenatide, liraglutide, lixisenatide, taspoglutide, CJC-1131, and BIM-51077, including intranasal, transdermal, and once-weekly formulations thereof); bile acid sequestering agents (e.g., colestilan, colestimide, colesevalam hydrochloride, colestipol, cholestyramine, and dialkylaminoalkyl derivatives of a cross-linked dextran), acyl CoA:cholesterol acyltransferase inhibitors, (e.g., avasimibe); antiobesity compounds; agents intended for use in inflammatory conditions, such as aspirin, non-steroidal anti-inflammatory drugs or NSAIDs, glucocorticoids, and selective cyclooxygenase-2 or COX-2 inhibitors; glucokinase activators (GKAs) (e.g., AZD6370); inhibitors of 11β-hydroxysteroid dehydrogenase type 1, (e.g., such as those disclosed in U.S. Pat. No. 6,730,690, and LY-2523199); CETP inhibitors (e.g., anacetrapib, torcetrapib, and evacetrapib); inhibitors of fructose 1,6-bisphosphatase, (e.g., such as those disclosed in U.S. Pat. Nos. 6,054,587; 6,110,903; 6,284,748; 6,399,782; and 6,489,476); inhibitors of acetyl CoA carboxylase-1 or 2 (ACC1 or ACC2); AMP-activated Protein Kinase (AMPK) activators; other agonists of the G-protein-coupled receptors: (i) GPR-109, (ii) GPR-119 (e.g., MBX2982 and PSN821), and (iii) GPR-40 (e.g., TAK875); SSTR3 antagonists (e.g., such as those disclosed in WO 2009/001836); neuromedin U receptor agonists (e.g., such as those disclosed in WO 2009/042053, including, but not limited to, neuromedin S (NMS)); SCD modulators; GPR-105 antagonists (e.g., such as those disclosed in WO 2009/000087); SGLT inhibitors (e.g., ASP1941, SGLT-3, empagliflozin, dapagliflozin, canagliflozin, BI-10773, ertugliflozin, remogliflozin, TS-071, tofogliflozin, ipragliflozin, and LX-4211); inhibitors of acyl coenzyme A: diacylglycerol acyltransferase 1 and 2 (DGAT-1 and DGAT-2); inhibitors of fatty acid synthase; inhibitors of acyl coenzyme A:monoacylglycerol acyltransferase 1 and 2 (MGAT-1 and MGAT-2); agonists of the TGR5 receptor (also known as GPBAR1, BG37, GPCR19, GPR131, and M-BAR); ileal bile acid transporter inhibitors; PACAP, PACAP mimetics, and PACAP receptor 3 agonists; PPAR agonists; protein tyrosine phosphatase-1B (PTP-1B) inhibitors; IL-1b antibodies, (e.g., XOMA052 and canakinumab); and bromocriptine mesylate and rapid-release formulations thereof; or with other drugs beneficial for the treatment of the above-mentioned conditions or disorders including the free-acid, free-base, and pharmaceutically acceptable salt forms of the above active agents where chemically possible.

The compounds of the present invention can be readily prepared according to the following reaction schemes and examples, or modifications thereof, using readily available starting materials, reagents and conventional synthesis procedures. In these reactions, it is also possible to make use of known variants. Other methods for preparing compounds of the invention will be readily apparent to the person of ordinary skill in the art in light of the following reaction schemes and examples. Abbreviations listed below may used in the exemplary schemes and/or examples herein.

ACN is acetonitrile
AcOH is acetic acid
AcO—$NH_4$ is ammonium acetate
$Boc_2O$ is di-tert-butyl dicarbonate
Bn is benzyl
BnBr is benzyl bromide
BzCl is benzoyl chloride
$CBr_4$ is perbromomethane
Cbz-Cl is benzyl chloroformate
DBU is 1,8-Diazabicyclo[5.4.0]undec-7-ene
DCC is dicyclohexylcarbodiimide
DCE is 1,2-dichloroethane
DCM is dichloromethane
DEA is N,N-diethylamine
DIAD is (E)-diisopropyl diazene-1,2-dicarboxylate
DIEA or DIPEA is N,N-diisopropylethylamine
DMAP is 4-dimethylaminopyridine
DMF is N,N-dimethylformamide
DMSO is dimethyl sulfoxide
EA or EtOAc is ethyl acetate
EtOH is ethanol
$Et_2O$ is diethyl ether
Fmoc is fluorenylmethyloxycarbonyl protecting group
Fmoc-Cl is (9H-fluoren-9-yl)methyl carbonochloridate
Fmoc-D-Dap(Boc)-OH is N-alpha-(9-Fluorenylmethyloxycarbonyl)-N-beta-t-butyloxycarbonyl-D-2,3-diaminopropionic acid
Fmoc-Osu is Fmoc N-hydroxysuccinimide ester
HATU is 1-[bis(dimethylamino)methylene]-1H-1,2,3-triazolo[4,5-b]pyridinium 3-oxid hexafluorophosphate
HPLC is High Performance Liquid Chromatography
IPA is isopropyl alcohol
LiOH is lithium hydroxide
LC/MS is Liquid chromatography-mass spectrometry
$Me_3N$ is trimethyl amine
MeOH is methanol
MPLC is Medium pressure liquid chromatography
MsCl is methanesulfonyl chloride
$NaBH(OAc)_3$ is sodium triacetoxyborohydride
NMR is Nuclear Magnetic Resonance
NsCl is 4-nitrobenzene-1-sulfonyl chloride
PE is petroleum ether
$Pd_2(dba)_3(HCCl_3)$ is tris(dibenzylideneacetone)dipalladium (0)-chloroform adduct $PPh_3$ is triphenylphosphine
$PdCl_2(dppf)$ or $Pd(ii)(dppf)Cl_2$ is dichloro[1,1'-bis(diphenylphosphino)ferrocene]palladium(II)
$Pd(dppf)Cl_2CH_2Cl_2$ is dichloro[1,1'-bis(diphenylphosphino)ferrocene]palladium(I) dichloromethane adduct
$Pd(PPh_3)_4$ is tetrakis(triphenylphosphine)palladium
$PPT_s$ is pyridinium p-toluenesulfonate
$[Rh(OAc)_2]_2$ is rhodium(II) acetate dimer
RT or r.t. or rt is room temperature
tBuOAc is tert-butyl acetate
TEA is triethylamine
TFA is trifluoroacetic acid
TFE is tetrafluoroethylene
THF is tetrahydrofuran
$Tf_2O$ is trifluoromethanesulfonic anhydride
Teoc-OSu is 2,5-dioxopyrrolidin-1-yl (2-(trimethylsilyl)ethyl) carbonate
TBAF is tetrabutylammonium fluoride
TMS is tetramethylsilane
Zhan's catalyst 1B is dichloro(1,3-bis(2,4,6-trimethylphenyl)-2-imidazolidinylidene)((5-((dimethylamino)sulfonyl)-2-(1-methylethoxy-O)phenyl)methylene-C)ruthenium(II) [also described as 1,3-Bis(2,4,6-trimethylphenyl)-4,5-dihydroimidazol-2-ylidene[2-(i-propoxy)-5-(N,N-dimethylaminosulfonyl)phenyl[methyleneruthenium (II) dichloride]

Example 1 Preparation of Ex-B03

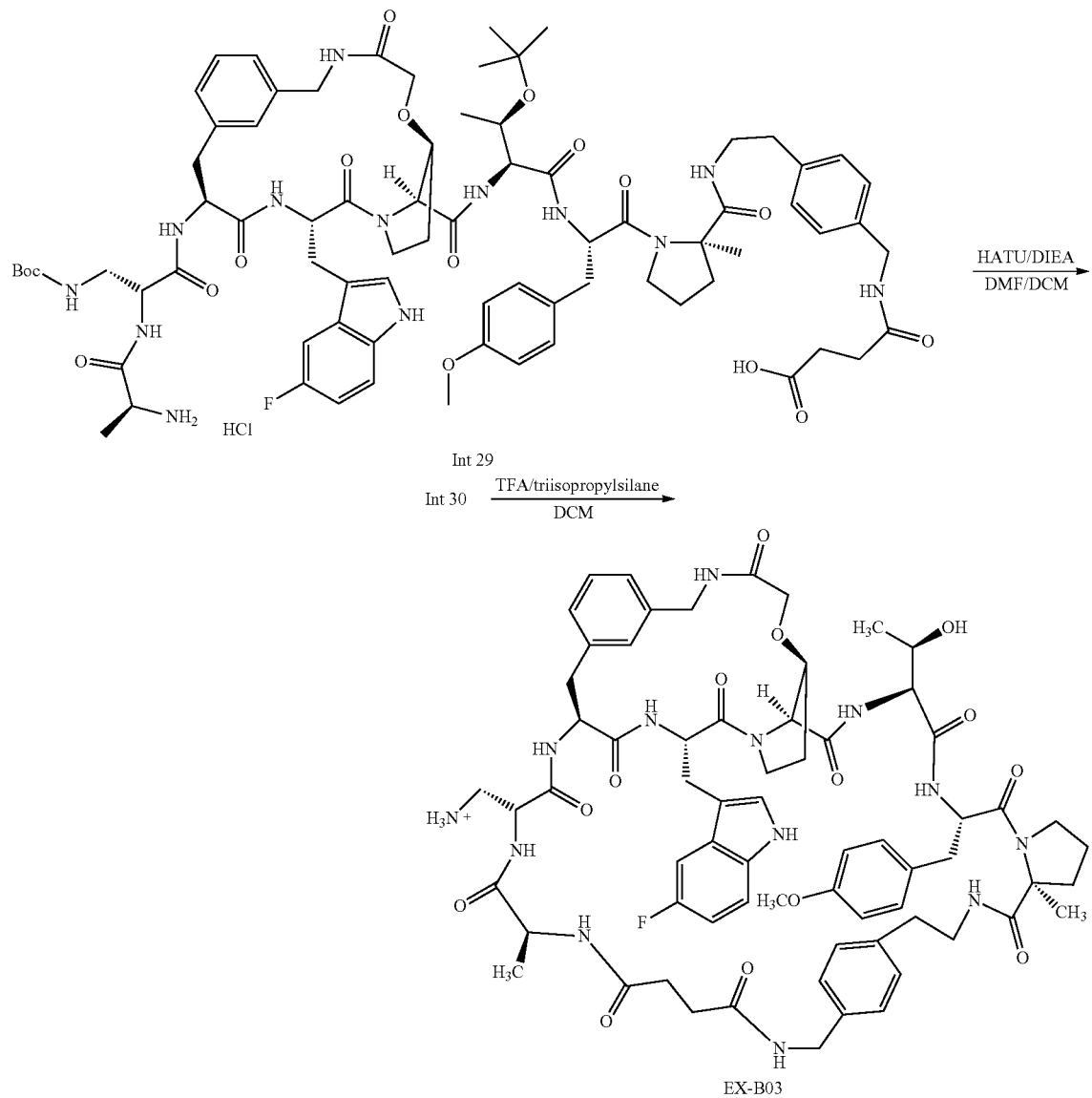

As illustrated above in Scheme 1, in general, compounds of the invention are prepared by forming intermediate compounds which contain key portions of the desired final compound and coupling them together using chemistry detailed below, followed by cyclization and derivatization of the ring with the desired substituents, as is illustrated below for the preparation of compound Ex-B04 (Example 2). Presented below also is the synthesis of the relevant intermediate compounds.

Preparation of Compound Ex-B03

Step I: Preparation of Compound Intermediate 30

To a solution of intermediate 29, prepared in accordance with the procedure detailed below, (41 mg, 0.027 mmol) in DMF (4 ml) at ambient temperature was added HATU (12.28 mg, 0.032 mmol), the resulting solution was stirred at rt for 30 min, then added $CH_2Cl_2$ (90 mL) followed by addition of DIEA (0.014 ml, 0.081 mmol), the resulting solution was stirred at room temperature for 1 hour. The volatile was removed on rotary evaporator, and the resulting DMF solution was purified on reverse phase MPLC (C18) using acetonitrile (0.05% TFA)/water (0.05% TFA) as eluting solvents to give Intermediate 30. LC/MS: $(M+1)^+$: 1469.0

Step II: Preparation of Compound Ex-B03

To the solution of intermediate 30 (2.7 mg, 1.838 µmol) in $CH_2Cl_2$ (1 ml) was added triisopropylsilane (0.873 mg, 5.52 µmol) and HCl (0.1 mL, 0.400 mmol) (4N in dioxane), the resulting solution was stirred at ambient temperature for 1 hour, then concentrated on rotary evaporator, the residue (Ex-B03 crude) was purified on reverse phase HPLC using acetonitrile (0.05% TFA)/water (0.05% TFA) eluting solvents to give Example Compound EX-B03. LC/MS: (M+1)+: 1312.0.
Preparation of the following intermediates from which intermediate Int 29 was ultimately synthesized are described next:
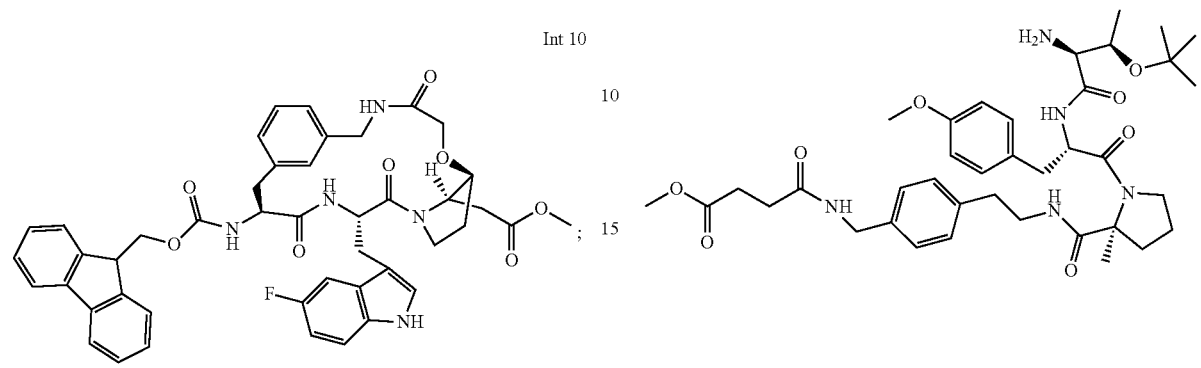
Preparation of Intermediate 10
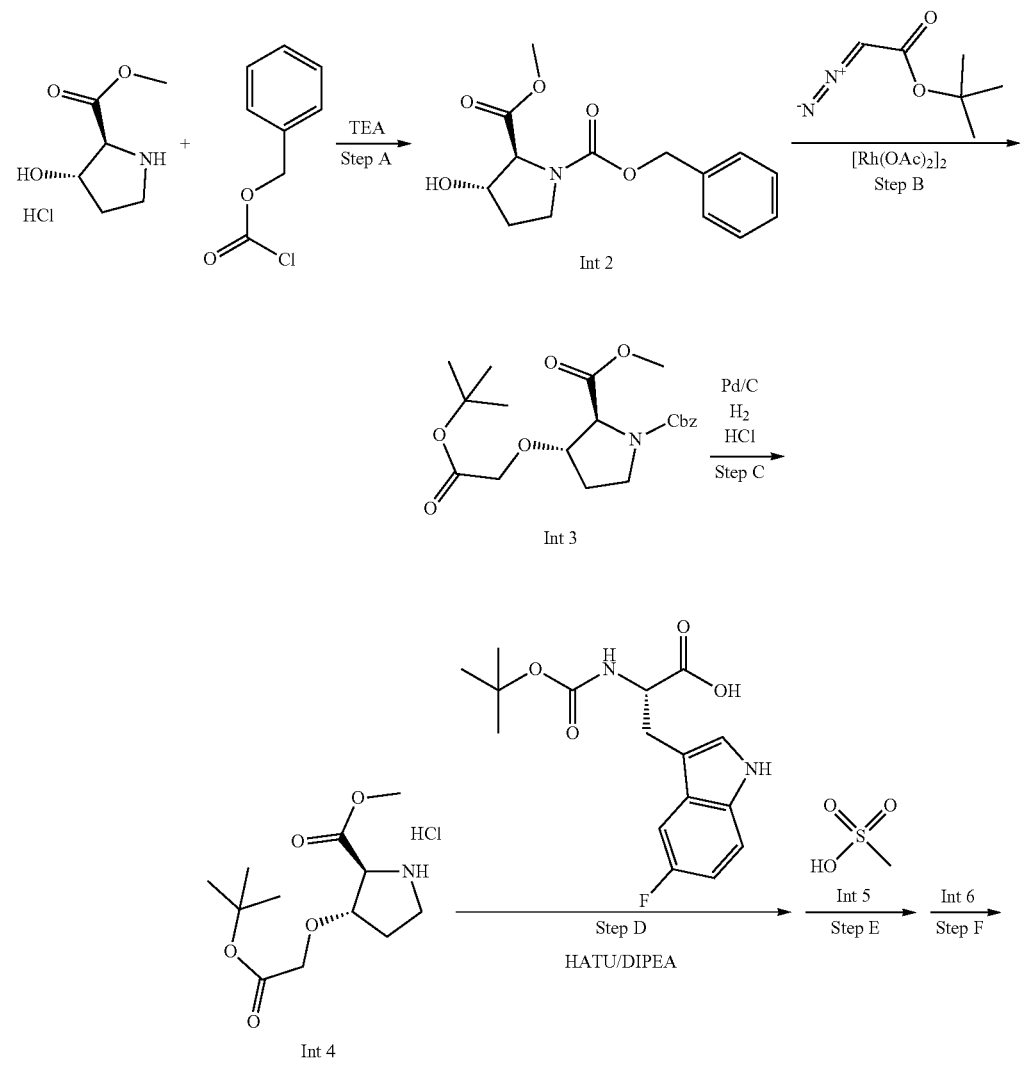

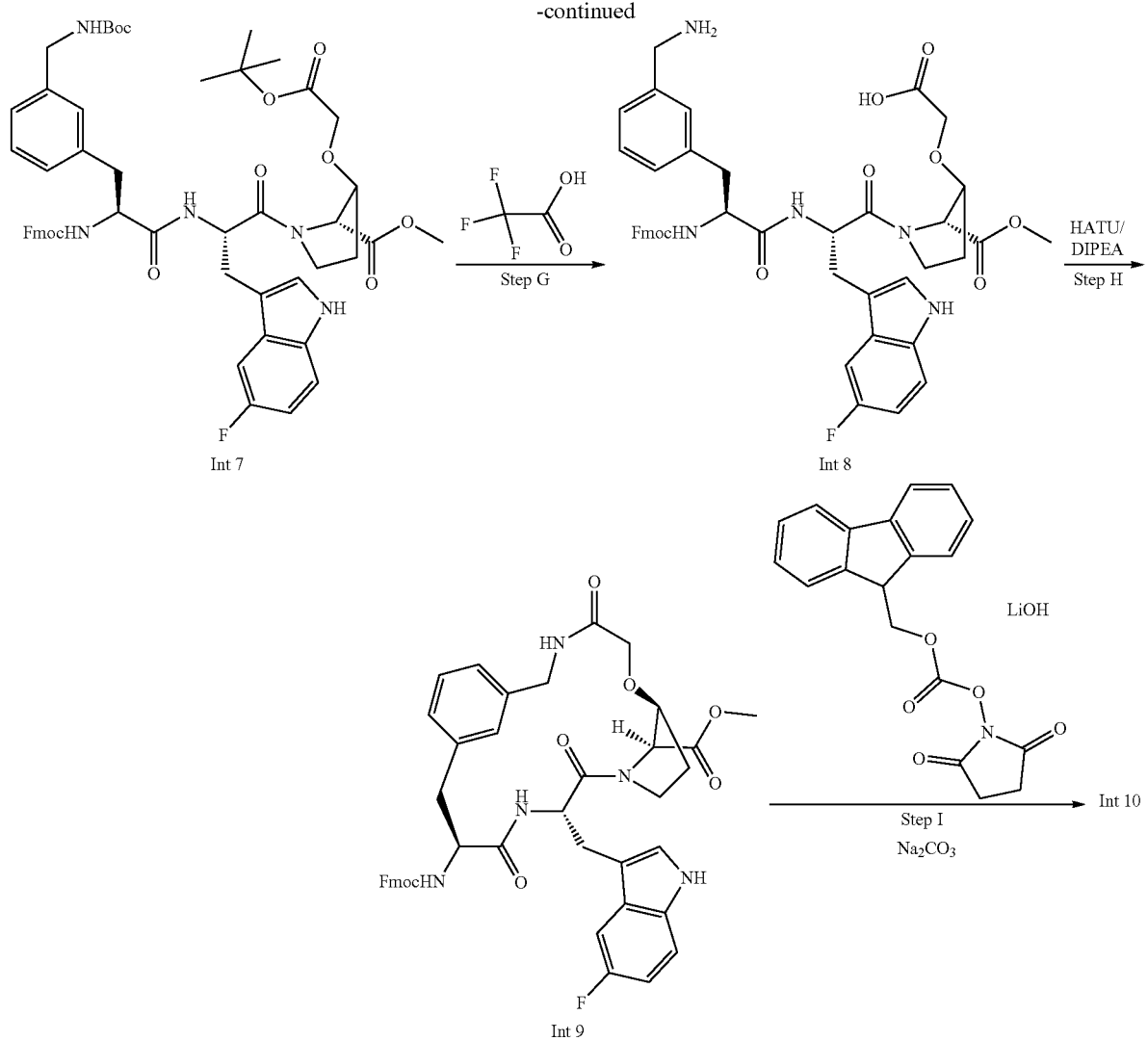

Step A: 1-benzyl 2-methyl (2S,3S)-3-hydroxypyrrolidine-1,2-dicarboxylate (2)

Benzyl chloroformate (0.865 mL, 6.06 mmol) was added to a cold (ice bath) mixture of (2S,3S)-methyl 3-hydroxypyrrolidine-2-carboxylate hydrochloride 1 (1 g, 5.51 mmol), $CH_2Cl_2$ (55 mL) and TEA (1.919 mL, 13.77 mmol). The reaction was stirred at 0° C. for 1 h followed by $NH_4Cl$ (aq, sat) quench. The crude reaction mixture was worked up with water/dichloromethane and the combined DCM extracts were dried over $Na_2SO_4$, filtered and evaporated in vacuo. The pot residue was purified by reverse-phase chromatography (C18, 86 g cartridge). The column was eluted by a acetonitrile/water/0.1% v/v formic acid mixture (0% to 100%). Related fractions were pooled and evaporated in vacuo to afford a colorless solid as (2S,3S)-1-benzyl 2-methyl 3-hydroxypyrrolidine-1,2-dicarboxylate (1.3363 g, 4.78 mmol, 87% yield). LCMS calc.=279.11; found=280.29.

Step B: 1-benzyl 2-methyl (2S,3S)-3-(2-(tert-butoxy)-2-oxoethoxy)pyrrolidine-1,2-dicarboxylate (3)

A mixture of Intermediate 2 (1.2296 g, 4.40 mmol) and DCM (40 mL) was degassed with nitrogen for 5 min followed by addition of rhodium(II) acetate dimer (0.195 g, 0.440 mmol), and the mixture cooled in an ice bath. Tert-butyl diazoacetate (0.915 mL, 6.60 mmol) was added into this mixture slowly over 80 min (syringe pump). An aliquot was taken and partitioned w/ water and the organic layer was checked by LCMS. The reaction was stirred at 0° C. for additional 1.5 h after addition of diazo reagent and then quenched by adding water. The reaction crude was worked up with water/dichloromethane. The combined organic extracts were evaporated in vacuo. The pot residue was purified by reverse-phase chromatography (C18, 130 g cartridge). The column was eluted by a acetonitrile/water/ 0.1% v/v formic acid mixture (0% to 100%). Related fractions were pooled and evaporated in vacuo to afford (2S,3S)-1-benzyl 2-methyl 3-(2-(tert-butoxy)-2-oxoethoxy) pyrrolidine-1,2-dicarboxylate (1.0499 g) and recovered starting material (2S,3S)-1-benzyl 2-methyl 3-hydroxypyrrolidine-1,2-dicarboxylate. LCMS calc.=393.18; found=416.39 (M+Na$^+$).

Step C: (2S,3S)-methyl 3-(2-(tert-butoxy)-2-oxoethoxy)pyrrolidine-2-carboxylate Hydrochloride (4)

A mixture of Intermediate 3 (1.0499 g, 2.67 mmol), MeOH (25 mL) and Pd—C (0.284 g, 0.267 mmol) were degassed with cycles of vacuum/$H_2$ flush then stirred under a balloon of $H_2$ at room temperature overnight. The reaction crude was filtered and HCl (2.67 mL, 2.67 mmol) was added into the filtrate. The filtrate was concentrated under reduced pressure to afford (2S,3S)-methyl 3-(2-(tert-butoxy)-2-oxoethoxy)pyrrolidine-2-carboxylate hydrochloride. LCMS calc.=259.14; found=260.34.

Step D: (2S,3S)-methyl 3-(2-(tert-butoxy)-2-oxoethoxy)-1-((S)-2-((tert-butoxycarbonyl)amino)-3-(5-fluoro-1H-indol-3-yl)propanoyl)pyrrolidine-2-carboxylate (5)

Intermediate 4 (346 mg, 1.170 mmol), DMF (3 ml) and (S)-2-((tert-butoxycarbonyl)amino)-3-(5-fluoro-1H-indol-3-yl)propanoic acid (377 mg, 1.170 mmol) were stirred in a ice bath followed by addition of Hunig's Base (0.511 ml, 2.92 mmol) and HATU (489 mg, 1.287 mmol) for 1 hour. The reaction crude was purified by reverse phase chromatography (C18, 130 g cartridge). The column was eluted by an acetonitrile/water/0.1% v/v formic acid mixture (0% to 62%). Related fractions were pooled and evaporated to afford (2S,3S)-methyl 3-(2-(tert-butoxy)-2-oxoethoxy)-1-((S)-2-((tert-butoxycarbonyl)amino)-3-(5-fluoro-1H-indol-3-yl)propanoyl)pyrrolidine-2-carboxylate. LCMS calc.=563.26; found=586.48 (M+Na$^+$).

Step E: (2S,3S)-methyl 1-((S)-2-amino-3-(5-fluoro-1H-indol-3-yl)propanoyl)-3-(2-(tert-butoxy)-2-oxoethoxy)pyrrolidine-2-carboxylate Methanesulfonate (6)

Methanesulfonic acid (0.046 ml, 0.710 mmol) was added into a room temperature mixture of Intermediate 5 (200 mg, 0.355 mmol) in t-butyl acetate (3 ml) and $CH_2Cl_2$ (0.750 ml). The reaction was stirred at room temperature for additional 2 h. LCMS indicated completion of reaction, which was used in the next step without further purification. LCMS calc.=463.21; found=464.30.

Step F: methyl (2S,3S)-1-((S)-2-((S)-2-((((9H-fluoren-9-yl)methoxy)carbonyl)amino)-3-(3-(((tert-butoxycarbonyl)amino)methyl)phenyl)propanamido)-3-(5-fluoro-1H-indol-3-yl)-propanoyl)-3-(2-(tert-butoxy)-2-oxoethoxy)pyrrolidine-2-carboxylate (7)

(S)-2-(((((9H-fluoren-9-yl)methoxy)carbonyl)amino)-3-(3-(((tert-butoxycarbonyl)amino)-methyl)phenyl)propanoic acid (211 mg, 0.409 mmol), DMF (5 ml), HATU (169 mg, 0.445 mmol) and Hunig's Base (0.373 ml, 2.134 mmol) were stirred at room temperature and transferred into the crude mixture from Step E. The reaction was stirred at room temperature for 20 minutes. The reaction mixture was purified by reverse-phase chromatography (C18, 130 g cartridge). The column was eluted by a acetonitrile/water/0.1% v/v formic acid mixture (0% to 100%). Related fractions were pooled and evaporated in vacuo to afford a colorless solid as (2S,3S)-methyl 1-((S)-2-((S)-2-((((9H-fluoren-9-yl)methoxy)carbonyl)amino)-3-(3-(((tert-butoxycarbonyl)amino)methyl)phenyl)propanamido)-3-(5-fluoro-1H-indol-3-yl)propanoyl)-3-(2-(tert-butoxy)-2-oxoethoxy)pyrrolidine-2-carboxylate. LCMS calc.=961.43; found=962.24.

Step G: 2-(((2S,3S)-1-((S)-2-((S)-2-((((9H-fluoren-9-yl)methoxy)carbonyl)amino)-3-(3-(aminomethyl)phenyl)propanamido)-3-(5-fluoro-1H-indol-3-yl)propanoyl)-2-(methoxy-carbonyl)pyrrolidin-3-yl)oxy)acetic Acid (8)

TFA (0.4 mL, 5.19 mmol) was added into a room temperature solution of Intermediate 7 (20.6 mg, 0.021 mmol) in $CH_2Cl_2$ (0.8 ml). The reaction was stirred at room temperature for 2 h. LCMS indicated completion of reaction. Volatiles were removed under reduced pressure to afford a yellow glass as the 2-(((2S,3S)-1-((S)-2-((S)-2-((((9H-fluoren-9-yl)methoxy)carbonyl)amino)-3-(3-(aminomethyl)phenyl)propanamido)-3-(5-fluoro-1H-indol-3-yl)propanoyl)-2-(methoxycarbonyl)pyrroidin-3-yl)oxy)acetic acid used in the next step without further purification. LCMS calc.=805.31; found=806.56.

Step H: methyl (12S,13S,9S,12S)-9-((((9H-fluoren-9-yl)methoxy)carbonyl)amino)-12-((5-fluoro-1H-indol-3-yl)methyl)-4,10,13-trioxo-2-oxa-5,11-diaza-1(3,1)-pyrroidina-7(1,3)-benzenacyclotridecaphane-12-carboxylate (9)

Intermediate 8, HATU (318 mg, 0.836 mmol) and DMF (50 ml) were stirred at room temperature followed by addition of Hunig's Base (0.508 ml, 2.91 mmol) for 20 minutes. The reaction crude was purified by reverse phase chromatography (C18, 360 g cartridge). The column was eluted by an acetonitrile/water/0.1% v/v formic acid mixture (0% to 100%). Related fractions were pooled and evaporated in vacuo to afford a colorless solid as methyl (12S,13S,9S,12S)-9-((((9H-fluoren-9-yl)methoxy)carbonyl)amino)-12-((5-fluoro-1H-indol-3-yl)methyl)-4,10,13-trioxo-2-oxa-5,11-diaza-1(3,1)-pyrrolidina-7(1,3)-benzenacyclotridecaphane-12-carboxylate. LCMS calc.=787.30; found=788.55 and 810.55 (M+Na$^+$).

Step I (12S,13S,9S,12S)-9-((((9H-fluoren-9-yl)methoxy)carbonyl)amino)-12-((5-fluoro-1H-indol-3-yl)methyl)-4,10,13-trioxo-2-oxa-5,11-diaza-1(3,1)-pyrrolidina-7(1,3)-benzenacyclotridecaphane-12-carboxylic Acid (10)

To the solution of Intermediate 9 in THE (10 mL), MeOH (5 ml), and water (4 ml) at 0° C. was added lithium hydroxide (2M, 0.685 mL, 1.371 mmol). The resulting solution was stirred at 0° C. for 4 h then quenched by addition of HCl (1M, 1.371 mL, 1.371 mmol). Volatiles were evaporated in vacuo. To the pot residue at 0° C. was added acetone (20 mL), sodium carbonate (24.22 mg, 0.228 mmol) and FMOC-OSU (51.4 mg, 0.152 mmol). The reaction was stirred at 0° C. for 3 h. Volatiles were evaporated on rotary evaporator. The resulting aqueous mixture was acidified to pH 4 followed by DCM extraction. The combined organic extracts were evaporated under reduced pressure. The pot residue was purified by reverse-phase chromatography (C18, 43 g cartridge). The column was eluted by an acetonitrile/water/0.1% v/v formic acid mixture (0% to 100%). Related fractions were pooled and evaporated in vacuo to afford a colorless solid as (12S,13S,9S,12S)-9-((((9H-fluoren-9-yl)methoxy)carbonyl)amino)-12-((5-fluoro-1H-indol-3-yl)methyl)-4,10,13-trioxo-2-oxa-5,11-diaza-1(3,1)-pyrrolidina-7(1,3)-benzenacyclotridecaphane-12-carboxylic acid. LCMS calc.=773.29; found=774.52.

Preparation of Intermediate 20

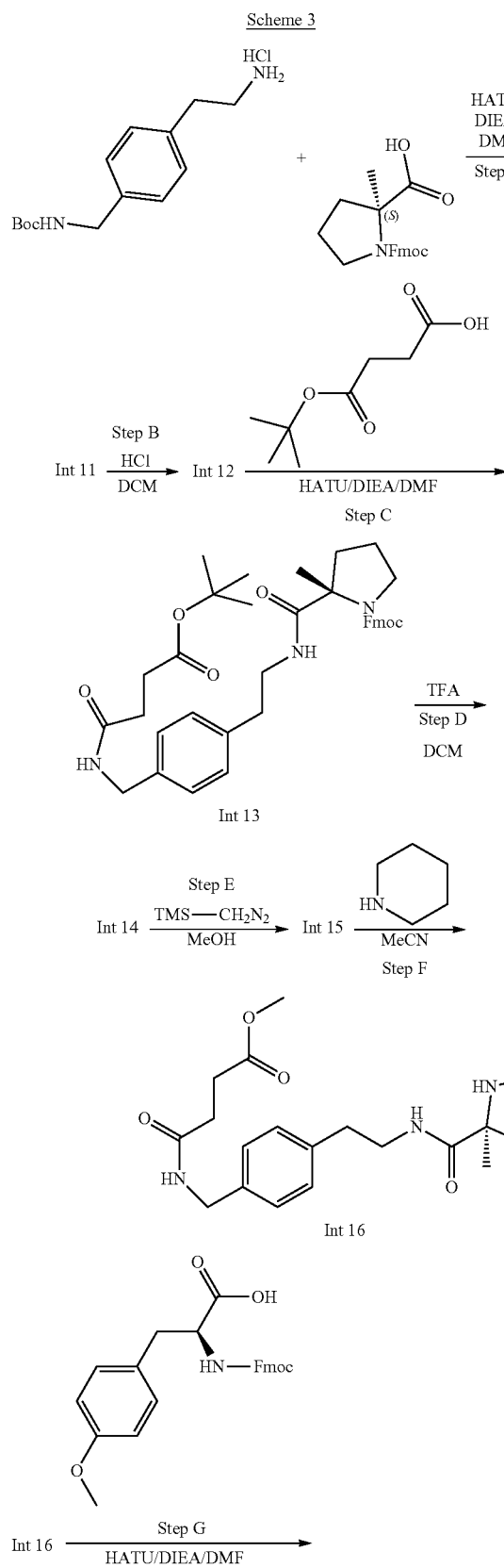

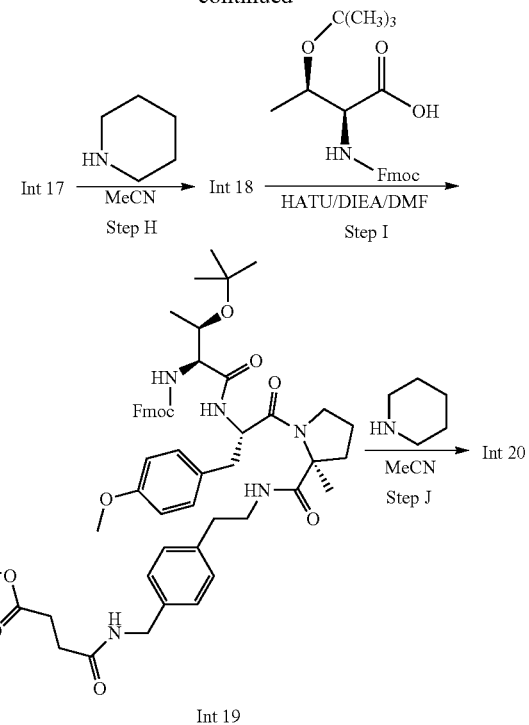

Step A: Preparation of Intermediate Compound 11

To (S)-1-(((9H-fluoren-9-yl)methoxy)carbonyl)-2-methylpyrrolidine-2-carboxylic acid (5.6 g, 15.94 mmol) and tert-butyl 4-(2-aminoethyl)benzylcarbamate hydrochloride (4.80 g, 16.73 mmol) in DMF (159 ml) at 0° C. was added HATU (7.27 g, 19.12 mmol) and N,N-diisopropylethylamine (8.33 ml, 47.8 mmol), the reaction mixture was warmed up to ambient temperature (about 25° C.) and stirred for 4.5 h, then diluted with H$_2$O (100 mL), extracted with EtOAc (3×200 mL)), washed with brine (3×200 mL). The ethylacetate extract was dried over MgSO$_4$, filtered, concentrated and purified by silica gel column using EtOAc/hexanes as eluting solvents to give intermediate 11. LC/MS: (M+1)$^+$: 584.5.

Step B: Preparation of Intermediate Compound 12

To the mixture of 11 (9.48 g, 16.24 mmol) in CH$_2$Cl$_2$ (81 ml) was added hydrochloride (4N in 1,4-dioxane, 16.24 ml, 65.0 mmol) in CH$_2$Cl$_2$ (81 ml), the resulting mixture was stirred at ambient temperature overnight, then the mixture was concentrated on rotary evaporator to give 12. LC/MS: (M+1)$^+$: 484.2.

Step C: Preparation of Intermediate Compound 13

To the suspension of 12 (4.15 g, 7.98 mmol) and 4-(tert-butoxy)-4-oxobutanoic acid (1.460 g, 8.38 mmol) in DMF (45 ml) was added HATU (3.64 g, 9.58 mmol), the resulting mixture was stirred at ambient temperature for 50 min, then partitioned between EtOAc (500 mL) and brine (200 mL). The organic phase was washed with brine (2×200 mL), dried over Na$_2$SO$_4$, concentrated and the residue was purified on a silica gel column using EtOAc/hexane as eluting solvents to give 13. LC/MS: (M+1)$^+$: 640.4.

Step D: Preparation of Intermediate Compound 14

To the solution of 13 (4.49 g, 7.02 mmol) in CH$_2$Cl$_2$ (20 ml) was added TFA (21.63 ml, 281 mmol), the solution was stirred at ambient temperature for 1 h, then concentrated on a rotary evaporator. The residue was azotropically concentrated from toluene, then dissolved in acetonitrile/water (100 mL, 1:1) and lyophilized. The residue was partitioned between EtOAc (400 mL) and HCl (pH4, 200 mL), the organic phase was washed with HCl (pH 4, 200 mL×3), brine, dried over Na$_2$SO$_4$, concentrated to give 14. LC/MS: (M+1)$^+$: 584.2.

Step E: Preparation of Intermediate Compound 15

To the solution of 14 (3.7 g, 6.34 mmol) in MeOH (50 ml) was added TMS-diazomethane (22.19 ml, 44.4 mmol) dropwise, after completion of the reaction, the reaction was quenched dropwise with acetic acid (ca. 0.2 mL), then concentrated and the residue was purified on silica gel column using EtOAc/hexane as eluting solvents to give 15. LC/MS: (M+1)$^+$: 598.3.

Step F: Preparation of Intermediate Compound 16

To the solution of 15 (2.83 g, 4.73 mmol) in acetonitrile (25 ml) was added piperidine (1.403 ml, 14.20 mmol) dropwise, the resulting solution was stirred at rt for 30 min, then concentrated and the residue was treated with acetonitrile (30 mL) and concentrated again. The cycle was repeated twice to give 16 as a crude. LC/MS: (M+1)$^+$: 376.2

Step G: Preparation of Intermediate Compound 17

To the solution of 16 (1.778 g, 4.74 mmol) and Fmoc-L-Tyr(Me)-OH (2.175 g, 5.21 mmol) in DMF (35 ml) was added HATU (2.071 g, 5.45 mmol) and DIEA (1.654 ml, 9.47 mmol), the resulting solution was stirred at ambient temperature for 40 min, then partitioned between EtOAC (200 ML) and brine (150 mL), the organic phase was further washed with brine (2×150 mL), dried over Na$_2$SO$_4$, concentrated and the residue was purified on silica gel column using EtOAc/hexane as eluting solvents to give 17. LC/MS: (M+1)$^+$: 775.2.

Step H: Preparation of Intermediate Compound 18

To the solution of 17 (3.36 g, 4.34 mmol) in acetonitrile (30 ml) was added piperidine (1.288 ml, 13.01 mmol), the resulting solution was stirred at ambient temperature for 30 min, then concentrated and the residue was treated with acetonitrile (30 mL) and concentrated again and further concentrated under high vacuum to give 18 as a crude. LC/MS: (M+1)$^+$: 553.2.

Step I: Preparation of Intermediate Compound 19

To the solution of 18 (2.396 g, 4.34 mmol) in DMF (40 ml) was added Fmoc-L-Thr(tBu)-OH (1.895 g, 4.77 mmol), HATU (1.896 g, 4.99 mmol), and DIEA (1.514 ml, 8.67 mmol), the resulting solution was stirred at ambient temperature for 1 h, then partitioned between EtOAc (200 mL) and brine (100 mL), the aqueous phase was extracted with EtOAc (150 mL), the combined organic phase was washed with brine (2×200 mL), dried over Na$_2$SO$_4$, concentrated and the residue was purified on silica gel column using EtOAc/hexane as eluting solvents to give 19. LC/MS: (M+1)$^+$: 932.2.

Step J: Preparation of Intermediate Compound 20

To the solution of 19 (0.155 g, 0.166 mmol) in acetonitrile (2 ml) was added piperidine (0.049 ml, 0.499 mmol), the resulting solution was stirred at ambient temperature for 1 hour, then concentrated and the residue was re-suspended in acetonitrile (10 mL) and concentrated, the cycle was repeated once and the residue was dried under high vacuum to give 20 as a crude product. LC/MS: (M+1)$^+$: 710.3.

Preparation of Intermediate 29 Via Intermediate 25

Intermediate 29 was prepared by joining together intermediates 10 and 20, prepared above, and further derivatizing as detailed in the following Schemes Preparation of Intermediate 25

Scheme 4

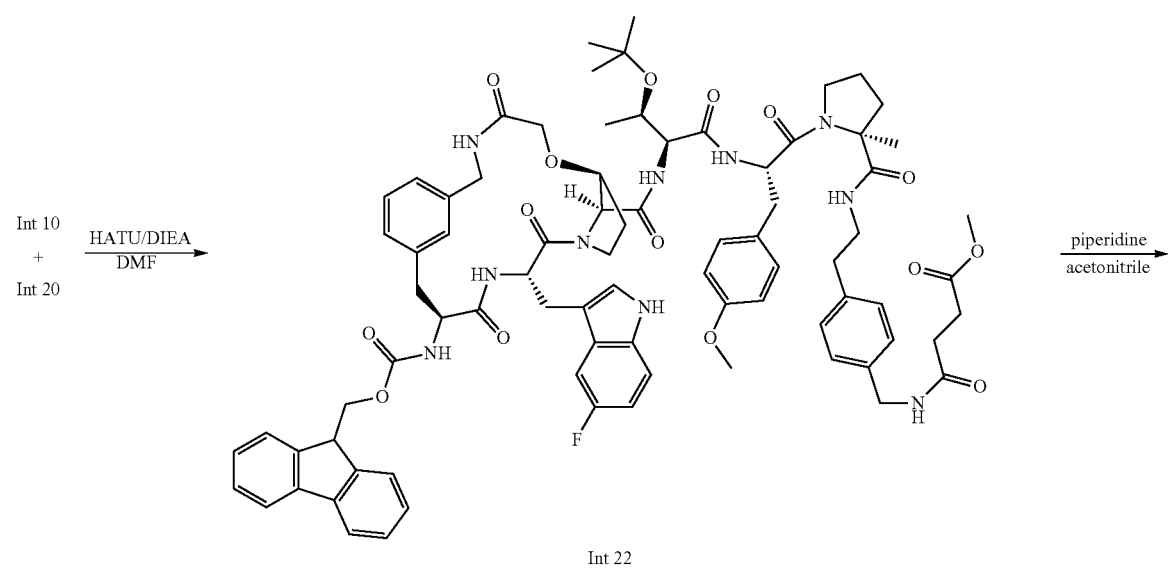

Int 22

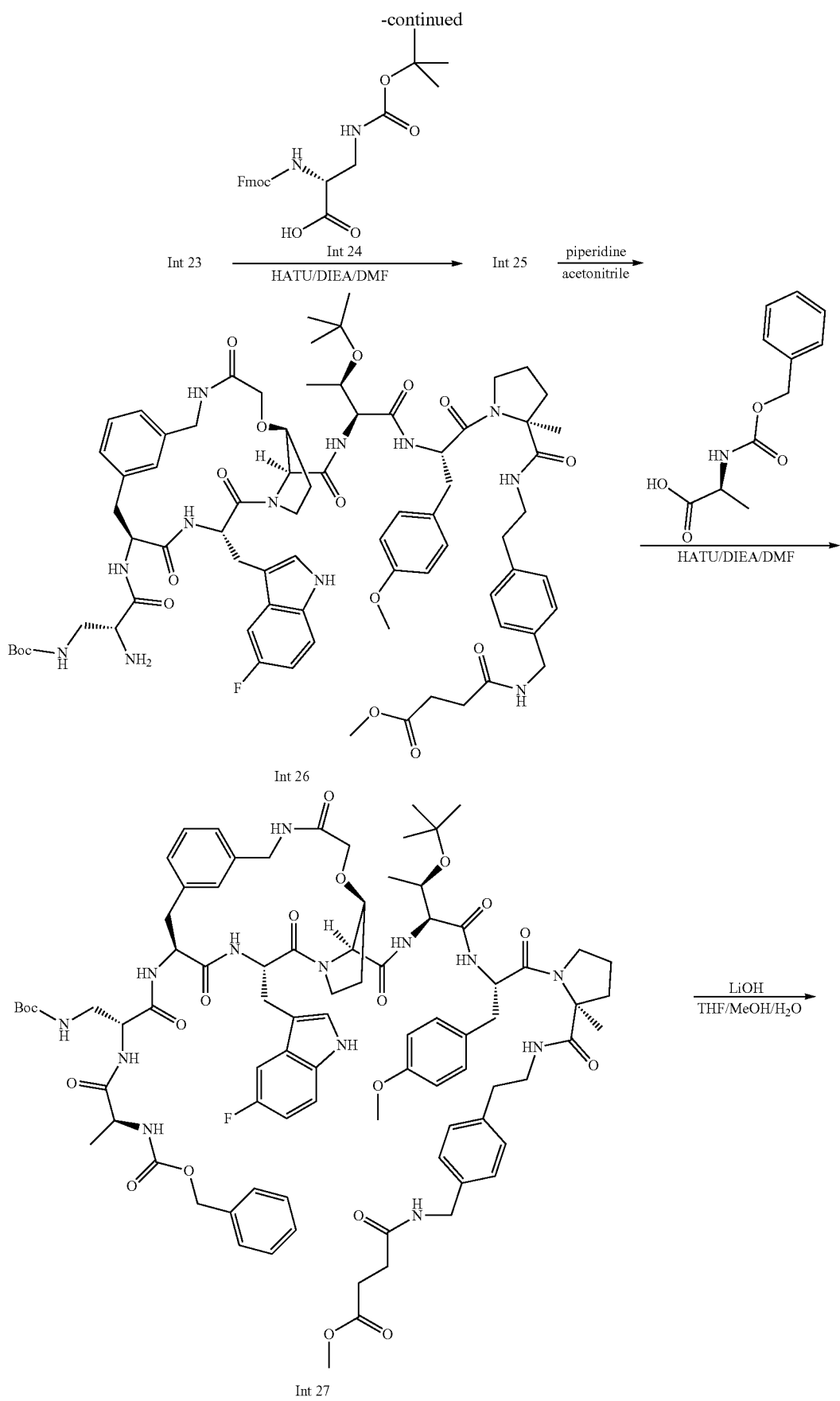

-continued

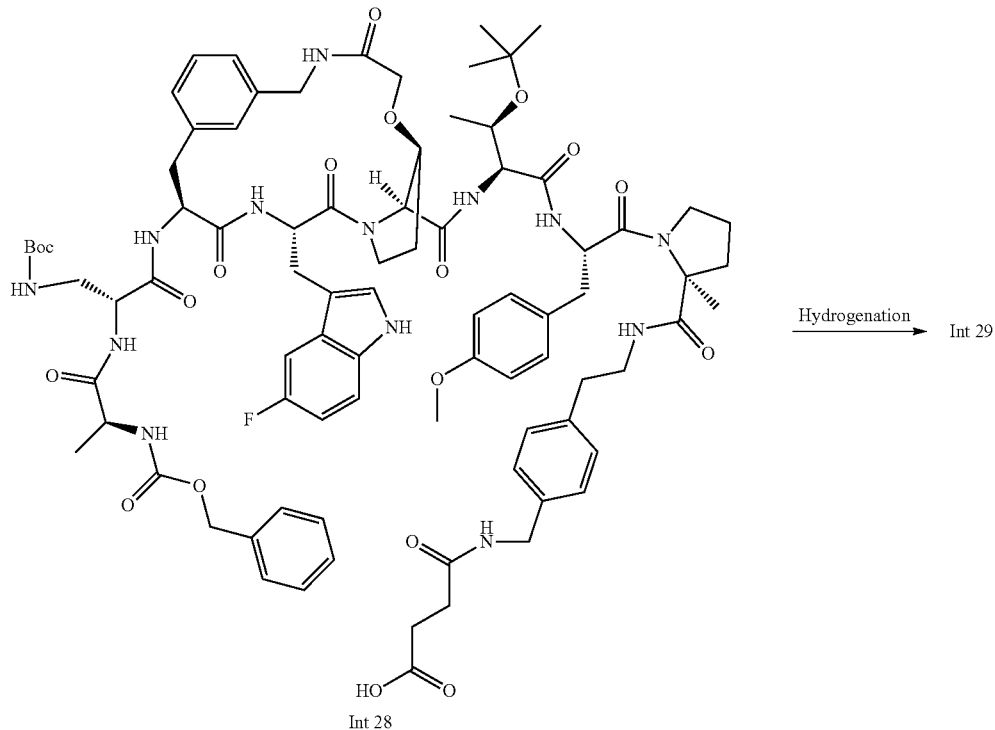

Int 28

→ Hydrogenation → Int 29

Step A: Preparation of Intermediate Compound 22

To the solution of Intermediate 10 (0.104 g, 0.134 mmol) and Intermediate 20 (0.118 g, 0.166 mmol) in DMF (3 ml) at 0° C. was added HATU (0.054 g, 0.141 mmol) and DIEA (0.047 ml, 0.269 mmol), the resulting solution was stirred at 0° C. for 4 h. The reaction solution was partitioned between EtOAc (200 mL) and brine (100 mL), the organic phase was further washed with brine (2×100 mL), dried over $Na_2SO_4$, concentrated and the residue was purified on silica gel column using MeOH/DCM as eluting solvents to give 22. LC/MS: $(M+1)^+$: 1465.9.

Step B: Preparation of Intermediate Compound 23

To the solution of 22 (0.196 g, 0.134 mmol) in acetonitrile (5 ml) was added piperidine (0.150 ml, 1.515 mmol), the resulting solution was stirred at rt for 40 min. then concentrated and the residue was resuspended in acetonitrile (5 mL) and concentrated again. The cycle was repeated once, the final residue was further dried under high vacuum for 1 h to give 23 as a crude product. LC/MS: $(M+1)^+$: 1243.6.

Step C: Preparation of Intermediate Compound 25

To the solution of 23 (197 mg, 0.158 mmol) and 24 (67.6 mg, 0.158 mmol) in DMF (4 ml) at 0° C. was added HATU (66.3 mg, 0.174 mmol) and DIEA (0.055 ml, 0.317 mmol), the resulting solution was stirred at 0° C. for 4 h. The solution was purified on reverse phase MPLC (C18 column) using acetonitrile (0.05% TFA)/water (0.05% TFA) as eluting solvents to give 25. LC/MS: $(M+1)^+$: 1651.6

Step D: Preparation of Intermediate Compound 26

To the solution of 25 (163 mg, 0.099 mmol) in acetonitrile (4 ml) was added piperidine (0.078 ml, 0.789 mmol), the resulting solution was stirred at ambient temperature for 1 hour, then the solution was concentrated and the residue was treated with acetonitrile (5 mL) and concentrated again, the cycle was repeated once again, the final residue was further dried under high vacuum for 1 h to give 26 as a crude product. LC/MS: $(M+1)^+$: 1429.5

Step E: Preparation of Intermediate Compound 27

To the solution of 26 (141 mg, 0.099 mmol) and Z-L-Ala-OH (22.02 mg, 0.099 mmol) in DMF (4 ml) was added HATU (41.3 mg, 0.108 mmol) and DIEA (0.034 ml, 0.197 mmol), the resulting solution was stirred at ambient temperature for 1 hour, then directly purified on reverse phase MPLC (C18 column) using acetonitrile (0.05% TFA)/water (0.05% TFA) as eluting solvents to give 27. LC/MS: $(M+1)^+$: 1634.2.

Step F: Preparation of Intermediate Compound 28

To the solution of 27 (160 mg, 0.098 mmol) in a mixture solvent of THF (6 ml), methanol (2 ml), and Water (2 ml) was added at 0° C. LiOH (0.4 ml, 0.400 mmol) dropwise, the resulting solution was stirred at 0° C. for 2 h, the volatile was evaporated on rotary evaporator at ambient temperature, the aqueous was acidified to pH 4 at 0° C., then extracted with 30% IPA/DCM (3×70 mL), the combined organic phase was dried over Na$_2$SO$_4$, concentrated to give 28. LC/MS: (M+1)$^+$: 1620.8.

Step G: Preparation of Intermediate Compound 29

To the solution of 28 (159 mg, 0.098 mmol) in MeOH (15 ml) was added 10% Pd/C (20.88 mg, 0.020 mmol), the resulting mixture was hydrogenated via H$_2$ balloon at rt for 5 h. The mixture was filtered through celite, the filtrate was concentrated and the residue was purified on reverse phase C18 column using acetonitrile (0.05% TFA)/water (0.05% TFA) as gradient to give product as TFA salt which was dissolved in acetonitrile (25 mL) and water (15 mL), to the solution at 0° C. was added HCl (5.00 ml, 0.5 mmol) dropwise, the resulting solution was stirred at 0° C. for 5 min, then lyophilized to give 29. LC/MS: (M+1)$^+$: 1487.2.

Example 2 Preparation of Ex-B04

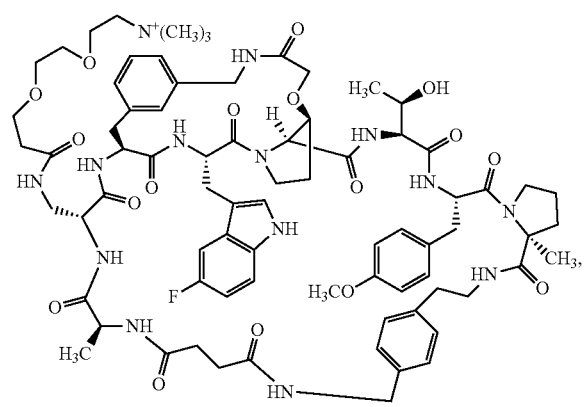

Ex-B04 was prepared by derivatizing intermediate Int-30, the penultimate intermediate to compound Ex-B03 prepared in Example 1, with intermediate Int 32, prepared in accordance with the following Scheme:

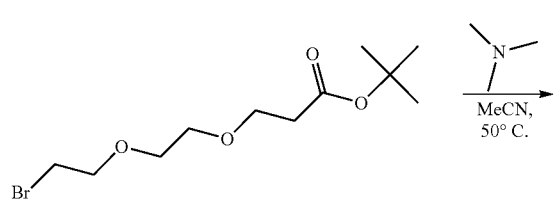

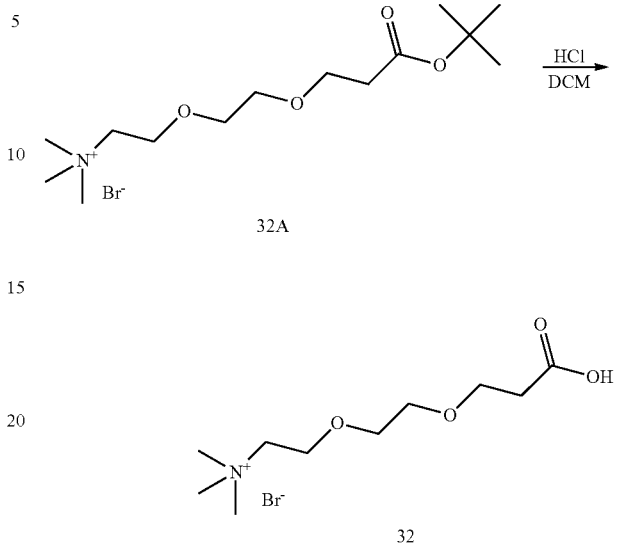

Step A: Preparation of Intermediate Compound 32A

To the solution of tert-butyl 3-(2-(2-bromoethoxy)ethoxy) propanoate (5 g, 16.82 mmol) in acetonitrile (10 ml) was added trimethylamine (33% in ethanol, 11.46 ml, 50.5 mmol), the resulting solution was heated at 50° C. overnight. The solution was concentrated to give 2-(2-(3-(tert-butoxy)-3-oxopropoxy)ethoxy)-N,N,N-trimethylethanaminium bromide (32A). LC/MS: (M)$^+$: 276.5.

Step B: Preparation of Intermediate 32

To the solution of 2-(2-(3-(tert-butoxy)-3-oxopropoxy) ethoxy)-N,N,N-trimethylethanaminium bromide (32A, 5.99 g, 16.81 mmol) in CH$_2$Cl$_2$ (20 ml) was added HCl (4N in dioxane) (21.01 ml, 84 mmol), the resulting solution was stirred at rt overnight. The solution was concentrated to give 2-(2-(2-carboxyethoxy)ethoxy)-N,N,N-trimethyl-ethanaminium bromide (32). LC/MS: (M)$^+$: 220.1

Preparation of Ex-B04

To the solution of Int 30 (74.1 mg, 0.055 mmol) and Int 32 (19.79 mg, 0.066 mmol) in DMF (5 ml) was added HATU (25.06 mg, 0.066 mmol) and DIEA (0.029 ml, 0.165 mmol), the resulting solution was stirred at rt for 50 min. then purified on reverse phase HPLC using acetonitrile (0.1% formic acid)/water (0.1% formic acid) as mobile phase to yield Ex=B04. LC/MS: M$^+$: 1514.2.

Example 3: Preparation of Ex-B01 and Ex-B02

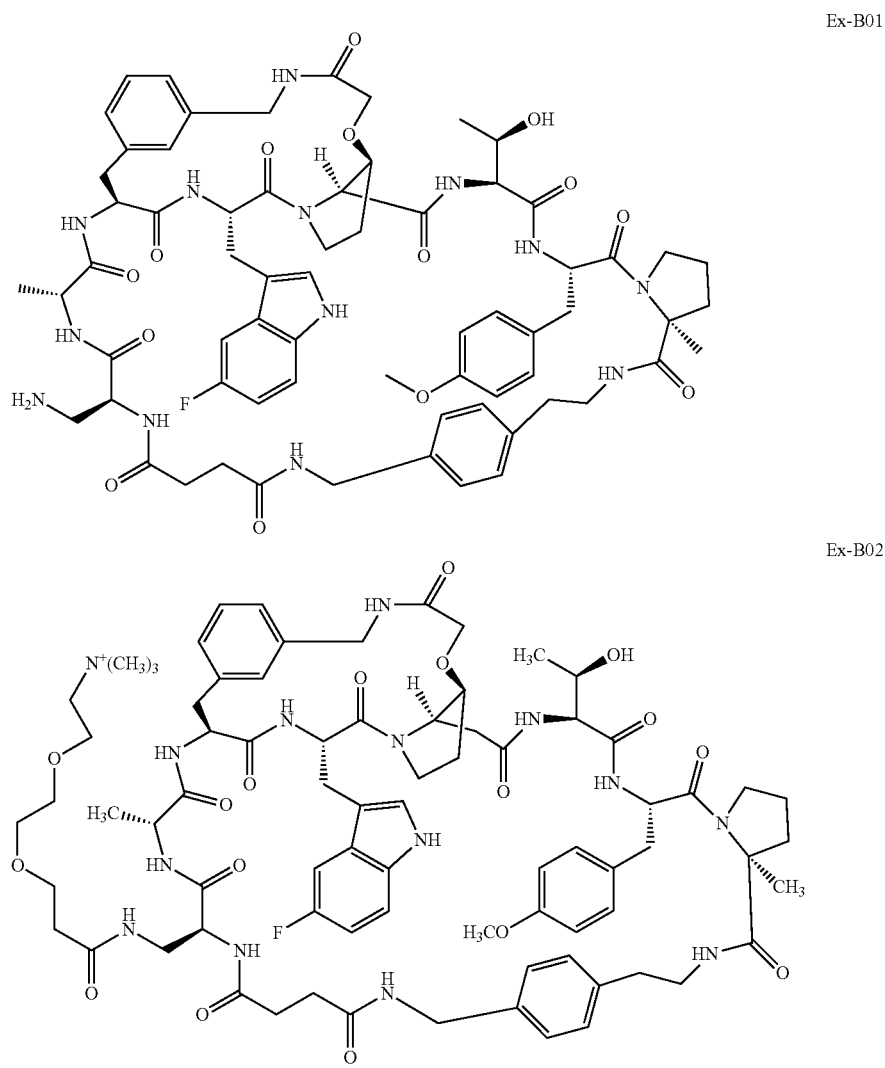

Compounds Ex-B01 and Ex-B02 were prepared from Int. 36 (analogous to intermediate Int 29, described above) in an analogous manner to the preparation of compounds Ex-B03 and Ex-B04 detailed above from Intermediate Int 29 described above. Compound Ex-B02 was prepared from Ex-B01 in an analogous manner to that described above for Ex-B03 and Ex-B04 using intermediate 34, the preparation of which is described below.

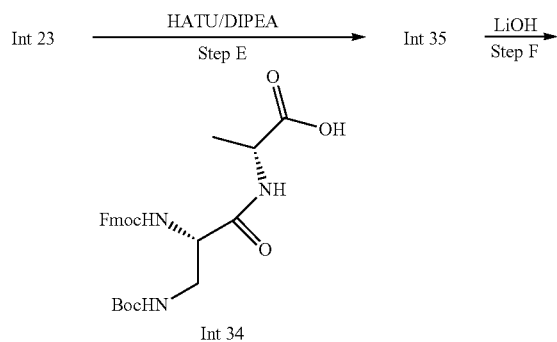

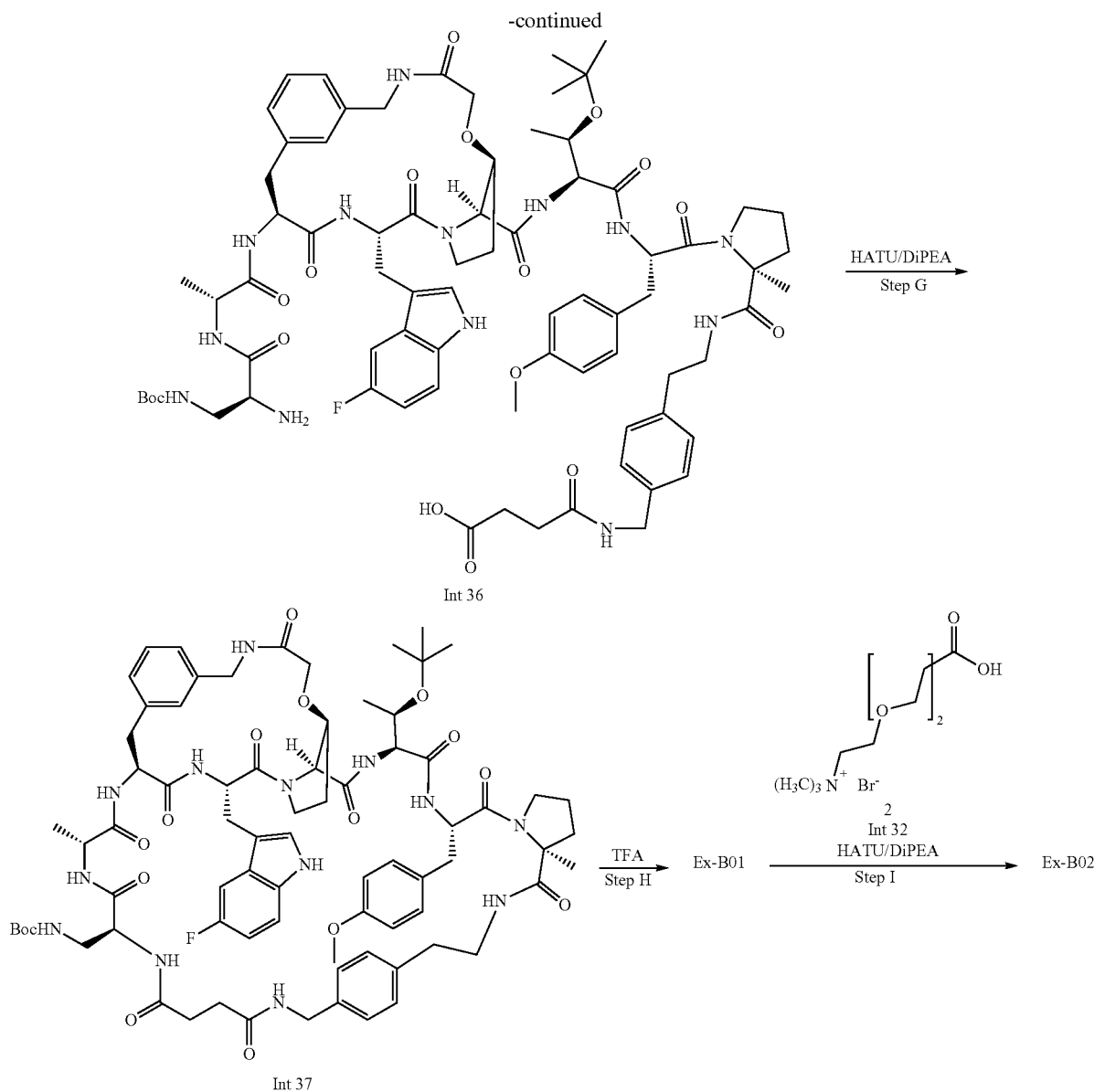

Step E: Synthesis of Intermediate 35

Intermediate 23 (152 mg, 0.122 mmol), DMF (3 ml) and Intermediate 34 (60.8 mg, 0.122 mmol) were stirred in a methanol/ice bath followed by addition of Hunig's Base (0.043 ml, 0.244 mmol) and HATU (48.8 mg, 0.128 mmol) for one hour. The reaction mixture was purified by reverse phase chromatography (C18, 130 g cartridge). The column was eluted by an acetonitrile/water/0.1% v/v formic acid (0% to 100%). Related fractions were pooled and evaporated on a lyophilizer to afford a colorless solid as Int 35. LCMS calc.=1721.82; found=1724.32.

Step F: Synthesis of Intermediate 36

To the solution of 35 (176 mg, 0.102 mmol) in 1,4-dioxane (2 mL) and water (2 ml) at 0° C. was added lithium hydroxide (2M, 0.511 mL, 1.022 mmol) dropwise. The reaction was stirred at room temperature for 1 hour followed addition of HCl (1M, 1.022 mL, 1.022 mmol).

Volatiles were removed under reduced pressure to afford a colorless solid as crude Int 36, which was used as isolated in the following reaction. LCMS calc.=1485.73; found=1488.28.

Step G: Synthesis of Intermediate 37

Intermediate 36 (152 mg, 0.102 mmol), DMF (8 mL) and CH$_2$Cl$_2$ (8 mL) were stirred in a methanol/ice bath followed by addition of Hunig's Base (0.018 mL, 0.102 mmol) and HATU (10.83 mg, 0.028 mmol) for 3 hours. To the reaction mixture was added 5 mL of water and the crude reaction mixture was purified by reverse phase chromatography (C18, 130 g cartridge). The column was eluted by an acetonitrile/water/0.1% v/v formic acid mixture (0% to 100%). Related fractions were pooled to afford a colorless solid as Intermediate 37. LCMS calc.=1467.72; found=1490.26 (M+Na$^+$).

Step H: Synthesis of Compound Ex-B01

Intermediate 37 (89.4 mg, 0.061 mmol), $CH_2Cl_2$ (1.5 mL) and TFA (0.5 mL, 6.49 mmol) were stirred at room temperature for 1 h. Volatiles were removed under reduced pressure. The pot residue was purified by reverse phase chromatography (C18, 130 g cartridge). The column was eluted by an acetonitrile/water/0.1% v/v formic acid mixture (0% to 100%). Related fractions were pooled and evaporated in vacuo to afford Ex-B01. LCMS calc.=1311.61; found=1315.99.

Step I: Synthesis of Compound Ex-B02

Ex-B01 (17.22 mg, 0.013 mmol), Intermediate 32, and DMF (1 mL) were stirred in a methanol/ice bath followed by addition of Hunig's Base (0.018 mL, 0.102 mmol) and HATU (10.83 mg, 0.028 mmol). Aliquot at 1 h indicated completion of reaction. The reaction crude was purified by reverse phase chromatography (C18, 130 g cartridge). The column was eluted by an acetonitrile/water/0.1% v/v formic acid mixture (0% to 65%). Related fractions were pooled to afford Ex-B02. LCMS calc.=1513.75; found=1518.10.

Preparation of Int 34

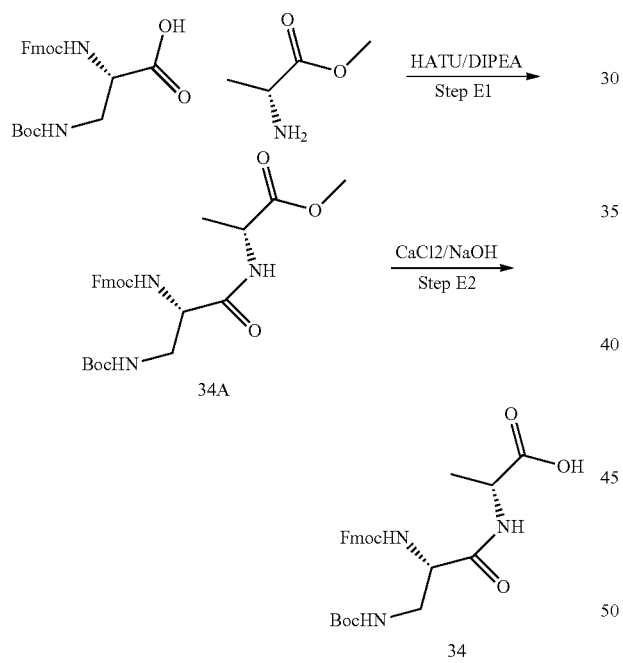

Step E1: Synthesis of Intermediate 34A

To FMOC-DAP(BOC)—OH (500 mg, 1.172 mmol) in DMF (5862 µl) was added D-alanine methyl ester HCl (164 mg, 1.172 mmol), HATU (490 mg, 1.290 mmol) and DIEA (614 µl, 3.52 mmol). The mixture was stirred at rt for 15 h. The reaction crude was purified by reverse phase chromatography (C18, 100 g cartridge). The column was eluted by an acetonitrile/water/0.1% v/v TFA mixture (0% to 80%) to afford I-methyl 2-((S)-2-((((9H-fluoren-9-yl)methoxy)carbonyl)amino)-3-((tert-butoxycarbonyl)amino)propanamido)-propanoate, 34A (495 mg, 0.968 mmol, 83% yield) as a white solid. LCMS calc.=511.56; found=512.26.

Step E2: Synthesis of Intermediate 34

NaOH (46.4 mg, 1.161 mmol) was added to a stirred mixture of I-methyl 2-((S)-2-((((9H-fluoren-9-yl)methoxy)carbonyl)amino)-3-((tert-butoxycarbonyl)amino)propanamido)-propanoate, 34A (495 mg, 0.968 mmol) in 0.8 M aq: $CaCl_2$ (1.210 ml, 0.968 mmol) and 2-Propanol (15 ml)/Water (5 ml). The mixture was stirred at room temperature overnight. The reaction crude was purified by reverse phase chromatography (C18, 100 g cartridge). The column was eluted by an acetonitrile/water/0.1% v/v TFA mixture (0% to 80%) to afford I-2-((S)-2-((((9H-fluoren-9-yl)methoxy)carbonyl)amino)3-((tert-butoxycarbonyl)amino)-propanamido) propanoic acid, Int 34. LCMS calc.=497.54; found=499.23.

Example 4 Preparation of Ex-C03 and Ex-C04

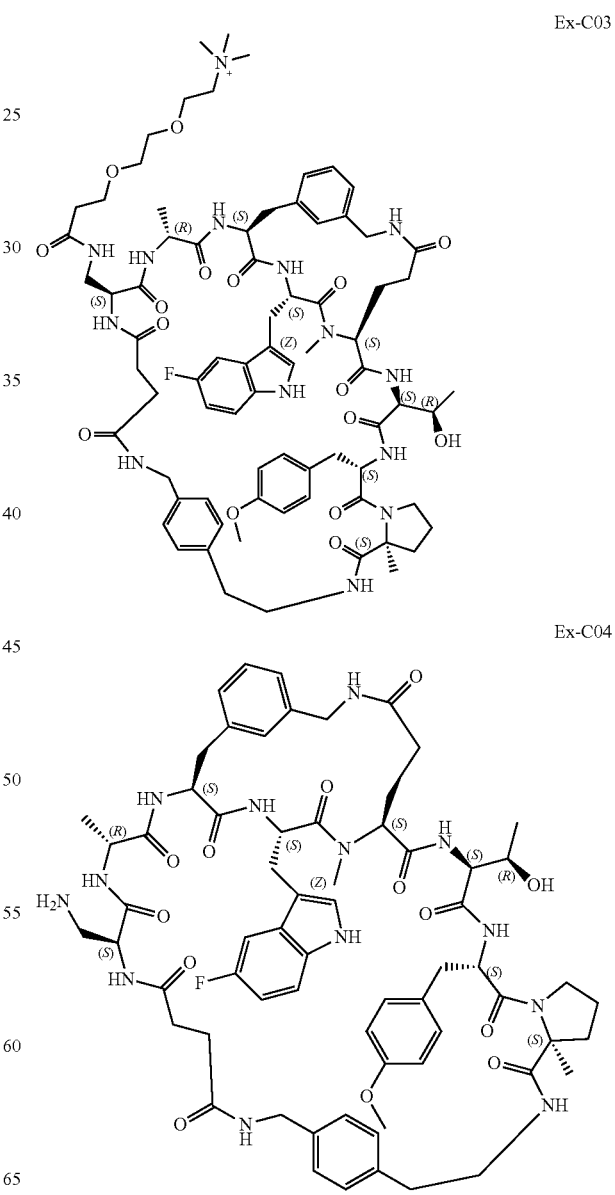

Compounds Ex-C03 and Ex-C04 were prepared in accordance with the following schemes in a manner analogous to the above-described example compounds using and intermediate Int 49 analogous to intermediate Int 10 described above:

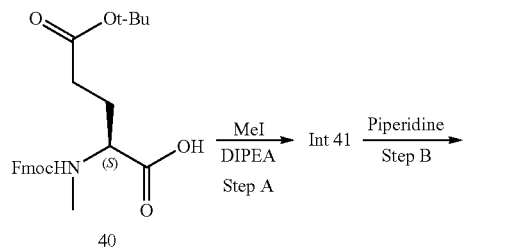

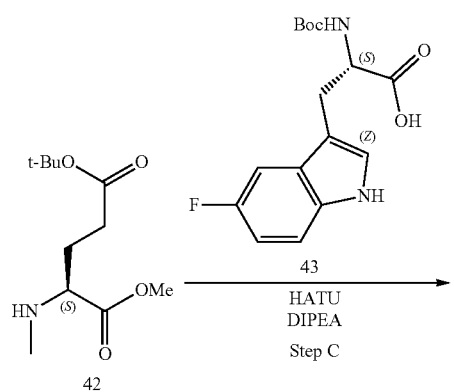

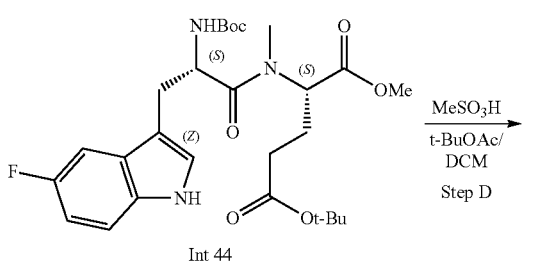

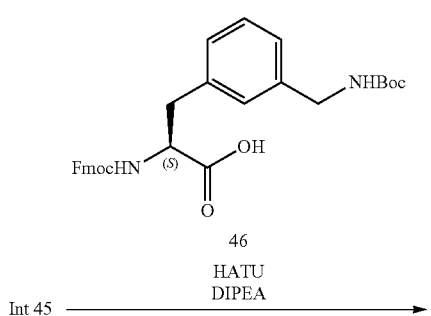

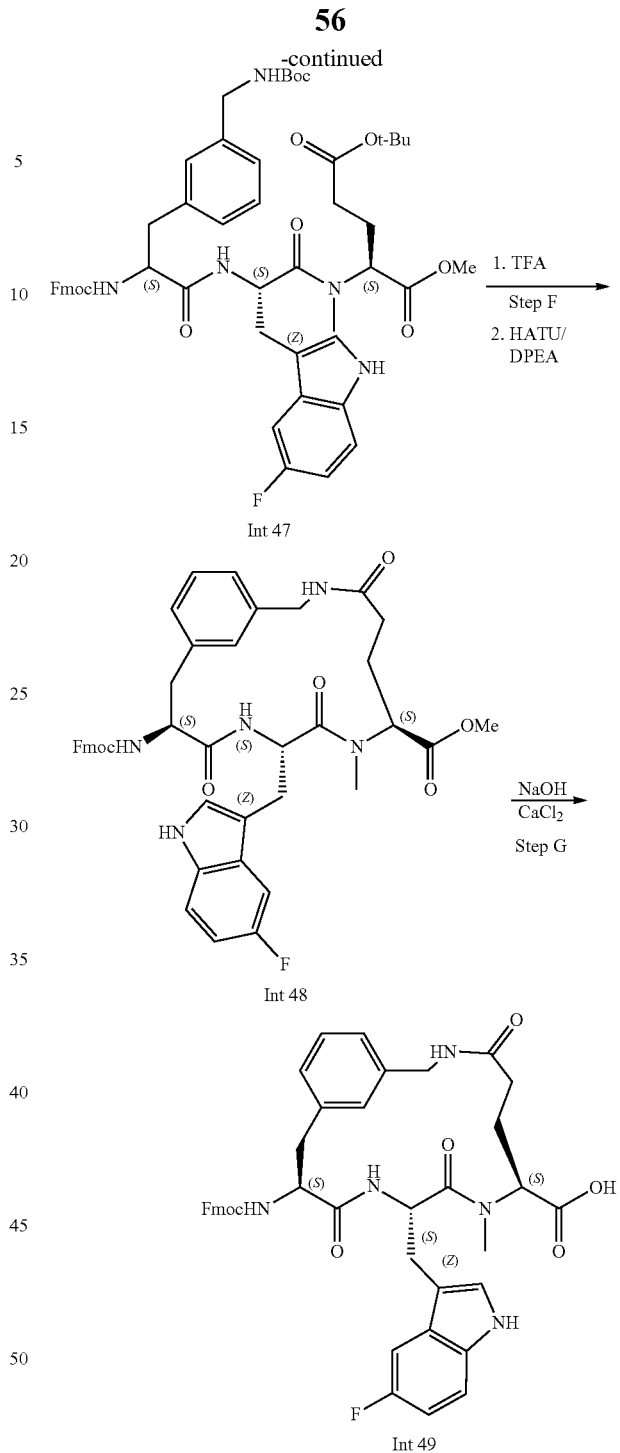

Step A—Synthesis of Intermediate 41

To a solution of 40 (5.0 g, 11.38 mmol) and DIPEA (3.97 mL, 22.75 mmol) in acetone (25 mL) was added methyl iodide (1.423 mL, 22.75 mmol) and the reaction mixture was stirred at room temperature overnight. Upon stirring overnight, some precipitation was observed and the solids were filtered and triturated with acetone. The combined organic fractions were concentrated in vacuo. The residue was purified by column chromatography over silica gel (Isco 120 g), eluting with 0-40% EtOAc/hexanes to give Intermediate 41. UPLC Method A: tR=1.50 min; [M+23]+=476.37.

Step B—Synthesis of Intermediate 42

To a solution of Intermediate 41 (5.04 g, 11.11 mmol) in DCM (25 mL) was added piperidine (3.30 mL, 33.3 mmol) and the mixture was stirred at room temperature for 4 h. The reaction mixture was concentrated in vacuo and the residue was purified by column chromatography over silica gel (Isco 220 g), eluting with 0-40-100% EtOAc/hexanes to yield intermediate 42. UPLC Method A: tR=0.59 min; [M+1]+=232.19.

Step C—Synthesis of Intermediate 44

To a solution of intermediate 42 (20 mg, 0.062 mmol), DIPEA (0.033 mL, 0.186 mmol) and 43 (15.79 mg, 0.068 mmol) in DCM (1 mL) was added HATU (26.0 mg, 0.068 mmol) and the mixture was stirred at room temperature for 90 min. The mixture was quenched by the addition of water and extracted with EtOAc. The combined organic fractions were washed with brine, dried over $Na_2SO_4$, filtered and concentrated in vacuo. The residue was purified by column chromatography on silica gel (Isco 4 g), eluting with 0-50% EtOAc/isohexane to give intermediate 44. UPLC Method A: tR=1.34 min; [M+1]+=536.41.

Step D—Synthesis of Intermediate 45

To a solution of intermediate 44 (1.0 g, 1.867 mmol) in a 4:1 t-BuOAc/DCM (10 mL) was added methanesulfonic acid (0.485 mL, 7.47 mmol) and the mixture was stirred at room temperature for 3 h. After completion, the reaction mixture was concentrated to half its volume and the crude mixture was used a such for the next step without any purification. UPLC Method A: tR=0.92 min; [M+1]+=436.23.

Step E—Synthesis of Intermediate 47

To a stirred mixture of 46 (1.929 g, 3.73 mmol) and DIPEA (1.956 mL, 11.20 mmol) in DCM (20 mL) was added HATU (1.420 g, 3.73 mmol) and the mixture was stirred at room temperature for 10 min. This mixture was added to a stirred solution of intermediate 45 (0.813 g, 1.867 mmol) in 2 mL DCM and the reaction was stirred at rt for 1 h. The reaction mixture was quenched by the addition of sat. $NaHCO_3$ and extracted with DCM. The combined organic fractions were washed with brine, dried over $Na_2SO_4$, filtered and concentrated in vacuo. The residue was purified by column chromatography on silica gel (Isco 120 g), eluting with 0-25% EtOAc:EtOH (3:1)/hexanes to give intermediate 47 as a yellow oil. UPLC Method C: tR=1.60 min; [M+1]+=934.36.

Step F—Synthesis of Intermediate 48

To a stirred solution of intermediate 47 (1.10 g, 1.178 mmol) in DCM (15 mL) was added TFA (2.72 mL, 35.3 mmol) and the reaction mixture was stirred at room temperature for 2 h. The excess TFA was concentrated in vacuo and diluted with 4 N HCl in 1,4-dioxane. The residue was left to stir for 5 min, concentrated in vacuo and dried which was then diluted with DMF (5 mL). To this mixture was added HATU (537 mg, 1.413 mmol) and the mixture was stirred at room temperature for 15 min followed by dilution with DCM (50 mL). DIPEA (1.028 mL, 5.89 mmol) was added and the reaction was stirred at room temperature for 3 h. The reaction mixture was quenched by the addition of sat. $NaHCO_3$ and extracted with DCM. The combined organic fractions were washed with brine, dried over $Na_2SO_4$, filtered and concentrated in vacuo. The residue was purified by column chromatography on silica gel (Isco 40 g), eluting with 0-40-50% EtOAc:EtOH (3:1)/hexanes to give intermediate 48 as a yellow gum. UPLC Method C: tR=1.26 min; [M+1]+=760.26.

Step G—Synthesis of Intermediate 49

To a solution of intermediate 48 (150 mg, 0.197 mmol) and 0.8 M $CaCl_2$ (0.987 mL, 0.790 mmol) in 7:3 i-PrOH: $H_2O$ (1.5 mL) was added NaOH (9.48 mg, 0.237 mmol) and the reaction was stirred at room temperature for 2 h. The reaction mixture was quenched by the addition of 1 N HCl until pH 6 and extracted with EtOAc. The combined organic fractions were washed with brine, dried over $Na_2SO_4$, filtered and concentrated in vacuo. The product was used as such for the next step without further purification. UPLC Method C: tR=1.21 min; [M+1]+=746.12.

Compounds Ex-C03 and Ex-C04 were prepared in accordance with the following scheme:

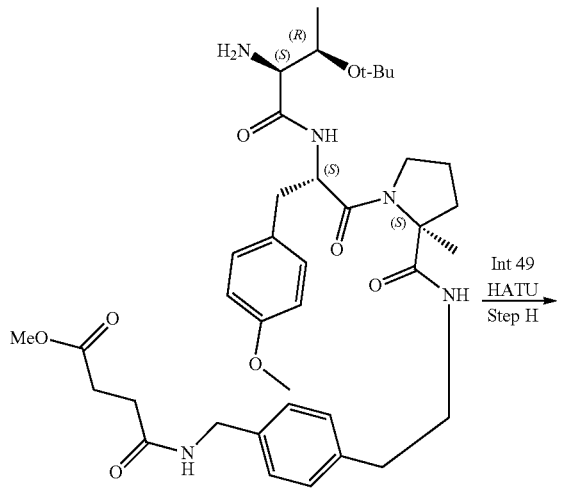

20

-continued
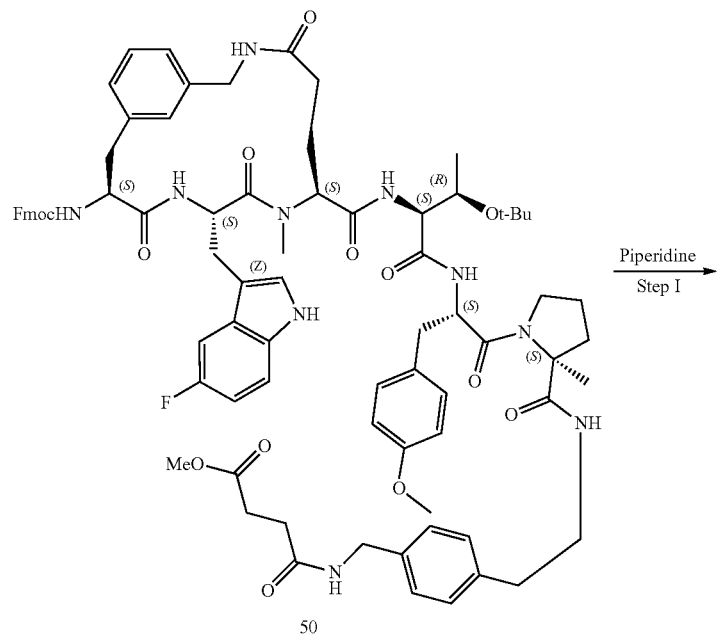
50
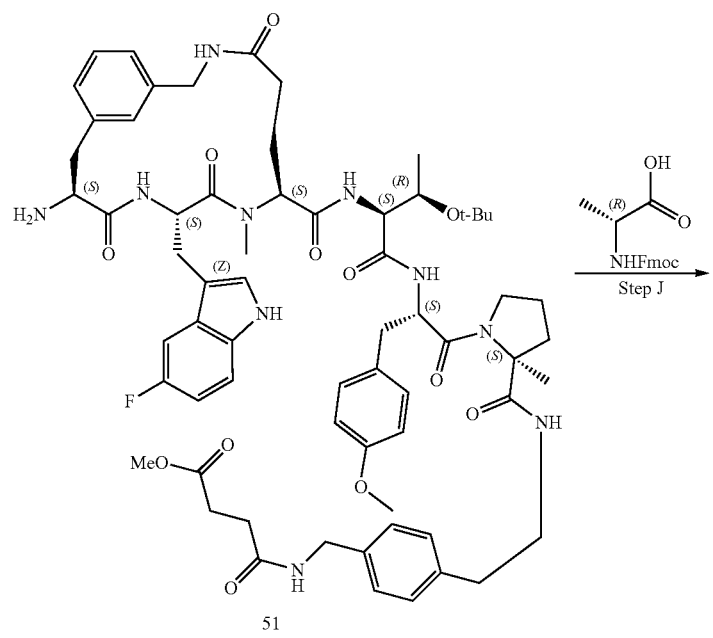
51

-continued
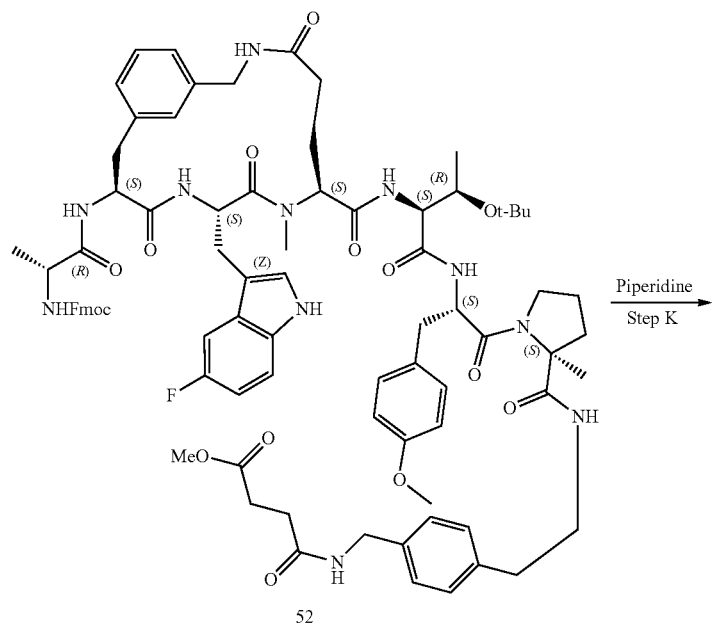
52
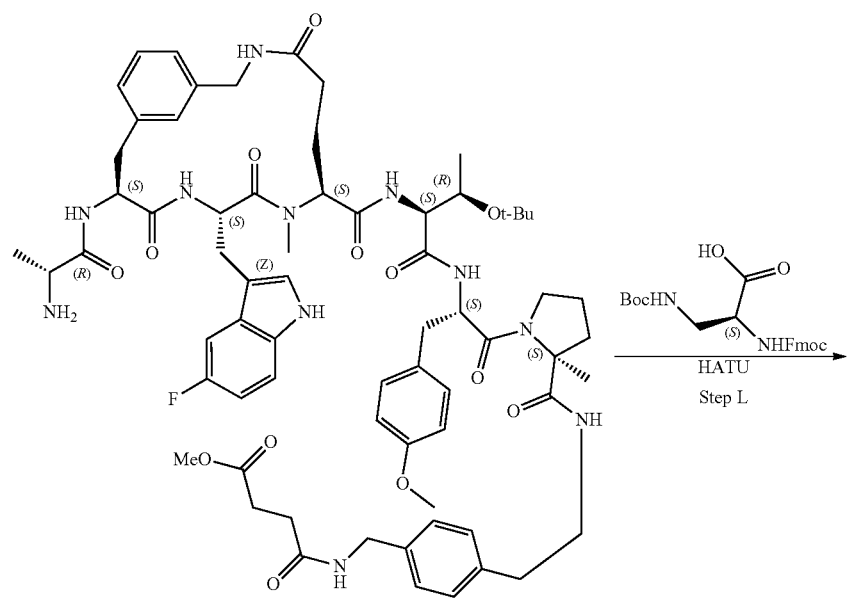
53

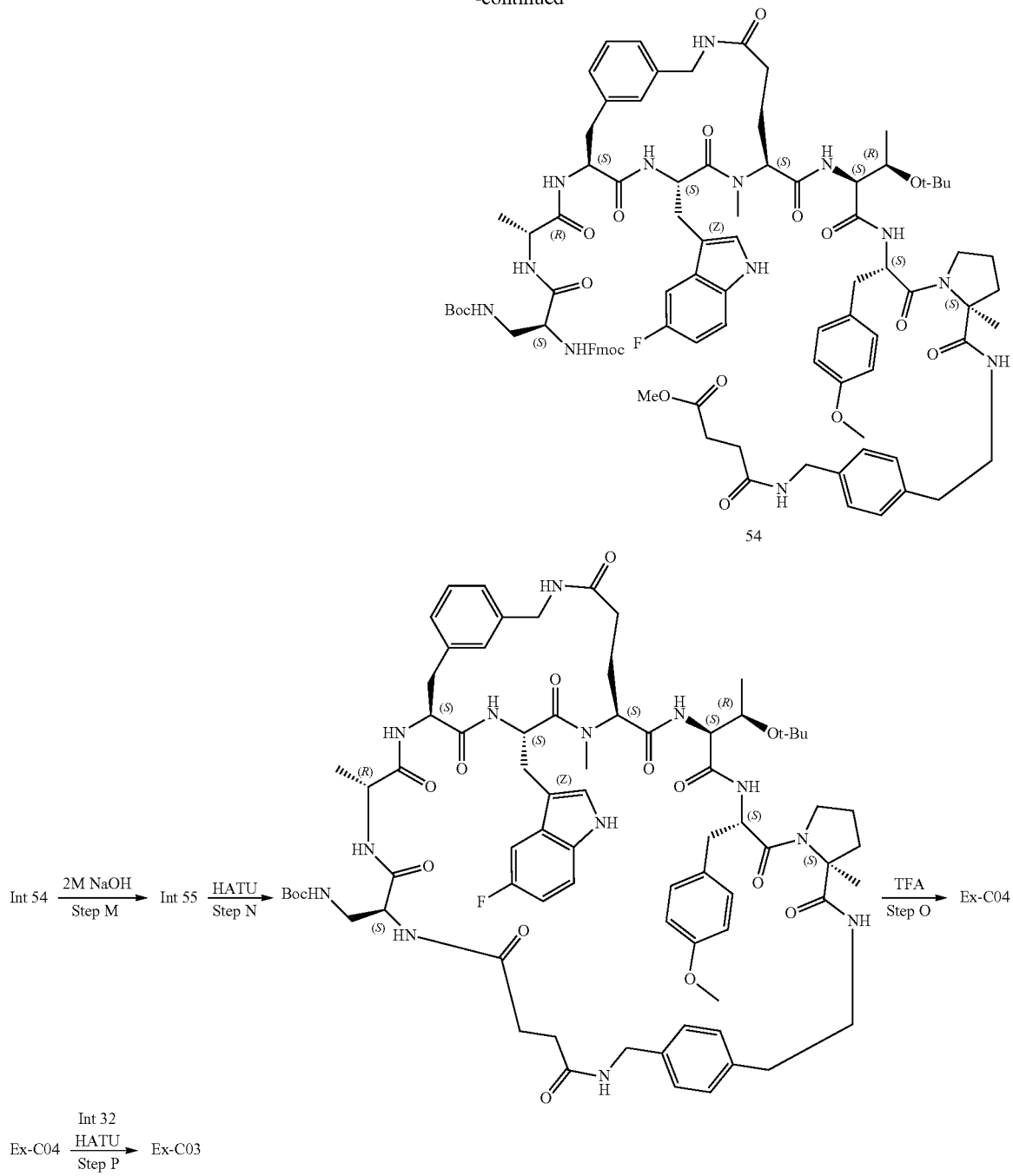

Step H—Synthesis of Intermediate 50

To a solution of intermediate 49 (250 mg, 0.335 mmol), intermediate 20 (238 mg, 0.335 mmol) and DIPEA (0.176 mL, 1.006 mmol) was added HATU (140 mg, 0.369 mmol) and the reaction was stirred at room temperature for 2 h. The reaction mixture was quenched by the addition of sat. NaHCO$_3$ and extracted with DCM. The combined organic fractions were washed with brine, dried over Na$_2$SO$_4$, filtered and concentrated in vacuo. The residue was purified by column chromatography on silica gel (Isco 40 g), eluting with 0-40-60-80-100% EtOAc:EtOH (3:1)/hexanes to give intermediate 50 as a white solid. UPLC Method C: tR=1.40 min; [M+1]+=1437.53.

Step I— Synthesis of Intermediate 51

To a solution of intermediate 50 (235 mg, 0.163 mmol) in CH$_3$CN (1 mL) was added piperidine (0.081 mL, 0.817 mmol) and the reaction mixture was stirred at room temperature for 2 h. The mixture was concentrated in vacuo and dried. The product was used as such without further purification. UPLC Method C: tR=1.02 min; [M+1]+=1215.52.

Step J—Synthesis of Intermediate 52

To a solution of Fmoc-D-Ala-OH (53.5 mg, 0.172 mmol) and DIPEA (0.086 mL, 0.491 mmol) in DCM (2 mL) was added HATU (68.5 mg, 0.180 mmol) and the mixture was stirred at room temperature for 15 min. followed by the addition of intermediate 51 (199 mg, 0.164 mmol) in 2 mL DCM and was stirred for 2 h. The reaction mixture was quenched by the addition of sat. NaHCO$_3$ and extracted with DCM. The combined organic fractions were washed with brine, dried over Na$_2$SO$_4$, filtered and concentrated in vacuo. The residue was purified by column chromatography on silica gel (Isco 24 g), eluting with 0-40-60% EtOAc:EtOH (3:1)/hexanes to give intermediate 52 as a colorless oil. UPLC Method C: tR=1.39 min; [M+1]+=1509.7.

Step K—Synthesis of Intermediate 53

To a solution of intermediate 52 (207 mg, 0.137 mmol) in CH$_3$CN (2 mL) was added piperidine (0.082 mL, 0.823 mmol) and the reaction mixture was stirred at room temperature for 2 h. The mixture was concentrated in vacuo and dried. The product was used as such without further purification. UPLC Method A: tR=1.01 min; [M/2+1]+=643.97.

Step L—Synthesis of Intermediate 54

To a solution of Fmoc-DAP(Boc)-OH (53.7 mg, 0.126 mmol) and DIPEA (0.066 mL, 0.378 mmol) in DCM (2 mL) was added HATU (52.7 mg, 0.139 mmol) and the mixture was stirred at room temperature for 15 min. followed by the addition of intermediate 53 (162 mg, 0.126 mmol) in 2 mL DCM and was stirred for 2 h. The reaction mixture was quenched by the addition of sat. NaHCO$_3$ and extracted with DCM. The combined organic fractions were washed with brine, dried over Na$_2$SO$_4$, filtered and concentrated in vacuo. The residue was purified by column chromatography on silica gel (Isco 24 g), eluting with 0-40-50-80-100% EtOAc:EtOH (3:1)/hexanes to give intermediate 54 as an off-white gum. UPLC Method A: tR=1.41 min; [M/2+1]+=848.69.

Step M—Synthesis of Intermediate 55

To a solution of intermediate 54 (23 mg, 0.014 mmol) in 2-propanol (3 mL) was added 2 N NaOH (0.068 mL, 0.136 mmol) and stirred for 2 h at 0° C. The mixture was purified by column chromatography over C18 (eluting with acetonitrile+0.05% TFA/water+0.05% TFA 20:80 to 100:0) to give intermediate 55 as a white solid after lyophilization. UPLC Method A: tR=1.04 min; [M/2+1]+=730.30.

Step N—Synthesis of Intermediate 56

To a solution of intermediate 55 (10 mg, 6.86 µmol) in DMF (1 mL) was added HATU (2.87 mg, 7.54 µmol) and the reaction was stirred at 0° C. for 15 followed by dilution with DCM (30 mL). DIPEA (5.99 µL, 0.034 mmol) was added and the reaction was stirred at room temperature for 2 h. The residue was purified by column chromatography over C18 (eluting with acetonitrile+0.05% TFA/water+0.05% TFA 20:80 to 100:0) to give intermediate 55 as a white solid after lyophilization. UPLC Method A: tR=1.19 min; [M/2+1]+=721.27.

Step O—Synthesis of Ex-C04

To a solution of intermediate 56 (9 mg, 6.25 µmol) in DCM (2 mL) was added 4.0 M HCl in 1,4-dioxane (0.156 mL, 0.625 mmol) and the mixture was stirred at room temperature for 3 h. The excess reagent was concentrated in vacuo and dried to yield Ex-C04. The product was used as such for the next step without further purification. UPLC Method A: tR=0.84 min; [M/2+1]+=643.19.

Step P—Synthesis of Ex-C03

To a solution of intermediate 32 (2.162 mg, 6.23 µmol) and DIPEA (6.53 µL, 0.037 mmol) in DCM (5 mL) was added HATU (2.61 mg, 6.85 µmol) and the mixture was stirred at room temperature for 15 min. followed by the addition of Compound 58 (8.0 mg, 6.23 µmol) in 2 mL DCM. The reaction was stirred at 0° C. for 2 h. The residue was purified by column chromatography over C18 (eluting with acetonitrile+0.05% TFA/water+0.05% TFA 20:80 to 100:0) to yield Ex-C03 after lyophilization. UPLC Method A: tR=0.85 min; [M/2+1]+=743.75.

Example 5

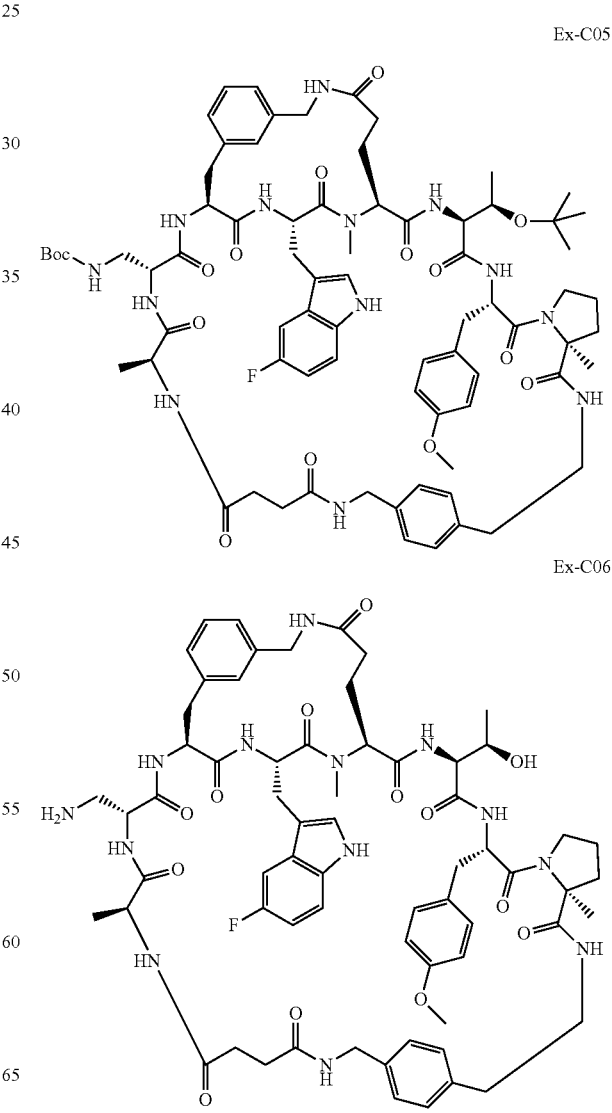

Ex-C05

Ex-C06

Ex-C07
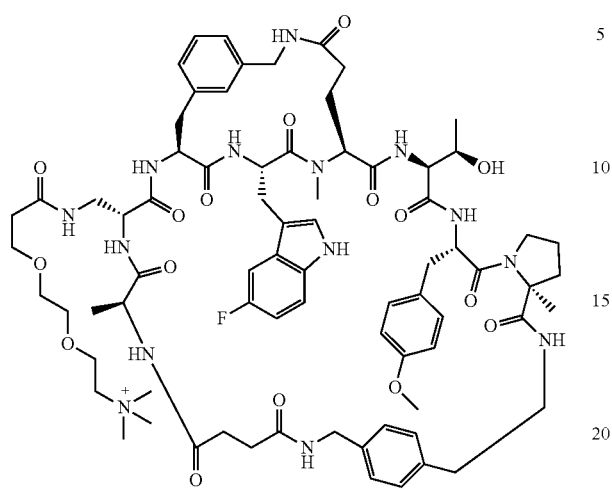
Compounds Ex-C05, Ex-C06 and Ex-C07 were prepared in accordance with the following schemes in a manner analogous to the above-described example compounds from intermediate Int 53, prepared above, in accordance with the following scheme:
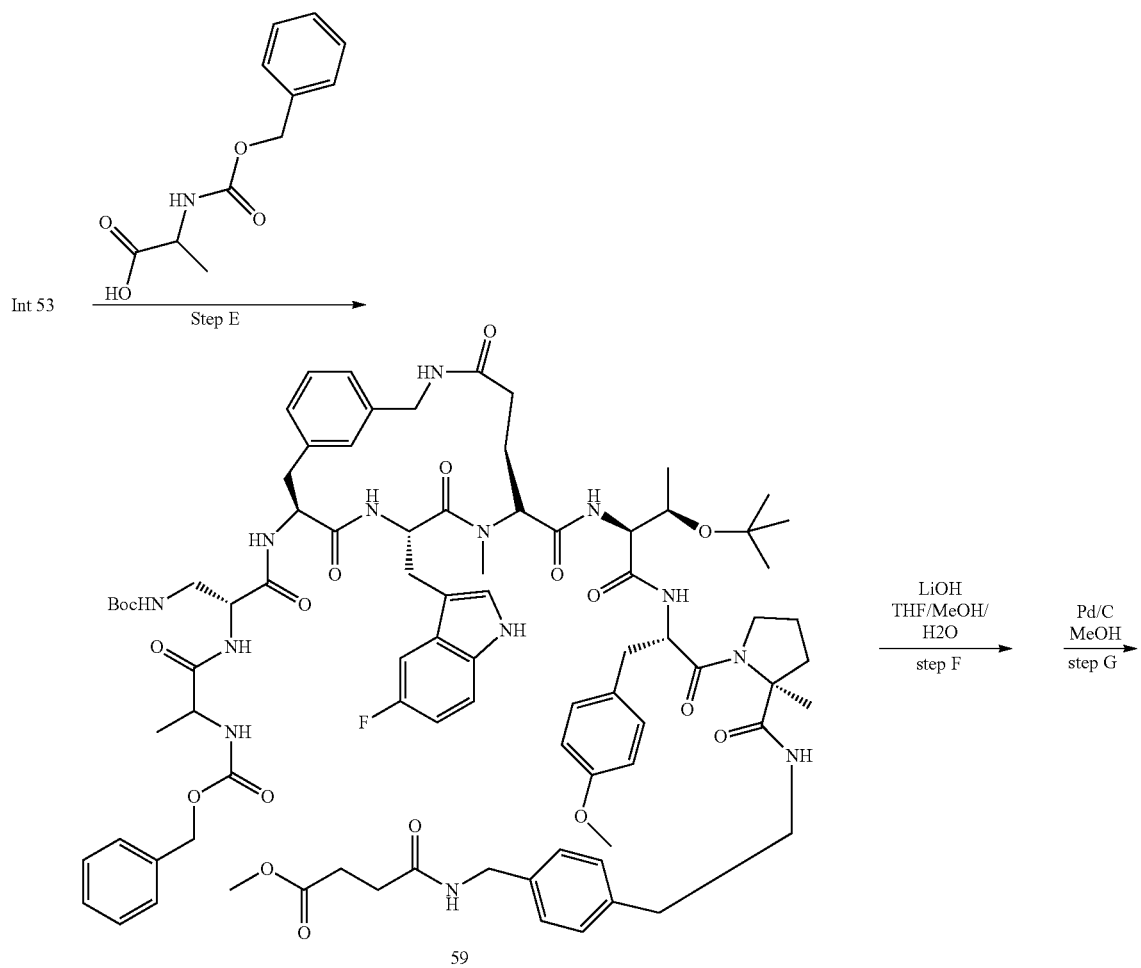

-continued
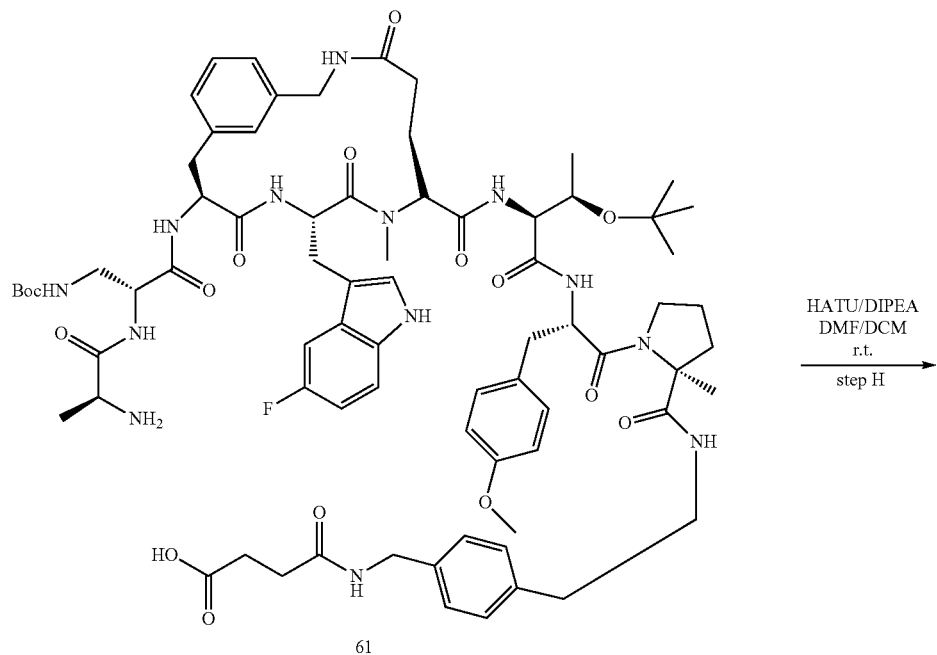
61
HATU/DIPEA
DMF/DCM
r.t.
step H
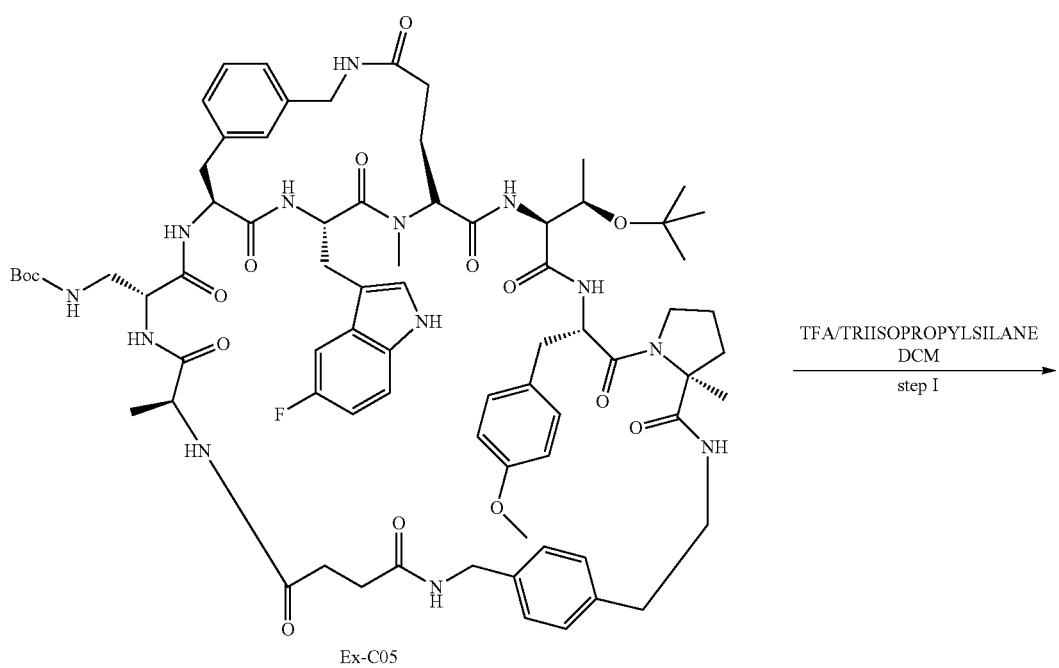
Ex-C05
TFA/TRIISOPROPYLSILANE
DCM
step I

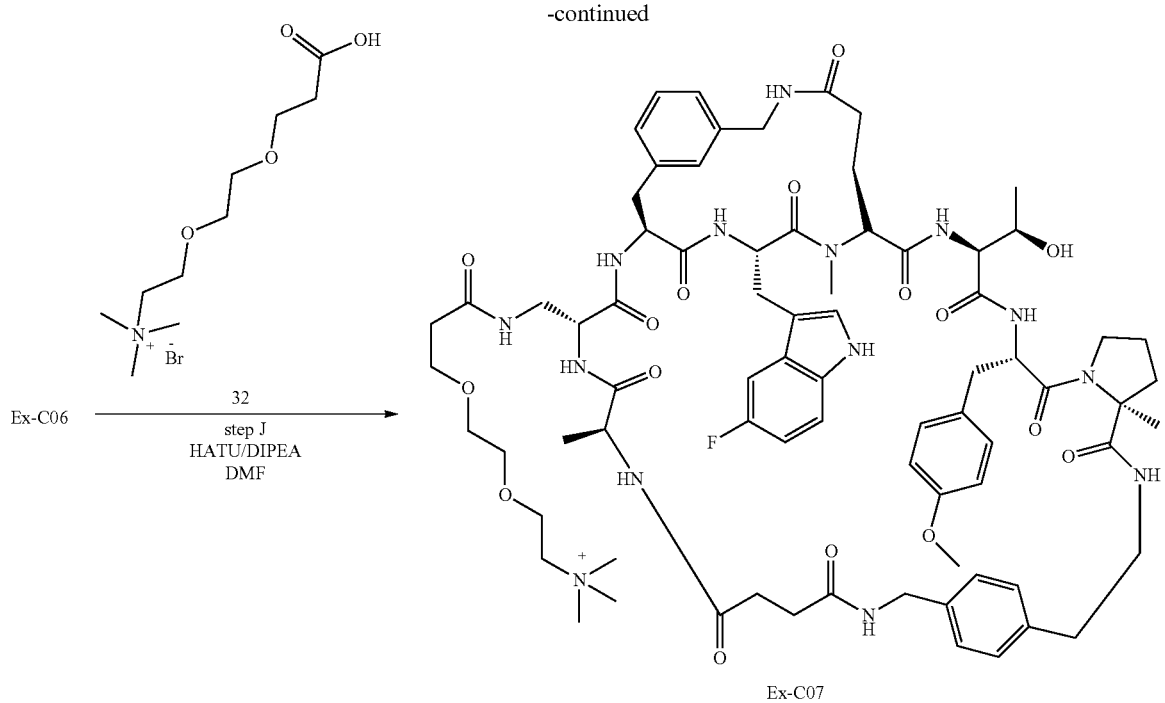

Step E—Synthesis of Intermediate 59

To the solution of 53 (112 mg, 0.080 mmol) and (S)-2-(((benzyloxy)carbonyl)amino)-propanoic acid (25.7 mg, 0.115 mmol) in DMF (2 ml) was added HATU (42.6 mg, 0.112 mmol) and DIPEA (0.042 ml, 0.240 mmol). The resulting solution was stirred at ambient temperature for 2 hours, the reaction mixture was purified on reverse phase MPLC (150 g C18 column), eluting with Acetonitrile/Water+0.05% TFA (10-100% Acetonitrile in water) to give Int 59. LCMS anal. Calcd. For C84H108FN13O18: 1605.79; Found: 1607.31 (M+1)$^+$, 803.73 (M+2)$^{2+}$.

Step F—Synthesis of Intermediate 60

To a solution of 59 (0.124 g, 0.077 mmol) in a mixture solvent of THF (5 ml), MeOH (1.6 ml) and Water (1.6 ml) at 0° C. was added lithium hydroxide (0.4 ml, 0.400 mmol) dropwise, and the resulting solution was stirred at 0° C. for 2 hours. Reaction mixture volatiles were evaporated on rotary evaporator and the aqueous residue was acidified to pH 4 at 0° C., then extracted with 30% IPA/DCM (3×100 mL), the combined organic phase was dried over Na$_2$SO$_4$, concentrated, and the residue was purified on reverse phase MPLC (150 g C18 column), eluting with Acetonitrile/Water+0.05% TFA (10-100% Acetonitrile in water) to give Int 60. LCMS anal. Calcd. For C83H106FN13O18: 1591.78; Found: 1593.18 (M+1)$^+$, 797.04 (M+2)$^{2+}$.

Step G—Synthesis of Intermediate 61

To a solution of 60 (70 mg, 0.044 mmol) in MeOH (4 ml) was added Pd/C (10 mg, 9.40 μmol), the resulting mixture was hydrogenated for 1 hour at room temperature using a hydrogen balloon. The mixture was filtered through celite, washed with MeOH (3×50 ml), and the filtrate concentrated, then dissolved in acetonitrile (10 mL) and water (6.5 mL). The resulting solution was cooled to 0° C. and HCl (0.659 ml, 0.066 mmol) was added dropwise, with stirring. The resulting solution was stirred at 0° C. for 3 min, then lyophized to give product Int 61. LCMS anal. Calcd. For C75H100FN13O16: 1457.74; Found: 1459.05 (M+1)$^+$, 730.04 (M+2)$^{2+}$.

Step H—Synthesis of Ex-C05

To the solution of 61 (59.1 mg, 0.040 mmol) in DMF (5 ml) at r.t. was added HATU (18.04 mg, 0.047 mmol), the resulting solution was stirred at r.t. for 20 min, then added CH$_2$Cl$_2$ (140 ml) followed by addition of DIPEA (0.021 ml, 0.119 mmol), the resulting solution was stirred at ambient temperature for 0.5 h. Volatiles were removed under reduced pressure, and the resulting DMF solution was purified on reverse phase MPLC (130 g C18 column), eluting with Acetonitrile/Water+0.05% TFA (5-80% Acetonitrile in water) to give Ex-C05. LCMS anal. Calcd. For C75H98FN13O15: 1439.73; Found: 1440.49 (M+1)$^+$, 720.89 (M+2)$^{2+}$.

Step I—Synthesis of Ex-C06

To the solution of Ex-C05 (0.0295 g, 0.020 mmol) in CH$_2$Cl$_2$ (1.5 ml) at r.t. was added triisopropylsilane (0.025 mL, 0.123 mmol) and TFA (2.3 ml, 29.9 mmol), the resulting solution was stirred at rt for 0.5 h, then the solution was concentrated under reduced pressure and the residue was dissolved in DCM (1.5 mL) and treated with HCl (4N in Dioxane) (0.28 mL, 1.120 mmol), concentrated, and the residue was further dried under high vacuum overnight to give Ex-C06. The crude product was purified by preparative HPLC reverse phase (SunFire C-18, 19×150 mm), eluting with Acetonitrile/Water+0.1% formic acid (2-50% Acetonitrile in water). LCMS anal. Calcd. For C66H82FN13O13: 1283.61; Found: 1284.46 (M+1)$^+$, 642.79 (M+2)$^{2+}$.

Step J—Synthesis of Ex-07

To the solution of Ex-06 (26.4 mg, 0.02 mmol) and 2-(2-(2-carboxyethoxy)ethoxy)-N,N,N-trimethyl-ethanaminium bromide (32) (7.20 mg, 0.024 mmol) in DMF (2 ml) was added HATU (9.13 mg, 0.024 mmol) and DIPEA (10.48 µl, 0.060 mmol), the resulting solution was stirred at r.t. for 0.5 h, LCMS showed the reaction completed. The DMF solution was purified by preparative HPLC reverse phase (SunFire C-18, 19×150 mm), eluting with Acetonitrile/Water+0.1% formic acid (2-45% Acetonitrile in water) to yield Ex-07. LCMS anal. Calcd. For C76H102FN14O16+: 1485.76; Found: 1485.37 M+, 743.45 $(M+1)^{2+}$

Example 9: Preparation of Ex-OT-03 and Ex-OT-04

Ex-OT-03

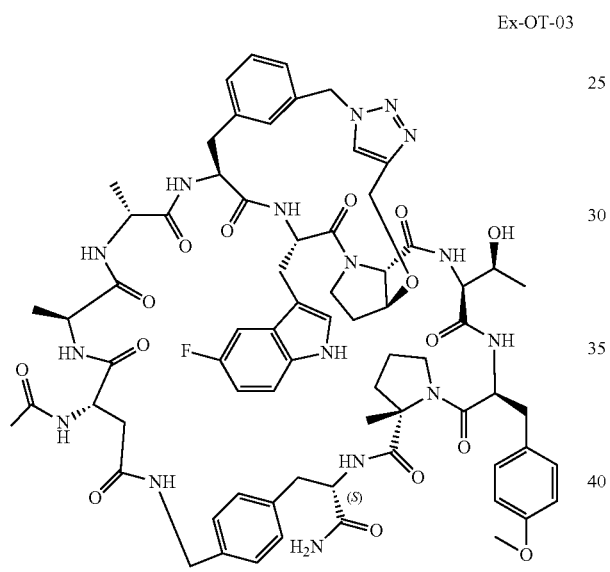

Ex-OT-04

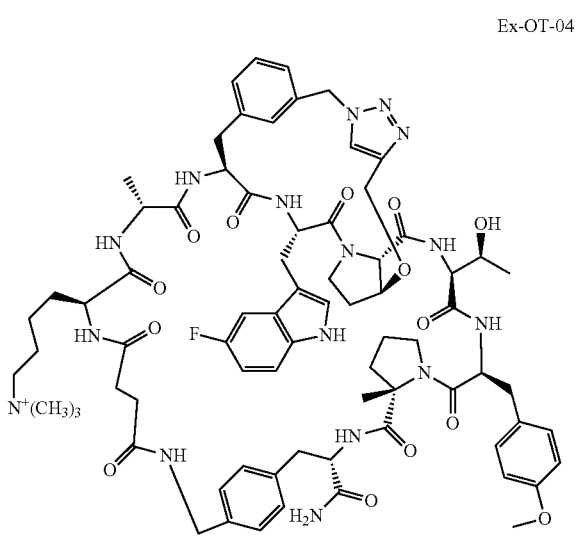

Intermediate 122

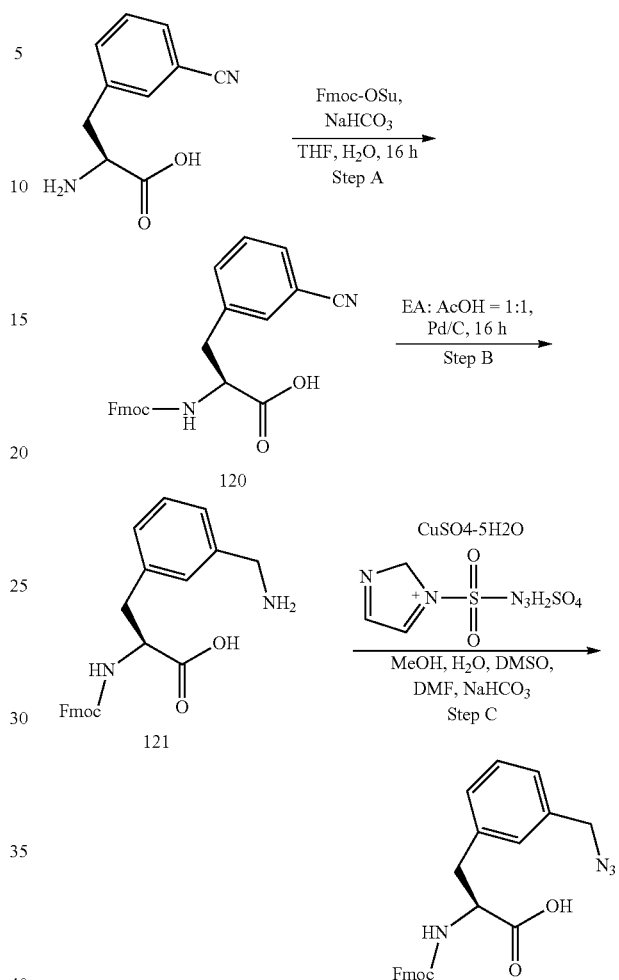

Step A: Synthesis of Intermediate 120

To a solution of (S)-2-amino-3-(3-cyanophenyl)propanoic acid (2.00 g, 10.52 mmol) in THF (20 mL) and water (20 mL) was added NaHCO3 (2.65 g, 31.5 mmol) at 25° C. under nitrogen atmosphere. After Fmoc-OSu (3.90 g, 11.6 mmol) was added at 0° C., the reaction mixture was stirred at 25° C. for 16 h. The pH value of the reaction solution was adjusted to 4-5 with aqueous HCl (2 N). The aqueous phase was extracted with EA (2×200 mL). The combined organic layer was washed with brine (50 mL), dried over anhydrous Na2SO4 and filtered. The filtrate was concentrated under reduced pressure. The residue was purified by silica gel column chromatography, eluted with 0~2% MeOH in DCM to afford 5.20 g (90% yield) of 120 as an off-white solid. LCMS (ESI) calc'd for $C_{25}H_{20}N_2O_4$ $[M+H]^+$: 413.1, found 413.2; $^1$H NMR (300 MHz, CDCl3) δ 7.78 (d, J=7.6 Hz, 2H), 7.57-7.55 (m, 3H), 7.46-7.30 (m, 7H), 5.26 (d, J=7.7 Hz, 1H), 4.72-4.70 (m, 1H), 4.54-4.38 (m, 2H), 4.20 (t, J=6.8 Hz, 1H), 3.28-3.22 (m, 1H), 3.16-3.11 (m, 1H).

Step B: Synthesis of Intermediate 121

To a stirred solution of 120 (2.00 g, 3.64 mmol) in ETOAc (20 mL) and AcOH (20 mL) was added Pd—C (0.387 g, 0.364 mmol, dry) at 25° C. under nitrogen atmosphere. The reaction mixture was degassed with hydrogen for 3 times and stirred at 25° C. for 16 h under 2 atm. The solid was filtered out. The filtrate was concentrated under reduced pressure to afford a yellow solid. The crude product was washed with EA (80 mL) to afford 1.80 g (59% yield) of 121. LCMS (ESI) calc'd for $C_{25}H_{24}N_2O_4$ [M+H]$^+$: 417.2, found 417.2; $^1$H NMR (400 MHz, DMSO-d$^6$) δ 7.85 (d, J=7.7 Hz, 2H), 7.67-7.58 (m, 2H), 7.41-7.20 (m, 8H), 4.26-4.03 (m, 4H), 3.96-3.93 (m, 2H), 3.06 (dd, J=14.0, 4.7 Hz, 1H), 2.88 (dd, J=14.0, 10.5 Hz, 1H).

Step C: Synthesis of Intermediate 122

Intermediate 121 (12.0 g, 14.41 mmol) was dissolved in MeOH (240 mL) and water (60 mL) at 25° C. The pH value of the solution was adjusted to 9 with NaHCO$_3$ powder. To the reaction mixture were added sulfuric acid, 1-(azidosulfonyl)-2H-imidazol-1-ium salt (4.71 g, 17.29 mmol), copper (II) sulfate pentahydrate (0.719 g, 2.88 mmol), DMF (150 mL) and DMSO (60 mL) at 25° C. The pH value of the reaction mixture was adjusted to 9 with NaHCO$_3$ powder. The reaction mixture was stirred at 25° C. for 16 h. The pH value of the reaction mixture was adjusted to 3 with aqueous HCl (1 N). The reaction solution was diluted with water (200 mL). The aqueous phase was extracted with EA (2×500 mL). The combined organic layer was washed with brine (3×100 mL), dried over anhydrous Na$_2$SO$_4$ and filtered. The filtrate was concentrated under reduced pressure. The residue was purified by Prep-HPLC with following condition: Column, Xbridge C$^{18}$, 330 g; mobile phase: ACN in water (0.05% TFA), 30%-75% in 45 min; Detector, UV 254 nm. RT: 38 min. The fractions containing the desired product were combined and concentrated under reduced pressure to afford 6.44 g (95% yield) of 122 as an off-white solid. LCMS (ESI) calc'd for $C_{25}H_{22}N_4O_4$ [M+H]$^+$: 443.2, found 443.3; $^1$H NMR (300 MHz, DMSO-d$^6$) δ 7.88 (d, J=7.5 Hz, 2H), 7.76 (d, J=8.4 Hz, 1H), 7.67-7.63 (m, 2H), 7.43-7.38 (m, 2H), 7.31-7.20 (m, 6H), 4.40 (s, 2H), 4.22-4.19 (m, 4H), 3.10 (dd, J=13.8, 4.4 Hz, 1H), 2.90 (dd, J=13.8, 10.5 Hz, 1H).
Intermediate

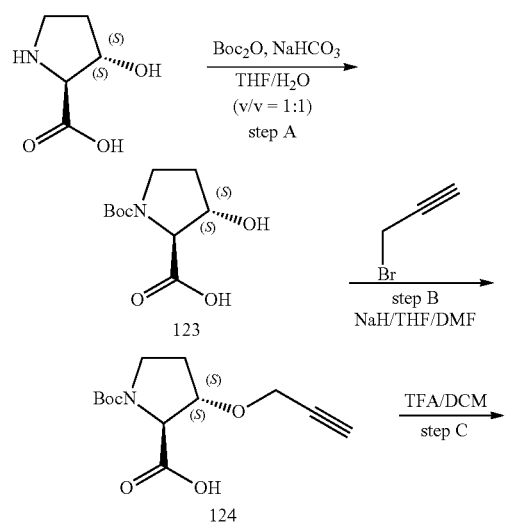

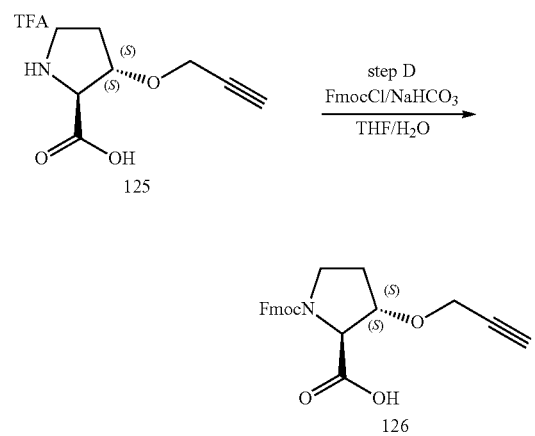

Step A: Synthesis of Intermediate 123

To a stirred solution of (2S,3S)-3-hydroxypyrrolidine-2-carboxylic acid (3.00 g, 22.88 mmol) in THF (150 mL) was added water (150 mL) and NaHCO$_3$ (7.70 g, 92 mmol) at 0° C. The reaction mixture was stirred at room temperature for 15 minutes. After Boc$_2$O (7.50 g, 34.4 mmol) was added, the reaction mixture was stirred at 25° C. for 16 h. The resulting mixture was added sat'd aqueous NaHCO$_3$ (50 mL) and washed with ethyl ether (2×100 mL). The separated organic phases were deserted. The pH value of the aqueous phase was adjusted to 3 with aqueous HCl (1 M). The aqueous solution was extracted with EA (6×200 mL). The organic layers were combined and concentrated under reduced pressure to afford 5.00 g (90% yield) of 123 as an off-white solid. LCMS (ESI) calc'd for $C_{10}H_{17}NO_5$ [M+Na]$^+$: 254.1, found 253.9. $^1$H NMR (300 MHz, CD$_3$OD) δ 4.47-4.33 (m, 1H), 4.19-4.08 (m, 1H), 3.69-3.44 (m, 2H), 2.16-1.97 (m, 1H), 1.94-1.81 (m, 1H), 1.45 (d, J=13.3 Hz, 9H).

Step B: Synthesis of Intermediate 124

To a solution of 123 (1.15 g, 4.72 mmol) in THF (50 mL) were added DMF (10 mL) and NaH (660 mg, 16.50 mmol, 60% in mineral oil) at 0° C. under argon atmosphere. After the reaction mixture was stirred for 15 minutes, 3-bromoprop-1-yne (1.20 g, 10.09 mmol) was added at 0° C. After warming to 25° C., the reaction mixture was stirred for 16 h. The resulting mixture was added sat'd aqueous NaHCO$_3$ (20 mL) and extracted with ethyl ether (2×60 mL). The separated organic phases were deserted. The pH value of the aqueous phase was adjusted to 4 with aqueous HCl (1 M). The aqueous solution was extracted with EA (5×100 mL). The organic layers were combined and concentrated under reduced pressure to afford 1.47 g (98% yield) of 124 as a yellow oil. LCMS (ESI) calc'd for $C_{13}H_{19}NO_5$ [M+Na+CH$_3$CN]$^+$: 333.1, found 333.3. $^1$H NMR (300 MHz, CDCl$_3$) δ 4.66-4.58 (m, 1H), 4.48-4.31 (m, 1H), 4.28-4.18 (m, 2H), 3.61-3.40 (m, 2H), 2.47 (t, J=2.4 Hz, 1H), 2.16-2.01 (m, 2H), 1.47 (d, J=17.3 Hz, 9H)

Step C: Synthesis of Intermediate 125

To a solution of 124 (7.14 g, 19.36 mmol) in DCM (40 mL) was added TFA (20 mL) at room temperature. The reaction solution was stirred at 25° C. for 16 h. The solvent was removed under reduced pressure to afford 8.00 g (95% yield) of 125 with 2,2,2-trifluoroacetic acid (1:1) as a brown oil, which was used in the next step without further purification. LCMS (ESI) calc'd for $C_{10}H_{12}F_3NO_5$ [M–CF$_3$CO$_2^-$]$^+$: 170.1, found 170.0.

Step D: Synthesis of Intermediate 126

To a stirred solution of 125 with 2,2,2-trifluoroacetic acid (1:1) (8.00 g, 18.36 mmol) in THF (150 mL) were added the aqueous NaHCO$_3$ (295 mL, 148 mmol) and Fmoc-Cl (7.20 g, 27.8 mmol). The reaction mixture was stirred at 25° C. for 16 h. The resulting mixture was added sat'd aqueous NaHCO$_3$ (20 mL) and extracted with ethyl ether (2×200 mL). The pH value of the aqueous phase was adjusted to 2 with aqueous HCl (1 M). The aqueous solution was extracted with EA (5×300 mL). The organic layers were combined and concentrated under reduced pressure. The residue was purified by a silica gel column chromatography, eluted with gradient 1%-50% EA in PE. The fractions containing the desired product were combined and concentrated under reduced pressure to afford 5.92 g (78% yield) of 126 as an off-white solid. LCMS (ESI) calc'd for $C_{23}H_{21}NO_5$ [M+H]$^+$: 392.2, found 392.3. $^1$H NMR (300 MHz, CDCl$_3$) δ 9.98 (br, 1H), 7.80-7.65 (m, 2H), 7.63-7.48 (m, 2H), 7.44-7.23 (m, 4H), 4.62-4.08 (m, 7H), 3.77-3.52 (m, 2H), 2.51-2.40 (m, 1H), 2.20-1.96 (m, 2H).

Preparation of Intermediates 128 and 129

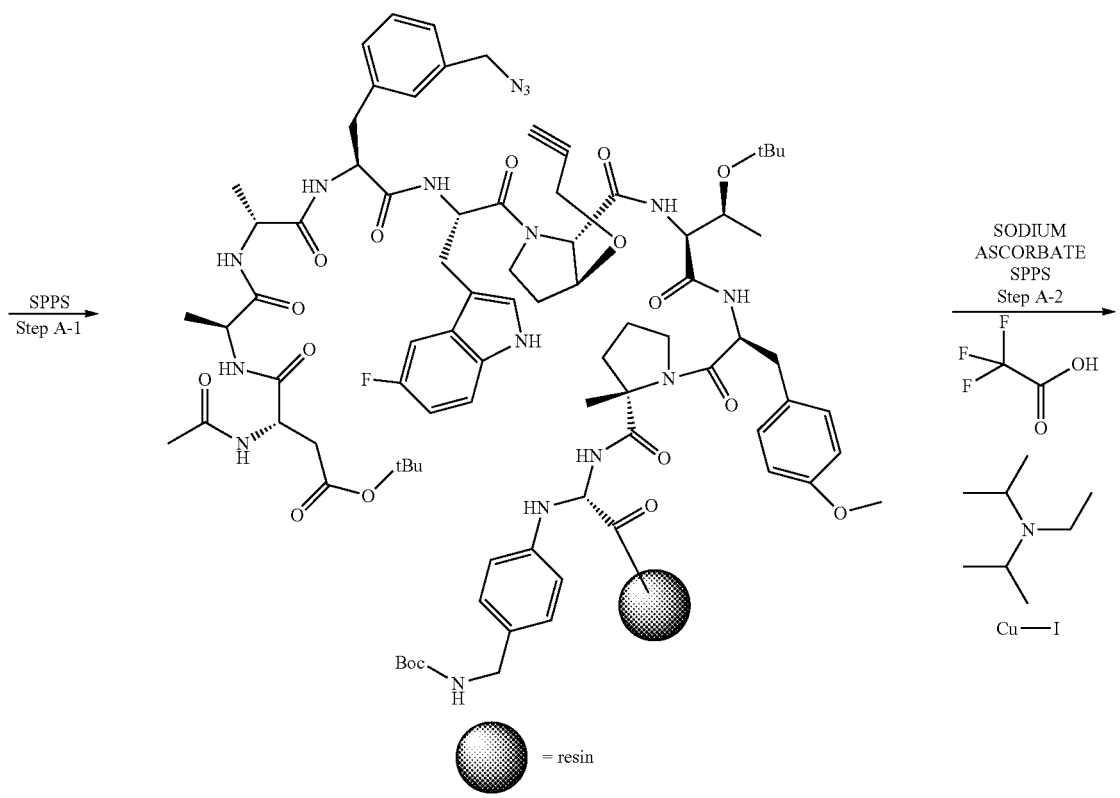

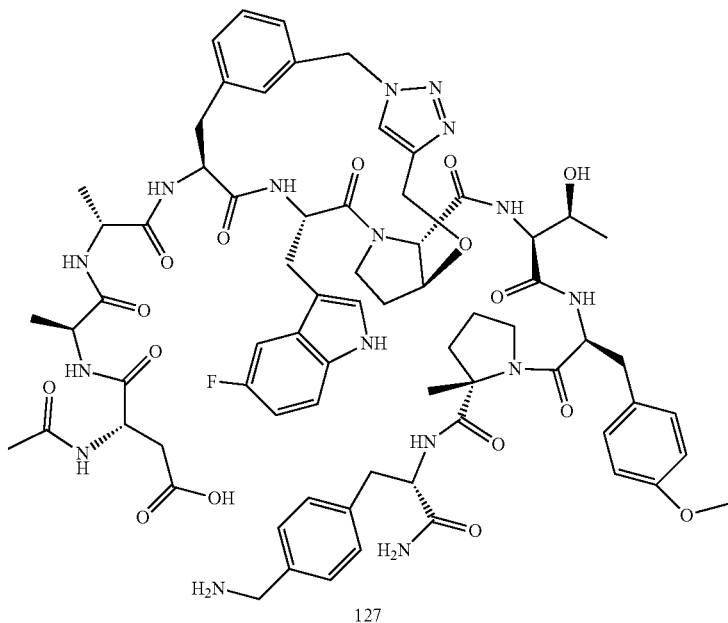

127

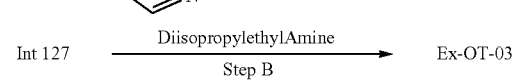

Int 127 →(DiisopropylethylAmine / Step B)→ Ex-OT-03

Step A—Synthesis of Intermediate 127

Step A-1: Peptide was synthesized using Fmoc/t-Bu chemistry on Fmoc-rink amide MBHA resin (Midwest, 0.55 mmol/g) with a CEM Liberty Blue automated microwave peptide synthesizer. The peptide sequence was synthesized on a 0.15 mmol scale, using single-couplings of 3.3 equivalents of Fmoc protected amino acids as a 0.2M DMF solution along with 3.33 eq of 0.5M DIC and 3.33 eq of 1.0M Oxympure containing 10% DIEA. Fmoc deprotections were performed using 20% (V/V) piperidine in DMF. Linear peptide NT- was capped using 10% acetic anhydride in DMF.

The sequence of Fmoc protected amino acids used are:
1. (S)-2-((((9H-fluoren-9-yl)methoxy)carbonyl)amino)-3-(4-(((tert-butoxycarbonyl) amino)methyl) phenyl) propanoic acid
2. (S)-1-(((9H-fluoren-9-yl)methoxy)carbonyl)-2-methylpyrrolidine-2-carboxylic acid
3. (S)-2-((((9H-fluoren-9-yl)methoxy)carbonyl)amino)-3-(4-methoxyphenyl)propanoic acid
4. N-(((9H-fluoren-9-yl)methoxy)carbonyl)-O-(tert-butyl)-L-threonine
5. (2S,3S)-1-(((9H-fluoren-9-yl)methoxy)carbonyl)-3-(prop-2-yn-1-yloxy)pyrrolidine-2-carboxylic acid (Intermediate 126, see prep above)
6. (S)-2-((((9H-fluoren-9-yl)methoxy)carbonyl)amino)-3-(5-fluoro)-1H-indol-3-yl)propanoic acid
7. S)-2-((((9H-fluoren-9-yl)methoxy)carbonyl)amino)-3-(3-(azidomethyl)phenyl)propanoic acid (Intermediate 122, see prep above)
8. (R)-2-((((9H-fluoren-9-yl)methoxy)carbonyl)amino)propanoic acid
9. (S)-2-((((9H-fluoren-9-yl)methoxy)carbonyl)amino)propanoic acid
10. (S)-2-((((9H-fluoren-9-yl)methoxy)carbonyl)amino)-4-(tert-butoxy)-4-oxobutanoic acid Step A-2: The peptidyl resin from Step A-1 was removed from the synthesizer to a vial, 10 ml of DMSO, N-ethyl-N-isopropylpropan-2-amine (0.15 g, 1.2 mmol), sodium (R)-2-((S)-1,2-dihydroxyethyl)-4-hydroxy-5-oxo-2,5-dihydrofuran-3-olate (0.12 g, 0.6 mmol) was added and dissolved in 0.5 ml of water. The mixture was bubbled with N2 for 10 min, then copper(I) iodide (0.12 g, 0.6 mmol) was added and dissolved in 1 ml of DMSO. The vial was capped, and blanked with N2. The reaction was stirred at room temperature overnight. The resin was washed thoroughly with DMF, MeOH, DCM, and a solution mixture of 0.5% sodium diethyldithio carbamate and 0.5% DIEA in DMF. After isolation of the resin via filtration, the peptide was cleaved from solid support using 15 ml of TFA solution (v/v) (95% TFA: 2.5% triisopropylsilane: 2.5% water) for approximately 2 hours, at room temperature. The resin was filtered, and washed with 5 ml of TFA solution. Combined filtrate was concentrated, and precipitated in approximately 70 ml of cold ethyl ether (−78 C). Crude peptide pellet collected by centrifugation was washed in cold ethyl ether and centrifuged once more to provide Int-127, which was used crude in the next step.

LCMS anal. calcd. for C71H87FN16O16: 1439.6; Found: 1440.4 (M+1)$^+$.

Step B—Synthesis of Ex-OT-02

Crude 127 (20 mg) was dissolved in 3 ml of DMF. HATU (0.021 mmol) and DIEA (0.042 mmol) were added, mixed and stirred at room temperature until reaction was complete. The mixture was concentrated in vacuo and purified using gradient elution on reverse phase (30×150 mm Sunfire Prep C18; 20-70% CH3CN/water w/ 0.1% TFA modifier over 40 min). The fractions were lyophilized to provide compound Ex-OT-03.

LCMS anal. calcd. for C71H85FN16O15 1421.56: Found: 1421.3 (M+1)$^+$.

Compound Ex-OT-04 was prepared from Int 127 using analogous chemistry to that described herein for the preparation of Ex-C07 from Ex-C06. Ex-OT-04 was purified using LC/MS with the following data obtained: LCMS anal. calcd. for C75H96FN16O14$^+$: 1464.7; Found: 1463.4 (M)$^+$.

Example 10 Preparation of Ex-OT-05

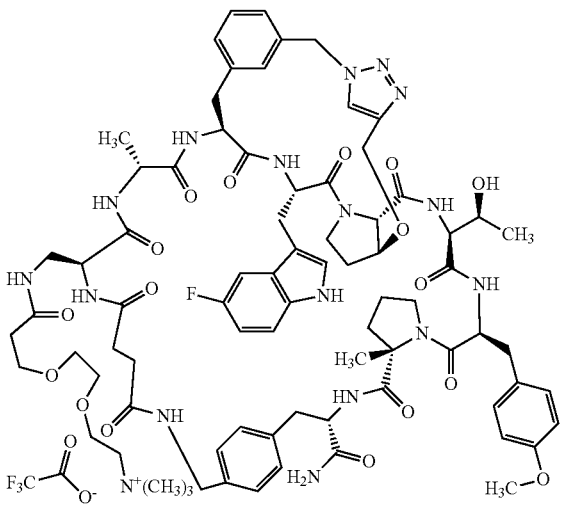

Ex-OT-05/131

The compound was prepared in accordance with the following schemes and experimental description:

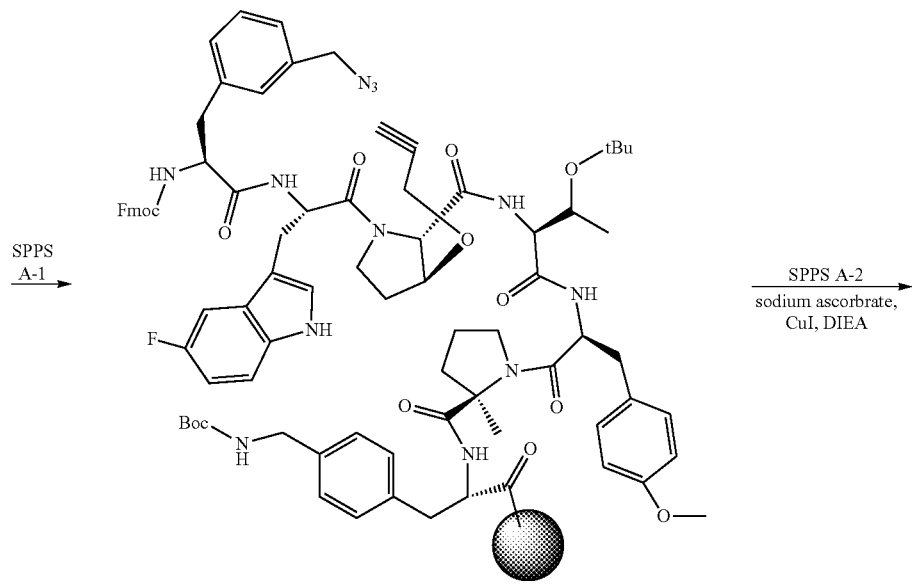

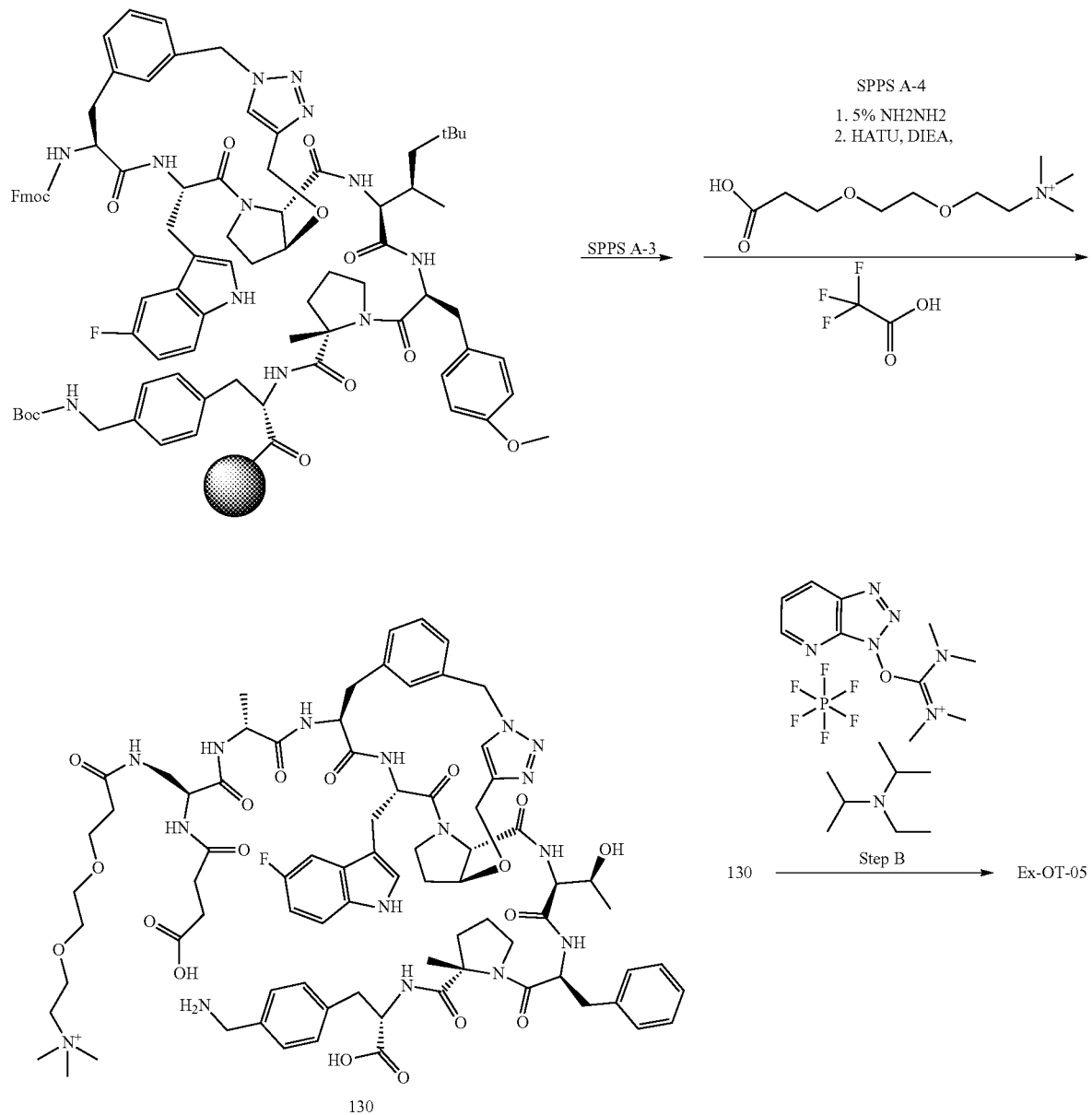

Step A—Synthesis of Intermediate Compound 130

Step A-1: The Peptide was Synthesized Using Fmoc/t-Bu Chemistry on Fmoc-MBHA Resin Spiraltide resin (CEM, 0.19 mmol/g) with a CEM Liberty Blue automated microwave peptide synthesizer. The peptide sequence was synthesized on a 0.20 mmol scale, using single-couplings of 5 equivalents of Fmoc protected amino acids as a 0.2M DMF solution along with 5 eq of 0.5M DIC and 5 eq of 1.0M Oxympure containing 10% DIEA. Fmoc deprotections were performed using 20% (V/V) piperidine in DMF.

The sequence of Fmoc protected amino acids used are:
1. (S)-2-((((9H-fluoren-9-yl)methoxy)carbonyl)amino)-3-(4-(((tert-butoxycarbonyl) amino)methyl) phenyl) propanoic acid
2. (S)-1-(((9H-fluoren-9-yl)methoxy)carbonyl)-2-methylpyrrolidine-2-carboxylic acid
3. (S)-2-((((9H-fluoren-9-yl)methoxy)carbonyl)amino)-3-(4-methoxyphenyl)propanoic acid
4. N-(((9H-fluoren-9-yl)methoxy)carbonyl)-O-(tert-butyl)-L-threonine
5. (2S,3S)-1-(((9H-fluoren-9-yl)methoxy)carbonyl)-3-(prop-2-yn-1-yloxy)pyrrolidine-2-carboxylic acid (Intermediate 133)
6. (S)-2-((((9H-fluoren-9-yl)methoxy)carbonyl)amino)-3-(5-fluoro)-1H-indol-3-yl)propanoic acid 7. S)-2-((((9H-fluoren-9-yl)methoxy)carbonyl)amino)-3-(3-(azidomethyl)phenyl)propanoic acid (Intermediate 129)

Step A-2: The peptidyl resin was removed from Step A-1 from the synthesizer to a vial. 10 ml of DMSO, N-ethyl-N-isopropylpropan-2-amine (0.2 g, 1.6 mmol), sodium (R)-2-((S)-1,2-dihydroxyethyl)-4-hydroxy-5-oxo-2,5-dihydrofuran-3-olate (0.32 g, 1.6 mmol) were added and dissolved in 0.5 ml of water. The mixture was bubbled with N2 for 10 min, then added copper(I) iodide (0.16 g, 0.8 mmol) dissolved in 1 ml of DMSO. The vial was capped, and blanked with N2. The reaction was stirred at room temperature overnight. Then the resin was washed thoroughly with DMF, MeOH, DCM, and a solution mixture of 0.5% sodium diethyldithio carbamate and 0.5% DIEA in DMF.

Step A-3: The sequence assembly of peptidyl resin from Step A-2 was continued on CEM Liberty Blue automated microwave peptide synthesizer using the same protocol as Step A-1. The sequence of Fmoc protected amino acids used are:
1. (R)-2-((((9H-fluoren-9-yl)methoxy)carbonyl)amino)propanoic acid
2. (S)-2-((((9H-fluoren-9-yl)methoxy)carbonyl)amino)-3-((1-(4,4-dimethyl-2,6-dioxocyclohexylidene)-3-methylbutyl)amino)propanoic acid
3. 4-(tert-butoxy)-4-oxobutanoic acid Step A-4: The resin was removed from Step A-3 from the synthesizer. 5% NH2NH2 in DMF 5 min, two time, was added to remove iVDde group on the side chain, followed by thorough wash with DMF, DCM, and Methanol. 2-(2-(2-carboxyethoxy)ethoxy)-N,N,N-trimethylethanaminium (Int XXX) (0.4 mmol, 0.088 mg), HATU (0.4 mmol, 152 mg), and DIEA (0.8 mmol, 0.2 ml of 2M) were added. The mixture was mixed well and stirred at room temperature until the reaction was complete. The completed resin was cleaved by 15 ml of 95% TFA:2.5% TIS: 2.5% water for 2 hours, at room temperature. Another 5 ml of TFA solution was used to wash the peptidyl resin. After filtering, combined TFA solutions were condensed on a rotary evaporator, and precipitated in approximately 70 ml of cold ethyl ether (−78 C). Crude peptide pellet collected by centrifugation was washed in cold ethyl ether and centrifuged once more to provide 130 which was used crude in the next step. LCMS anal. calcd. for C79H104FN16O19+ 1600.79; Found: 1600.4 (M)+.

Step B—Synthesis of Compound Ex-OT-05

Crude 131 (50 mg) was dissolved in 4.5 ml of DMF. HATU (0.054 mmol) and DIEA (0.1 mmol), were added, mixed and stirred at room temperature until reaction was complete. The mixture was concentrated in vacuo and directly purified using gradient elution on reverse phase (30×150 mm Sunfire Prep C18; 5-65% CH3CN/water w/ 0.1% TFA modifier over 40 min). The fractions were lyophilized to provide compound Ex-OT-05. LCMS anal. calcd. for C79H102FN16O18+: 1582.78; Found: 1582.4 (M)+.

Example 11 Preparation of Ex-OT-06

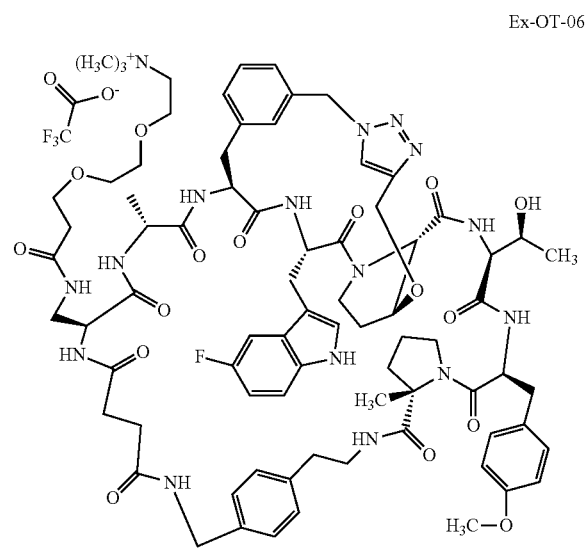

Example Compound Ex-OT-06 was prepared in accordance with the following schemes and synthetic procedures:

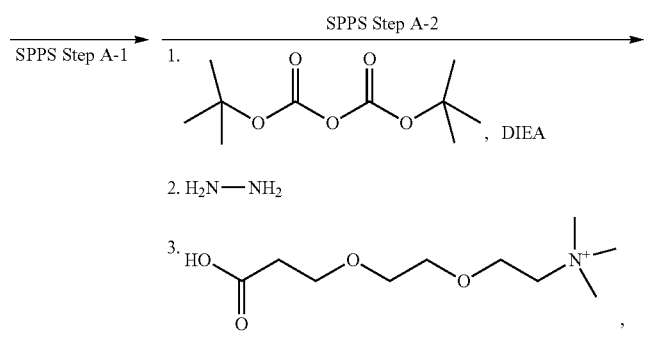

-continued
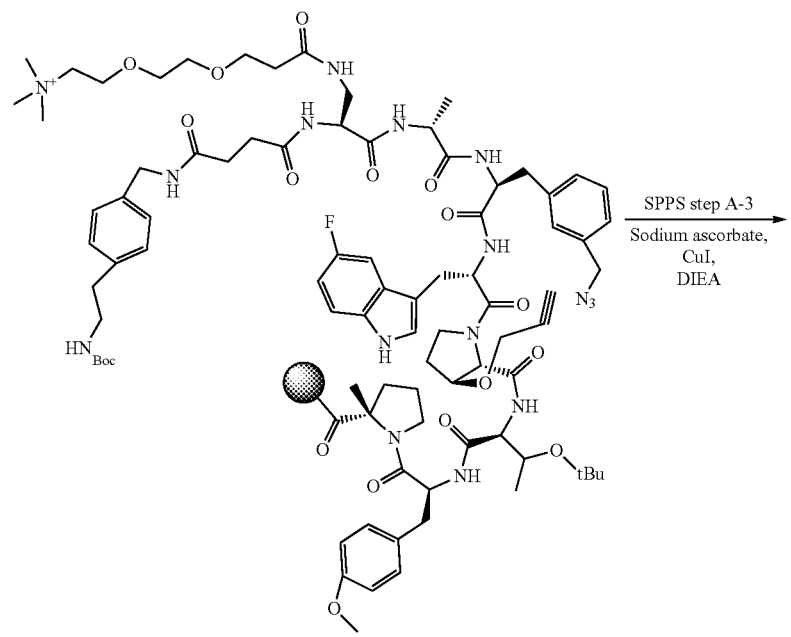
SPPS step A-3
Sodium ascorbate,
CuI,
DIEA
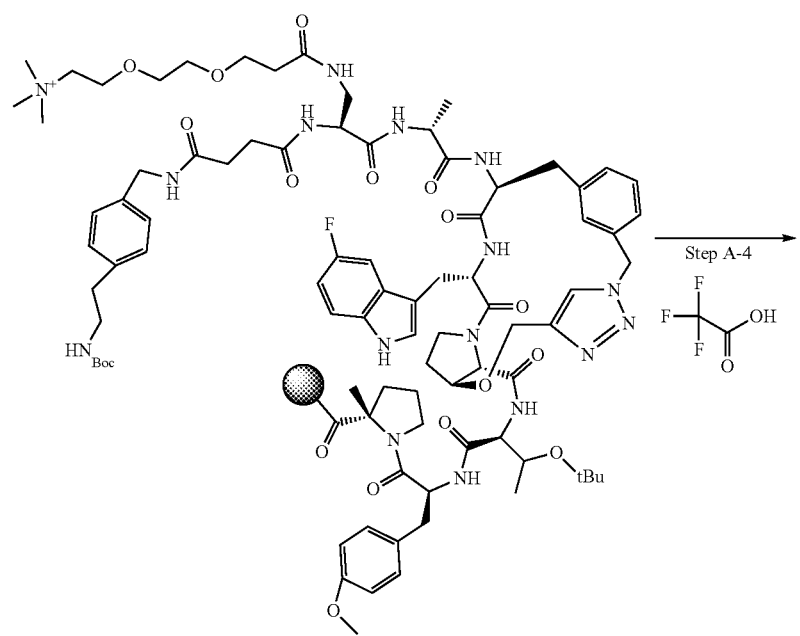
Step A-4
TFA

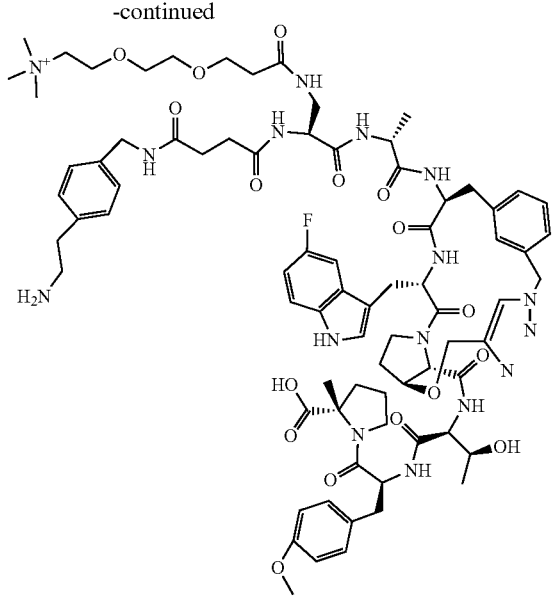
Int 141
Int 141 —Step B→ Ex-OT-06
Preparation of Int 135
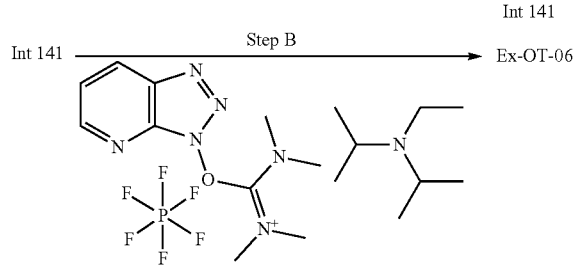
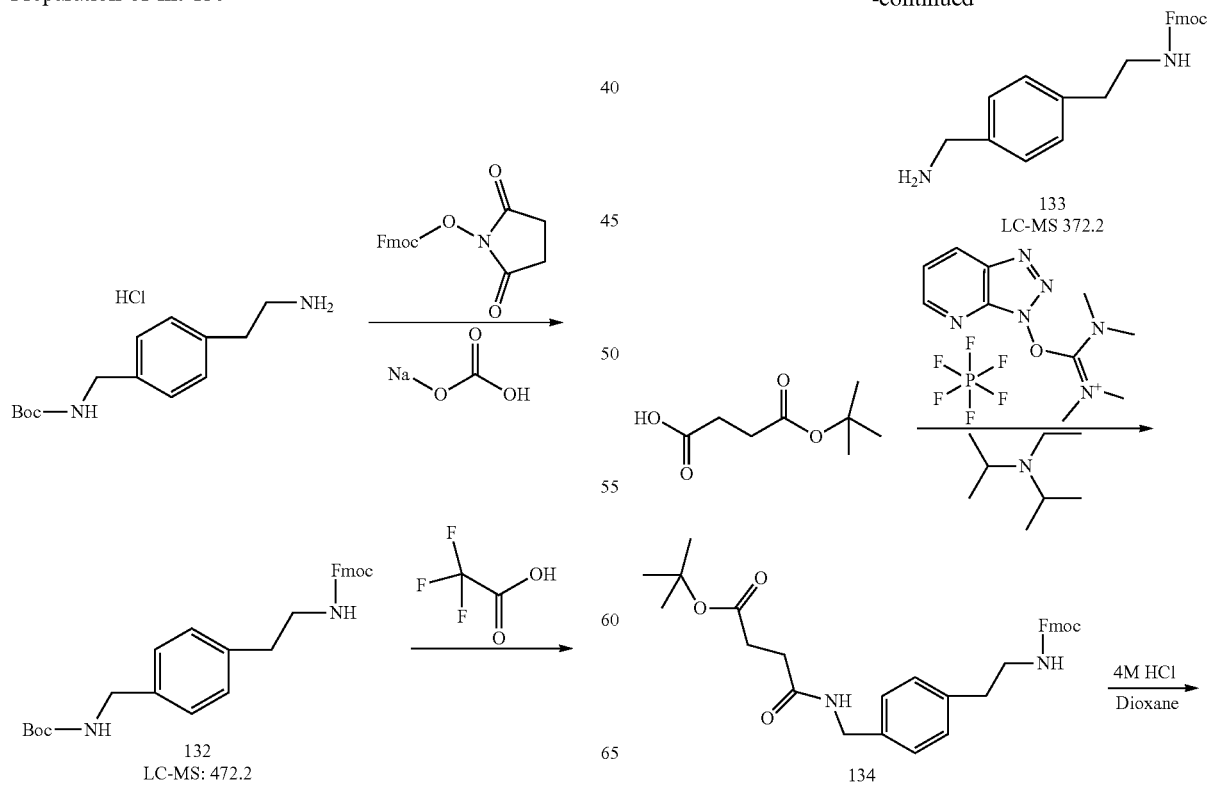

-continued

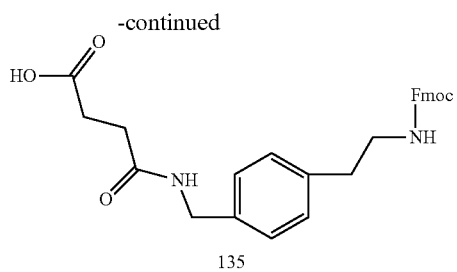

135

Step A—Synthesis of Intermediate 132

A solution of 1.00 g (3.49 mmol) of tert-butyl 4-(2-aminoethyl)benzylcarbamate hydrochloride was dissolved in 30 ml of acetone, and the resulting solution treated with 0.59 g (6.97 mmol) of sodium bicarbonate in 10 ml water. A white precipitate formed immediately. An additional 20 ml of acetone was added and the reaction cleared. Approx. 1 hr later, a precipitate was formed. The suspension was stirred for 3 h, at which no SM was detected by LC-MS analysis. The mixture was stored at 4° C. overnight. The reaction mixture was concentrated to remove acetone, was acidified to pH 3-4 with 50 ml of 1M HCl.

The reaction was extracted with 2×40 ml of EtOAc. The combined extracts were washed with brine and concentrated to give a white powder. A large peak was present in the LC-MS for the desired product (MS=472.2), and the crude product was used as is in the next reaction.

Step B—Synthesis of Intermediate 133

A solution of 1.42 g (3.00 mmol) of 132 was dissolved in 2 ml TFA/2 ml dicholormethane. After 1 h, the reaction was complete by LC-MS analysis (MS product=372.2), and was conc. in vacuo to give the crude product as an oil, used immediately in the next step.

Step C— Synthesis of Intermediate 134

A solution of 1.00 g (2.68 mmol) of intermediate 133 in 2 ml of DMF was treated with 1.60 g (4.21 mmol) of 2-(3H-[1,2,3]triazolo[4,5-b]pyridin-3-yl)-1,1,3,3-tetramethylisouronium hexafluorophosphate(V) in 2 ml of DMF and 5 ml (10.00 mmol) of DIEA. After 5 min, this mixture was added to a solution of 0.60 g (3.44 mmol) of 4-(tert-butoxy)-4-oxobutanoic acid in 1 ml DMF. The resulting solution was stirred for 30 min., at which point LC-MS analysis indicated completion of the reaction. The reaction was concentrated in vacuo to give the crude desired product (MS=528.30) which was used as is in the next reaction.

Step 4—Synthesis of intermediate 135

To a solution of 1.42 g (2.68 mmol) of intermediate 134 in 2 ml DMF was added 33.5 ml of 4M HCl/dioxane. The resulting solution was stirred overnight. The reaction was diluted with 1 volume of EtOAc/1 volume water. The layers were separate, the aqueous layer reextracted with 1 volume of EtOAc, and the EtOAc extracts combined and concentrated. The crude product was purified via prep HPLC using the following conditions: column: Sunfire C18 50×150, 5 u Mobile phases: A=0.1% TFA in water, B=0.1% TFA in acetonitrile flow rate 85 ml/min gradient: 1% for 10 min. 5-65% in 40 min This provided 0.75 g (1.59 mmol) of pure desired product as a fluffy white amorphous powder after lyophilization, MS=472.2.

Preparation of Int 141

Step A-1: First, 2-Cl trityl chloride resin (0.25 mmol, 1.28 mmol/g, Rapp Polymer) was loaded manually in DCM with (S)-1-(((9H-fluoren-9-yl)methoxy)carbonyl)-2-methylpyrrolidine-2-carboxylic acid (0.18 g, 0.5 mmol) and 2M DIEA (1 mmol). Stirred at room temperature for 30 min. The resin was then washed thoroughly, then capped with 10 ml of DCM:Methanol: DIEA 85:15:5 for 30 min. This preloaded resin was then moved to CEM Liberty Blue automated peptide synthesizer (CEM Corp.) using Fmoc/tBu chemistry. The peptide sequence was synthesized on a 0.25 mmol scale, using single-couplings of 4 equivalents of Fmoc protected amino acids as a 0.2M DMF solution along with 3.6 eq of 0.45M HATU in DMF and 8 eq of 2M DIEA. Fmoc deprotections were performed using 20% (V/V) piperidine in DMF. The sequence of Fmoc protected amino acids used are:

1. (S)-1-(((9H-fluoren-9-yl)methoxy)carbonyl)-2-methylpyrrolidine-2-carboxylic acid
2. (S)-2-((((9H-fluoren-9-yl)methoxy)carbonyl)amino)-3-(4-methoxyphenyl)propanoic acid
3. N-(((9H-fluoren-9-yl)methoxy)carbonyl)-O-(tert-butyl)-L-threonine
4. (2S,3S)-1-(((9H-fluoren-9-yl)methoxy)carbonyl)-3-(prop-2-yn-1-yloxy)pyrrolidine-2-carboxylic acid (Intermediate 133)
5. (S)-2-((((9H-fluoren-9-yl)methoxy)carbonyl)amino)-3-(5-fluoro-)-1H-indol-3-yl)propanoic acid
6. S)-2-((((9H-fluoren-9-yl)methoxy)carbonyl)amino)-3-(3-(azidomethyl)phenyl)propanoic acid (Intermediate 129)
7. (R)-2-((((9H-fluoren-9-yl)methoxy)carbonyl)amino)propanoic acid
8. (S)-2-((((9H-fluoren-9-yl)methoxy)carbonyl)amino)-3-((1-(4,4-dimethyl-2,6-dioxocyclohexylidene)-3-methylbutyl)amino)propanoic acid
9. 4-((4-(2-((((9H-fluoren-9-yl)methoxy)carbonyl)amino)ethyl)benzyl)amino)-4-oxobutanoic acid (Intermediate 135, see prep above)

Step A-2: The peptidyl resin was removed from Step A-1 from the synthesizer, Boc anhydride (1.0 mmol, 0.24 g) and DIEA (1.0 mmol, 1 ml of 2M) were added in DMF, stirred at room temperature for 30 min. The resin was washed thoroughly, and 5% NH2NH2 in DMF 5 min was added, two times, to remove iVDde group on the side chain, followed by a thorough wash with DMF, DCM, and methanol, added 2-(2-(2-carboxyethoxy)ethoxy)-N,N,N-trimethylethanaminium (IntXXX) (0.4 mmol, 0.088 mg), HATU (0.4 mmol, 152 mg), and DIEA (0.8 mmol, 0.2 ml of 2M). The mixture was mixed well and stirred at room temperature until reaction complete.

Step A-3: To peptidyl resin from Step A-2, was added 10 ml of DMSO, N-ethyl-N-isopropylpropan-2-amine (1 ml of 2M, 2.0 mmol), sodium (R)-2-((S)-1,2-dihydroxyethyl)-4-hydroxy-5-oxo-2,5-dihydrofuran-3-olate (0.2 g, 1.0 mmol) dissolved in 0.5 ml of water. The mixture was bubbled with N2 for 10 min, then copper(I) iodide (0.2 g, 1.0 mmol) dissolved in 1 ml of DMSO was added. The vial was capped, and blanked with N2. The reaction was stirred at room temperature overnight. The resin was then washed thoroughly with DMF, MeOH, DCM, and a solution mixture of 0.5% sodium diethyldithio carbamate and 0.5% DIEA in DMF.

Step A-4: To peptidyl resin from Step A-3, added 15 ml of 95% TFA:2.5% TIS: 2.5% water, and the mixture was stirred at room temperature for 2 hours. Another 5 ml of TFA solution was used to wash the peptidyl resin. After filtering, combined TFA solutions were condensed on a rotary evaporator, and precipitated in approximately 70 ml of cold ethyl ether (−78 C). Crude peptide pellet collected by centrifugation was washed in cold ethyl ether and centrifuged once more, redissolved in 50% acetonitrile/water (modified with 0.1% TFA) and water, lyophilized. This mixture was purified using gradient elution on reverse phase (30×150 mm Sunfire Prep C18; 5-65% CH3CN/water w/ 0.1% TFA modifier over 40 min). The fractions were lyophilized to provide Int-141, which was used in the next step. LCMS anal. calcd. for C78H104FN16O17+1556.8; Found: 1556.3 (M)+

Step B—Synthesis of Intermediate Ex-OT-06

Int-141 (20 mg) was dissolved in 2.0 ml of DMF. Added HATU (0.04 mmol) and DIEA (0.08 mmol), mixed and stirred at room temperature until reaction was complete. The mixture was concentrated in vacuo and directly purified using gradient elution on reverse phase (30×150 mm Sunfire Prep C18; 5-65% CH3CN/water w/ 0.1% TFA modifier over 40 min). The fractions were lyophilized to provide Ex-OT-06. LCMS anal. calcd. for C78H102FN16O16+ 1538.8; Found: 1539.4 (M)+

Example 12 Preparation of Example Compound Ex-C01

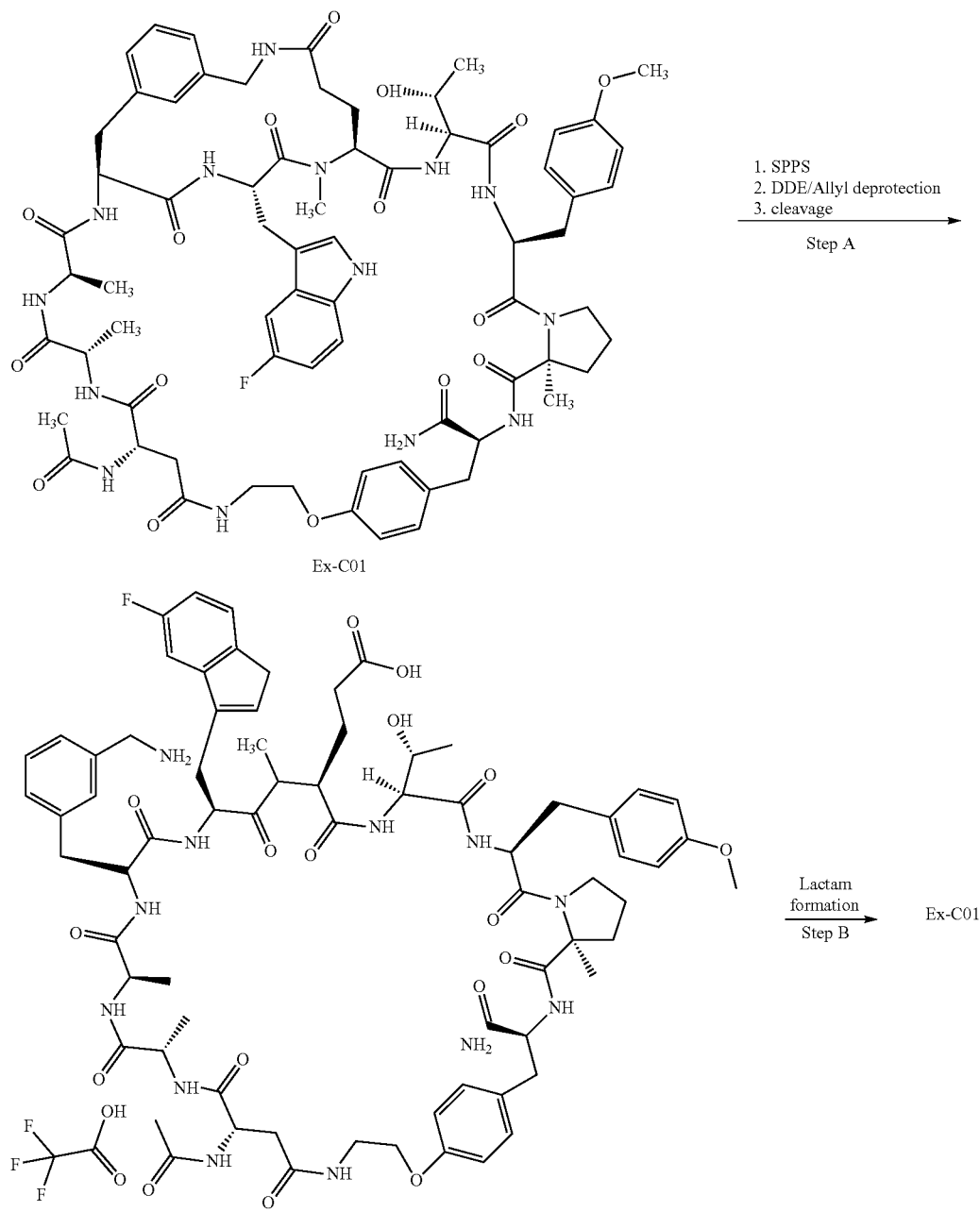

Step A—Synthesis of Intermediate 137

The peptide was synthesized manually using Fmoc/t-Bu chemistry on PS Rink-Amide resin (loading 0.47 mmol/g). Up to Thr, the peptide sequence was synthesized on a CEM Liberty Blue synthesizer on a 0.3 mmol scale, using single-couplings of Fmoc protected amino acid, with DIC and OXYME as activators in DMF at 90° C. Then, peptide synthesis was continued manually using single-couplings of 2 eq of Fmoc protected amino acid, 2 eq of HOAt and 2 eq of DIC, in DMF at r.t. Coupling reactions were monitored by Kaiser test. Couplings following secondary amines were monitored by chloranil test. Fmoc deprotections were performed using 20% (VNV) piperidine in DMF. Final acetylation was performed with 10 eq of Ac2O and monitored by Kaiser test.

The sequence of Fmoc protected amino acids and building blocks used are:
1. (S)-2-((((9H-fluoren-9-yl)methoxy)carbonyl)amino)-3-(4-(2-((1-(4,4-dimethyl-2,6-dioxocyclohexylidene)ethyl)amino)ethoxy)phenyl)propanoic acid
2. (S)-1-(((9H-fluoren-9-yl)methoxy)carbonyl)-2-methylpyrrolidine-2-carboxylic acid (S)-2-((((9H-fluoren-9-yl)methoxy)carbonyl)amino)-3-(4-methoxyphenyl)propanoic acid
3. N-(((9H-fluoren-9-yl)methoxy)carbonyl)-O-(tert-butyl)-L-threonine
4. (S)-2-((((9H-fluoren-9-yl)methoxy)carbonyl)(methyl)amino)-5-(tert-butoxy)-5-oxopentanoic acid
5. (S)-2-((((9H-fluoren-9-yl)methoxy)carbonyl)amino)-3-(5-fluoro-1H-indol-3-yl)propanoic acid
6. (S)-2-((((9H-fluoren-9-yl)methoxy)carbonyl)amino)-3-(3-(((tert-butoxycarbonyl)amino)methyl)phenyl)propanoic acid
7. (((9H-fluoren-9-yl)methoxy)carbonyl)-D-alanine (D-Ala)
8. (((9H-fluoren-9-yl)methoxy)carbonyl)-L-alanine (Ala)
9. (S)-2-((((9H-fluoren-9-yl)methoxy)carbonyl)amino)-4-(allyloxy)-4-oxobutanoic acid (Asp OAll)

At the end of the assembly the resin was dissolved in dry DCM. Phenilsilane (24 eq.) and Palladium Tetrakis (CAS: 14221-01-3, 0.25 eq) were added. Reaction was kept under stirring for 30 min at r.t. under N2 atmosphere (2 cycles of 30 min) and then washed with a 5% solution of Sodium diethyldithiocarbamate in DMF with 5% of DIPEA (200 ml). DDe removal was performed washing the resin with 100 mL of a 3% hydrazine monohydrate solution in DMF. Lactam formation was performed on solid phase: a solution of PyAOP (2.5 eq), HOAt (2.5 eq) and DIPEA (5 eq) in DMF was added to the resin. Reaction complete after 10-15 min (monitored by test cleavage). The resin was washed with DMF, MeOH, DCM, Et2O. The peptide was cleaved from solid support using 60 ml of TFA solution (v/v) (91% TFA, 5% H2O, 4% TIPS) for approximately 1.5 hours, at room temperature. The resin was filtered, washed with TFA, concentrated to dryness and lyophilized to afford 97 mg of 137.

LCMS anal. calcd. For C70H89FN14O17: 1417.56; found: 1418.9 (M+1)$^+$.

Step B—Synthesis of Compound Ex-C01

Intermediate 137 (20 mg) was dissolved in DMF (2 mL). HATU (1 eq) and DIPEA (2 eq) were added. Reaction completed after 5 min, and was quenched with TFA, concentrated to dryness and purified by RP-HPLC (Dr. Maisch Reprosil Gold C18, 20×150 mm, 5 um, 100 A; 20% to 35% ACN/water+0.1% TFA modifier over 25 min). Collected fractions were lyophilized to provide Ex-C01 (3.0 mg).

LCMS anal. calcd. For C70H87FN14O16: 1399.55; found: 1399.9 (M+1)$^+$.

Example 13 Preparation of Ex-C02

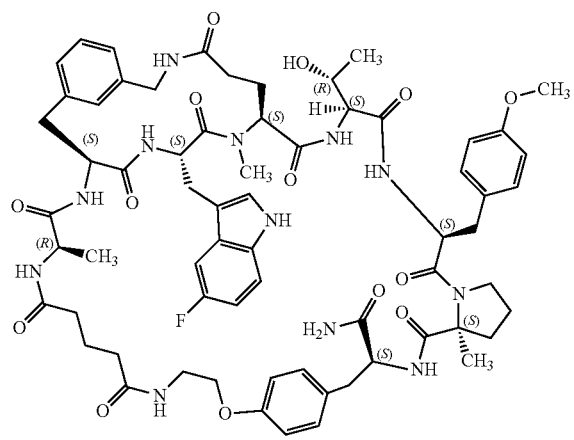

Ex-C02

Ex-C02 was prepared in accordance with the following schemes and synthesis procedures:

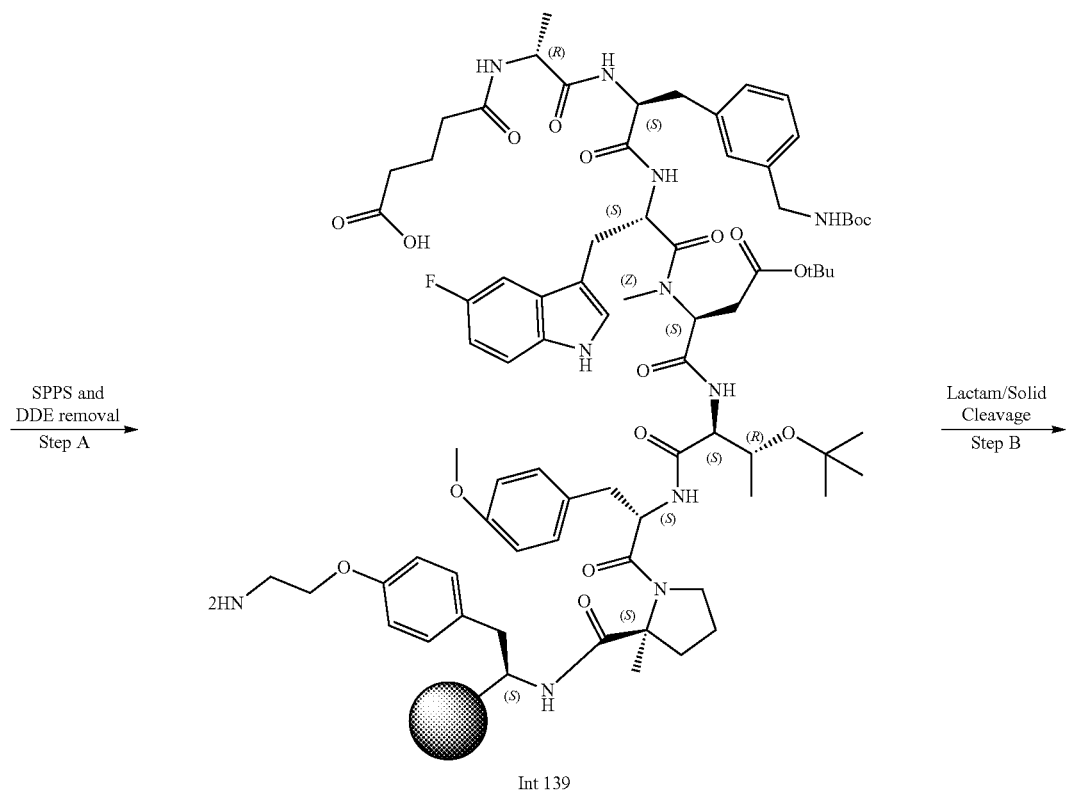
Int 139
SPPS and DDE removal
Step A →
Lactam/Solid Cleavage
Step B →
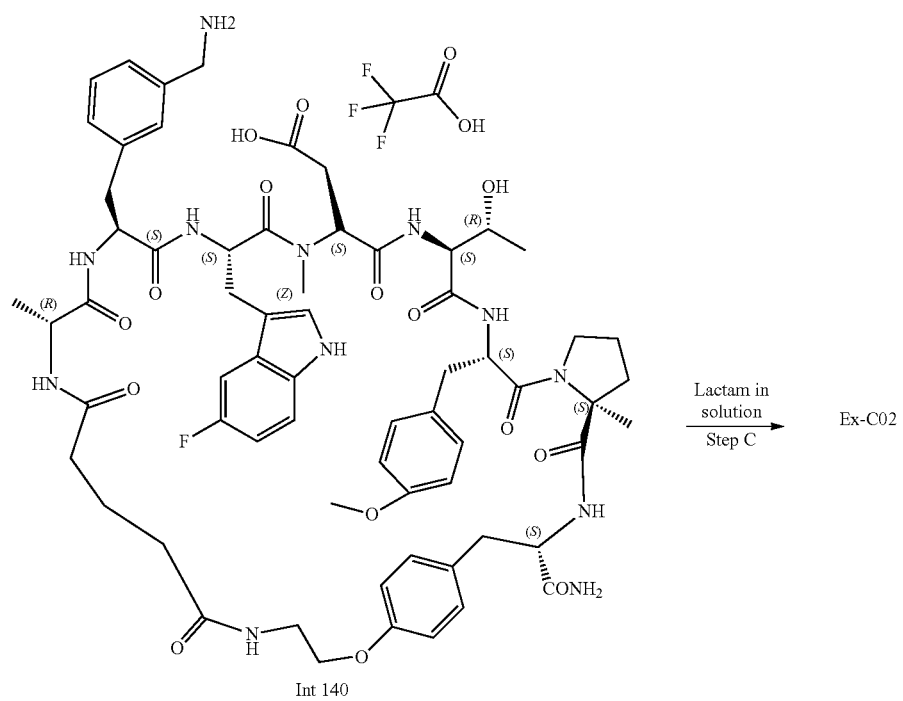
Int 140
Lactam in solution
Step C → Ex-C02

Step A—Synthesis of Intermediate 139

The peptide was synthesized manually using Fmoc/t-Bu chemistry on a PS rink-amide resin (Novabiochem—loading: 0.35 mmol/g) —250 umol scale, using single-couplings of 3 equivalents of Fmoc protected amino acids as a 0.3M DMF solution along with 3 eq of HOAt as a 0.3 M DMF solution and 3 eq of DIC. Fmoc deprotections were performed using 20% (V/V) piperidine in DMF.

The sequence of Fmoc protected amino acids and building blocks used are:
1. (S)-2-((((9H-fluoren-9-yl)methoxy)carbonyl)amino)-3-(4-(2-((1-(4,4-dimethyl-2,6-dioxocyclohexylidene)ethyl)amino)ethoxy)phenyl)propanoic acid
2. (S)-1-(((9H-fluoren-9-yl)methoxy)carbonyl)-2-methylpyrrolidine-2-carboxylic acid
3. (S)-2-((((9H-fluoren-9-yl)methoxy)carbonyl)amino)-3-(4-methoxyphenyl)propanoic acid
4. N-(((9H-fluoren-9-yl)methoxy)carbonyl)-O-(tert-butyl)-L-threonine
5. (S)-2-((((9H-fluoren-9-yl)methoxy)carbonyl)(methyl)amino)-5-(tert-butoxy)-5-oxopentanoic acid
6. (S)-2-((((9H-fluoren-9-yl)methoxy)carbonyl)amino)-3-(5-fluoro-1H-indol-3-yl)propanoic acid
7. (S)-2-((((9H-fluoren-9-yl)methoxy)carbonyl)amino)-3-(3-(((tert-butoxycarbonyl)amino)methyl)phenyl)propanoic acid
8. (((9H-fluoren-9-yl)methoxy)carbonyl)-D-alanine
9. pentandioic acid After the last coupling, resin was treated with 100 mL of a 3% NH2-NH2 solution in DMF for 10 minutes, in order to remove Dde group. Then, resin was washed several times with DMF.

Step B—Synthesis of Intermediate 140

Resin was treated with a solution of PyAOP (5 eq.), HOAt (5 eq.) and DIPEA (10 eq.) in DMF (5 ml) for 1 h, then dried and washed. Test cleavage confirmed the lactam formation. The resin was washed with DMF, MeOH, DCM, Et2O and dried under vacuum. The peptide was cleaved from solid support using 60 ml of TFA solution (v/v) (91% TFA, 5% $H_2O$, 4% TIPS) for approximately 1.5 hours, at room temperature. The resin was filtered, washed with TFA, concentrated to dryness and lyophilized. Yield: 43%.

LCMS anal. calcd. for $C_{66}H_{83}FN_{12}O_{15}$: 1303.4; Found: 1303.9 (M+1)+.

Step C—Synthesis of Ex-C02

Intermediate 140 (0.030 g, 0.023 mmol) was dissolved in DMF in a final concentration of 10 mg/mL. HATU (1 eq.) and DIPEA (2 eq.) were added. After 5 min UPLC-MS confirmed the formation of the second lactam. The reaction mixture was quenched with TFA and purified by RP-HPLC (C18 Dr. Maisch Reprosil Gold Semi-Prep column, 20×150 mm, 5 um, 120 Å, 20% to 40% B in 20 min, A: H2O 0.1% TFA. B: ACN 0.1% TFA). Fractions collected and lyophilized provided 1.8 mg (Y=6%; Purity >95%) of Example Compound Ex-C02. LCMS anal. calcd. for $C_{66}H_{81}FN_{12}O_{14}$: 1285.4; Found: 1286 (M+1)+

Activity Determination

Selected compounds of the invention were subjected to one or more of the following procedures to assay their activity for antagonism of PCSK9 activity.

The following is a description of the assays used to determine activity of compounds of the invention, and any comparator compounds reported, toward PCSK9 antagonism. Biotinylated PCSK9 was obtained by commercially

LDLR TR-FRET

The PCSK9 TR-FRET assay measures the interaction between PCSK9 and LDLR. A solution containing 40 nM biotinylated PCSK9+10 nM Lance ULight Streptavidin is made in 50 mM HEPES pH 7.4, 0.15 M NaCl, 5 mM CaCl2, 0.01% BSA, and 0.01% Surfactant P20. A separate solution containing 40 nM rhLDLR-6×His+10 nM Eu-W1024 anti-6×His is made in the same buffer system. An Echo is used to transfer 0.750 ul of compound to an assay plate followed by the addition of 15 ul of PCSK9+Ulight and 15 ul of LDLR+Eu. The final assay volume is 30.750 ul containing 20 nM PCSK9, 5 nM Ulight, 20 nM LDLR, and 5 nM Eu. The reaction is incubated at room temperature for at least two hours prior to fluorescence measurements using an Envision Multilabel Reader. IC50 values are determined by fitting data to a sigmoidal dose-response curve using non-linear regression. Counts (B-counts) of the europium-labeled LDLR are followed to observe if compounds are adversely affecting LDLR. A fall off of the B-counts is likely indicates a false positive of inhibition.

Alexa FRET Standard TR-FRET

The PCSK9 Alexa FRET Standard assay measures the interaction between PCSK9 and an AlexaFluor647 (AF) tagged cyclic peptide, Reagent A ($K_D$=83 nM). A solution containing 1 nM biotinylated PCSK9+2.5 nM Lance Streptavidin Europium (Strep-Eu) is made in 50 mM HEPES pH 7.4, 0.15 M NaCl, 5 mM CaCl2, 0.01% BSA, and 0.01% Surfactant P20. A separate solution containing 40 nM of the AlexaFluor tagged cyclic peptide is made in the same buffer system. An Echo is used to transfer 0.750 ul of compound to an assay plate followed by the addition of 15 ul of PCSK9+Stept-Eu and 15 ul of AF peptide. The final assay volume is 30.750 ul containing 0.5 nM PCSK9, 1.25 nM Strep-Eu, and 20 nM AF cyclic peptide. The reaction is incubated at room temperature for at least two hours prior to fluorescence measurements using an Envision Multilabel Reader. IC50 values are determined by fitting data to a sigmoidal dose-response curve using nonlinear regression. Ki is then calculated from the Ic50 and the $K_D$ of AF cyclic peptide. Counts (B-counts) of the europium-labeled PCSK9 are followed to observe if compounds are adversely PCSK9. A fall off of the B-counts is likely indicates a false positive of inhibition. Data from this procedure is reported as "A='numerical value' (nanomolar)"

Reagent A was prepared in accordance with the following method:
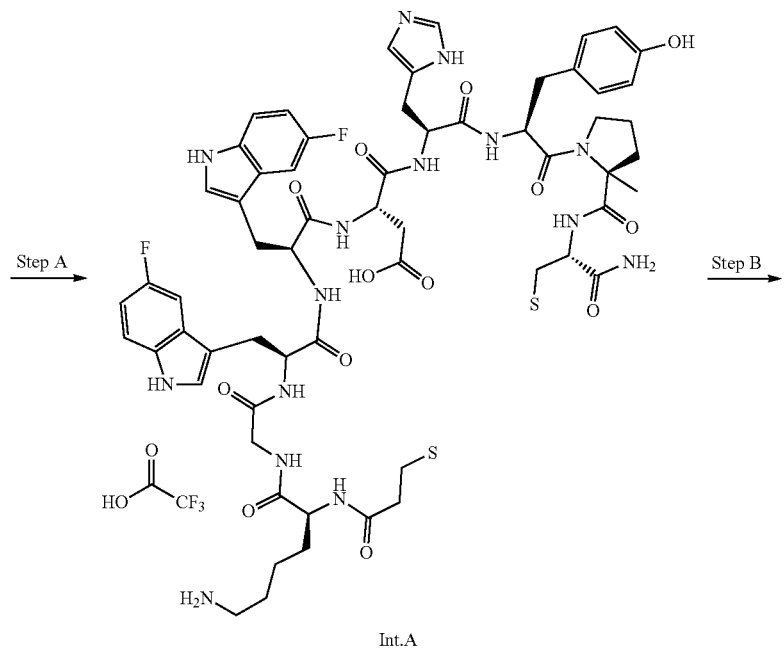
Int.A
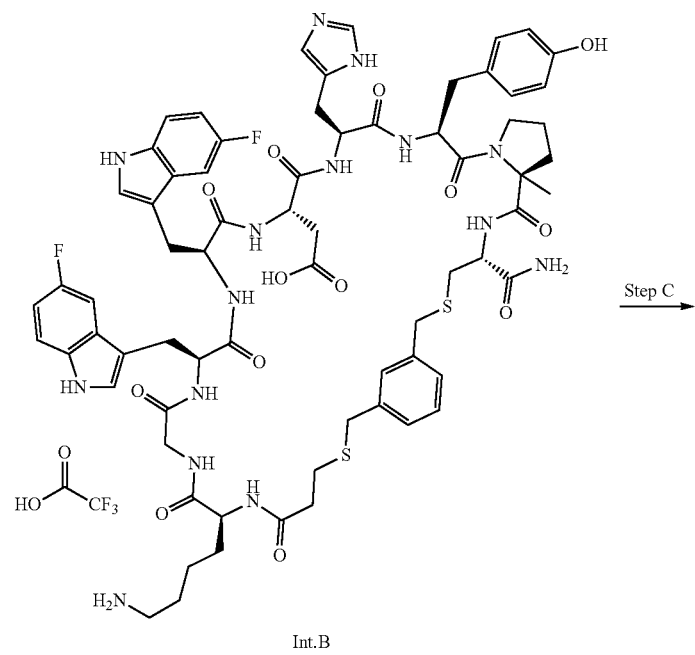
Int.B -continued

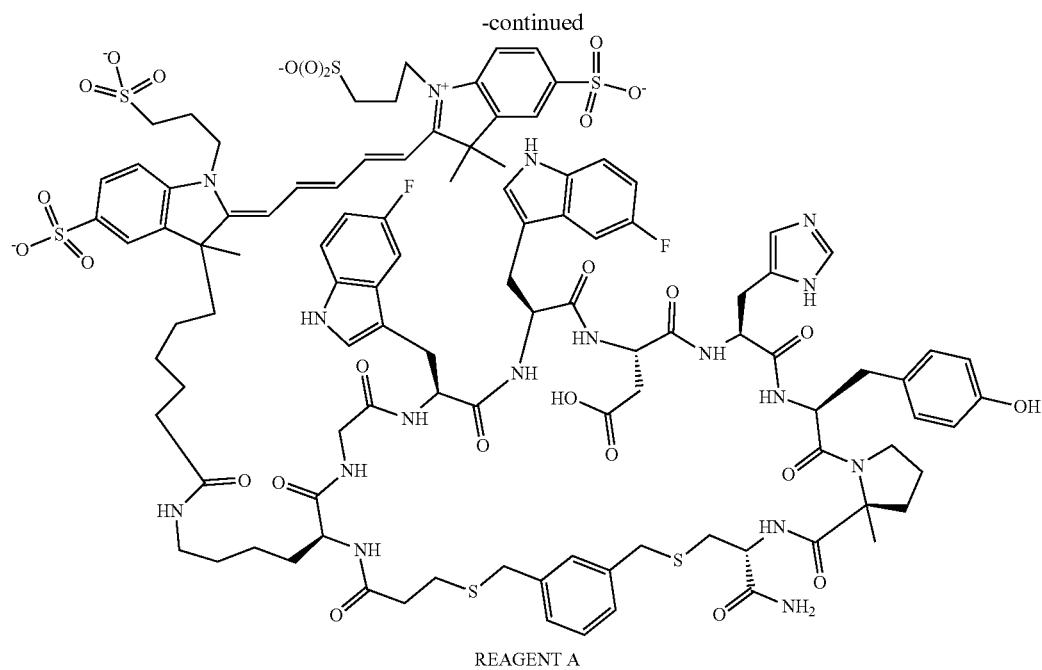

REAGENT A

Step A—Synthesis of Intermediate Compound t-A

The peptide was synthesized on a 0.250 mmol scale on CEM Liberty Blue, Microwave synthesizer using Fmoc/tBu chemistry on PS Rink-Amide MBHA resin, 0.32 mmol $g^{-1}$. The assembly was performed using single-couplings using 4 eq of Fmoc protected amino acid 0.2M in DMF, 4 eq of 0.5M HATU in DMF, 4 eq of 2M DIPEA (double coupling for Tyr). Fmoc deprotection cycles were performed using 20% (V/V) piperidine in DMF.

The sequence of Fmoc protected aminoacids and building blocks used are:
1. N-(((9H-fluoren-9-yl)methoxy)carbonyl)-S-trityl-L-cysteine
2. (S)-((((9H-fluoren-9-yl)methoxy)carbonyl)amino)-2-methylpyrrolidine-2-carboxylic acid
3. (((9H-fluoren-9-yl)methoxy)carbonyl)-L-tyrosine
4. N-(((9H-fluoren-9-yl)methoxy)carbonyl)-N-trityl-L-histidine
5. (S)-2-((((9H-fluoren-9-yl)methoxy)carbonyl)amino)-4-(tert-butoxy)-4-oxobutanoic acid
6. (S)-2-((((9H-fluoren-9-yl)methoxy)carbonyl)amino)-3-(5-fluoro-1H-indol-3-yl)propanoic acid
7. (S)-2-((((9H-fluoren-9-yl)methoxy)carbonyl)amino)-3-(5-fluoro-1H-indol-3-yl)propanoic acid
8. (((9H-fluoren-9-yl)methoxy)carbonyl)glycine
9. $N^2$-(((9H-fluoren-9-yl)methoxy)carbonyl)-$N^6$-(tert-butoxycarbonyl)-L-lysine
10. 3-(tritylthio)propanoic acid At the end of the assembly, the resin was washed with DMF, MeOH, DCM, Et20. The peptide was cleaved from solid support using 50 ml of TFA solution (v/v) (91% TFA, 5% $H_2O$, 4% TIPS) for approximately 1.5 hours, at room temperature. The resin was filtered, washed with TFA and solution concentrated to dryness and lyophilized. Lyophilization afforded Intermediate Compound Int. A (399 mg), which was used as crude in the next step. LCMS anal. calcd. C61H75F2N15O13S2: 1328.48, found: 1328.2 $(M+1)^+$ Step B—Synthesis of Intermediate Compound Int-B: As Described for Reagent B Purified by RP-HPLC (Waters Deltapak C4, double cartidge, 40×100 mm, 15 □m, 300 A; 15% to 35% ACN/water+0.1% TFA modifier over 20 min). Collected fractions lyophilized to afford 35 mg of Intermediate Compound Int-B. LCMS anal. calcd. for C69H81F2N15O13S2: 1430.62; found: 1430.9 (M+1)+.

Step C—Synthesis of Compound Reagent A: As Described for Reagent B

LCMS anal. calcd. for $C105H122F2N17O26S6^{3-}$: 2268.58; 1135.8 $(M+2)^{2+}$

Alexa FRET Plus TR-FRET

The PCSK9 Alexa FRET Plus assay measures the interaction between PCSK9 and an AlexaFluor647 (AF) tagged cyclic peptide, Reagent B ($K_D$=35 nM). A solution containing 1 nM biotinylated PCSK9+2.5 nM Lance Streptavidin Europium (Strep-Eu) is made in 50 mM HEPES pH 7.4, 0.15 M NaCl, 5 mM $CaCl_2$, 0.01% BSA, and 0.01% Surfactant P20. A separate solution containing 1920 nM of the AlexaFluor tagged cyclic peptide is made in the same buffer system. An Echo is used to transfer 0.075 ul of compound plus 0.675 ul of DMSO to each well of an assay plate followed by the addition of 15 ul of PCSK9+Stept-Eu and 15 ul of AF peptide. The final assay volume is 30.750 ul containing 0.5 nM PCSK9, 1.25 nM Strep-Eu, and 960 nM AF cyclic peptide. The reaction is incubated at room temperature for at least two hours prior to fluorescence measurements using an Envision Multilabel Reader. IC50 values are determined by fitting data to a sigmoidal dose-response curve using nonlinear regression. Ki is then calculated from the IC50 and the $K_D$ of AF cyclic peptide. Counts (B-counts) of the europium-labeled PCSK9 are followed to observe if compounds are adversely affecting PCSK9. A fall off of the B-counts is likely indicates a false positive of inhibition. Data from this procedure is reported as "P='numerical value' (nanomolar)"

Reagent B was prepared by the following procedure.
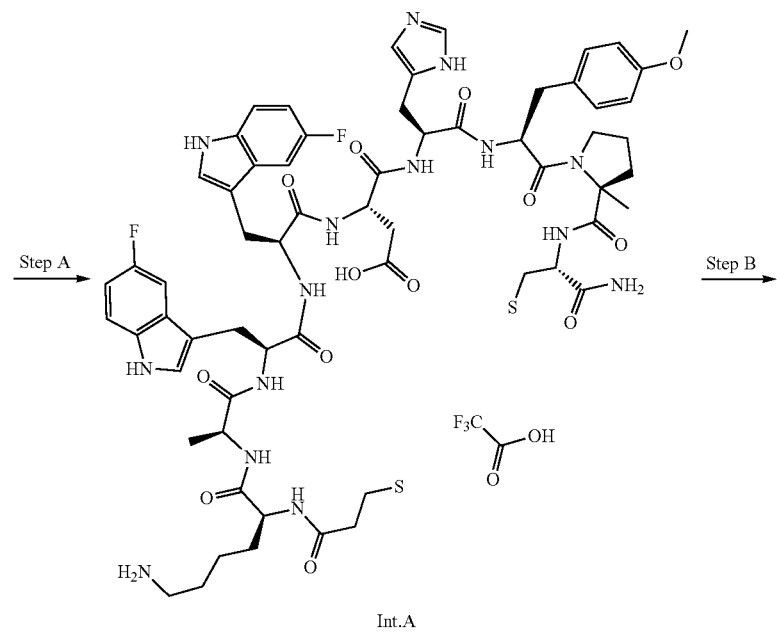
Int.A
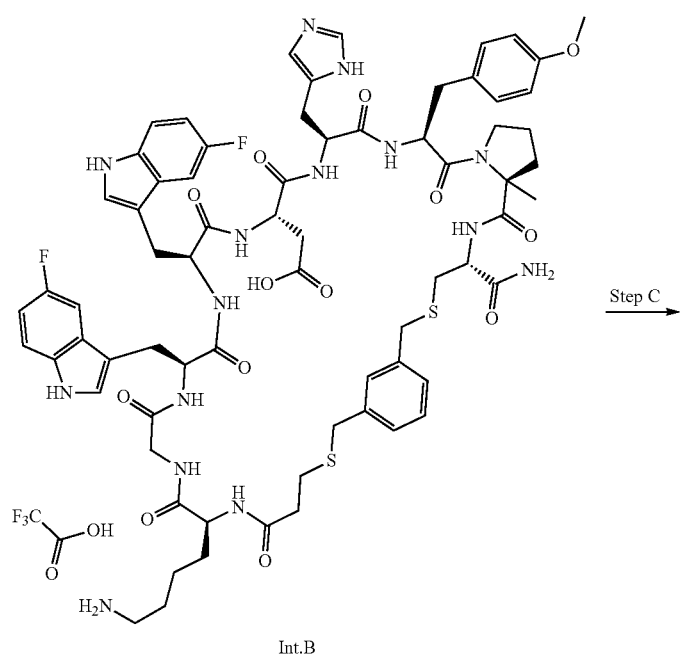
Int.B -continued

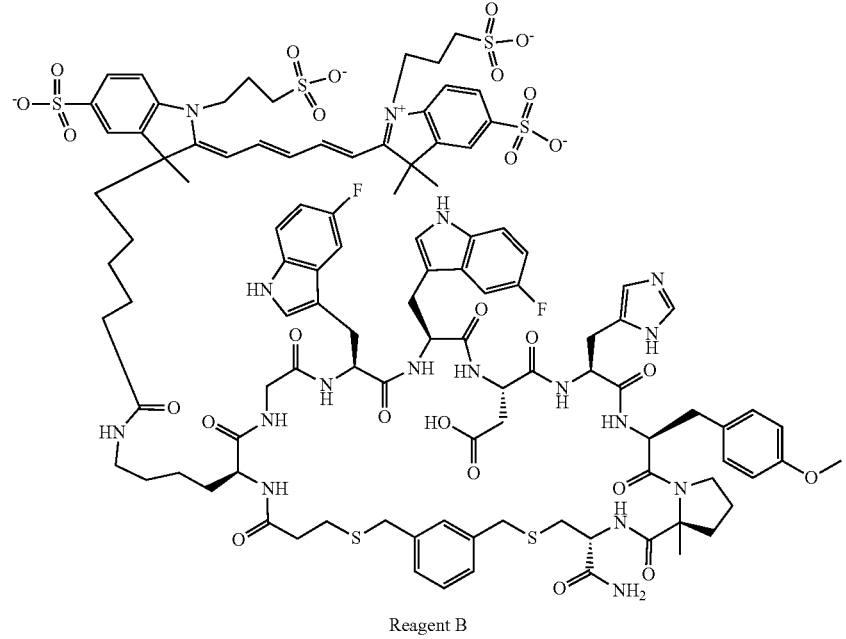

Reagent B

Step A—Synthesis of Intermediate Compound Int-A

The peptide was synthesized on a 0.250 mmol scale on CEM Liberty Blue, Microwave synthesizer using Fmoc/tBu chemistry on PS Rink-Amide MBHA resin, 0.32 mmol g$^{-1}$. The assembly was performed using single-couplings using 4 eq of Fmoc protected amino acid 0.2M in DMF, 4 eq of 1M Oxyme in DMF, 4 eq of 0.5M N,N-diisopropylcarbodiimide (DIC) (double coupling for Y01). Fmoc deprotection cycles were performed using 20% (V/V) piperidine in DMF.

The sequence of Fmoc protected amino acids and building blocks used are:
1. N-(((9H-fluoren-9-yl)methoxy)carbonyl)-S-trityl-L-cysteine
2. (S)-1((((9H-fluoren-9-yl)methoxy)carbonyl)amino)-2-methylpyrrolidine-2-carboxylic acid
3. (S)-2-((((9H-fluoren-9-yl)methoxy)carbonyl)amino)-3-(4-methoxyphenyl)propanoic acid
4. N-(((9H-fluoren-9-yl)methoxy)carbonyl)-N-trityl-L-histidine
5. (S)-2-((((9H-fluoren-9-yl)methoxy)carbonyl)amino)-4-(tert-butoxy)-4-oxobutanoic acid
6. (S)-2-((((9H-fluoren-9-yl)methoxy)carbonyl)amino)-3-(5-fluoro-1H-indol-3-yl)propanoic acid
7. (S)-2-((((9H-fluoren-9-yl)methoxy)carbonyl)amino)-3-(5-fluoro-1H-indol-3-yl)propanoic acid
8. (((9H-fluoren-9-yl)methoxy)carbonyl)-D-alanine
9. N$^2$-(((9H-fluoren-9-yl)methoxy)carbonyl)-N$^6$-(tert-butoxycarbonyl)-L-lysine
10. 3-(tritylthio)propanoic acid At the end of the assembly, the resin was washed with DMF, MeOH, DCM, Et20. The peptide was cleaved from solid support using 50 ml of TFA solution (v/v) (91% TFA, 5% H$_2$O, 4% TIPS) for approximately 1.5 hours, at room temperature. The resin was filtered, washed with TFA and solution concentrated to dryness and lyophilized. Lyophilization afforded Intermediate Compound Int. A (300 mg), which was used as crude in the next step. LCMS anal. calcd. C63H79F2N15O13S2: 1356.53, found: 1356.9 (M+1)$^+$.

Step B—Synthesis of Intermediate Compound Int-B

Crude Int-A (0.22 mmol) was redissolved in 24 ml of DMF. 6 ml of 1M aqueous solution of sodium bicarbonate was added to raise the pH to 7. Then 0.26 mmol of 1,3-bis(bromomethyl)benzene (0.1M in DMF) were added dropwise. Reaction was left under stirring at room temperature for 20 min, quenched with TFA (pH to 3-4) and then concentrated in vacuo to provide crude Int-B, which was purified by RP-HPLC (Waters XBridge, C18, 50×150 mm, 5 μm, 130 A; 25% to 40% ACN/water+0.1% TFA modifier over 20 min). Collected fractions were lyophilized to afford 35 mg of Intermediate Compound Int-B. LCMS anal. calcd. for C71H85F2N15O13S2: 1458.67; found: 1458.8 (M+1)$^+$.

Step C—Synthesis of Compound Reagent B

Intermediate Compound Int-B (15 mg) was dissolved in 0.2 ml of dry DMSO. Then 15 mg of ALEXAFLUOR 647NHS Ester (A37566, Life technology) dissolved in 1.5 ml of dry DMSO were added. 20 uL of dry DIPEA were added. Reaction was left under stirring at room temperature for 12 h under Nitrogen atmosphere in the dark. Quenched with TFA (pH to 3-4) and purified by RP-HPLC (Dr Maish, Reprosil Gold C18, 250×20 mm, 120 Å, 10 μm; 20% to 35% of 0.1% TFA in ACN/0.1% TFA in H$_2$O, over 20 min, then 35% to 40% over 5 min at 20 mL/min flow rate). Collected fractions were lyophilized to afford 16.1 mg of Compound Reagent B. LCMS anal. for C107H126F2N17O26S6$^{3-}$: 2296.64; found: 1150.6 (M+2)$^{2+}$ Activity data obtained by one or both of the above-described procedures is reported for selected example compounds of the invention in the following format: Example No.: A (standard TR Fret)='numerical value'; P (Alexa Fret plus standard TR Fret)='numerical value'/, note that all values reported are nanomolar.

The following compounds were assessed using the protocol described above with the results shown:

Ex-B01: A=2.04; Plus=1.24/Ex-B02: A=4.02; Plus=2.19/ Ex-B03: A<1.26; Plus=0.008/Ex-B04: A<1.26; Plus=0.020/Ex-C01: A=27.8/Ex-C02: A=150.9/Ex-C03: A=18.4/Ex-C04: A=4.24/Ex-C05: A<1.26; Plus=4.37/Ex-C06: A=15.9/Ex-C07: A=7.17/Ex-OT-03: A<1.26; Plus=0.32/Ex-OT-04: A<1.26; Plus=0.32/ Ex-OT-05: A<1.26; Plus=0.19/Ex-OT-06: A<1.26; Plus=0.29/

What is claimed is:

1. A compound of the Formula I:

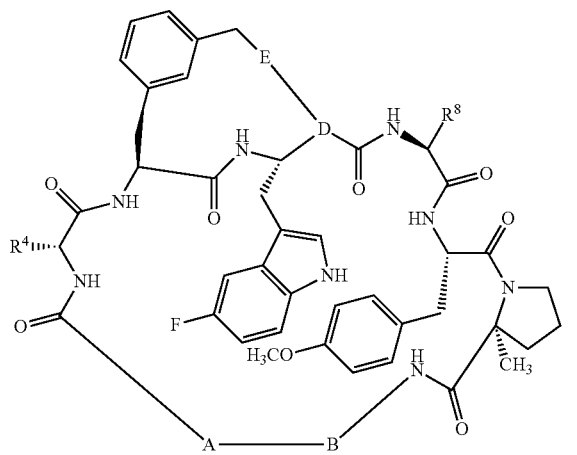

Formula I wherein:

R⁴ is: (a) linear, branched or cyclic alkyl of up to 6 carbon atoms; (b) —(CH₂)$_x$—R$^{13B}$, wherein: x is 1-4, and R$^{13B}$ is —NH₂ or —N⁺H₃; (c) —(CH₂)$_x$—R$^{13C}$, wherein: x is 1-4, and R$^{13C}$ is —N(R$^{13D}$)₂ or —N(R$^{13D}$)₃ wherein R$^{13D}$ is a linear or branched alkyl of up to 4 carbon atoms; (d) —CH₂NH—C(O)—O—C(CH₃)₃; or (e) —CH₂—NH—C(O)—[(CH₂)₂—O—]$_y$—(CH₂)₂—R$^{13E}$, wherein, y is 1 to 4 and R$^{13E}$ is —NH₂, —N⁺H₃, or —N⁺(CH₃)₃;

R⁸ is a moiety of the formula:

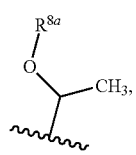

wherein R$^{8a}$ is —H, or a linear, branched or cyclic alkyl of up to four carbon atoms;

A is (a) —CH₂—; or
(b) a moiety of the formula:

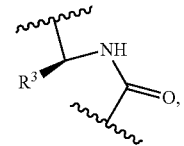

wherein R³ is:
(i) linear, branched or cyclic alkyl of up to 6 carbon atoms;
(ii) —(CH₂)$_z$—R$^{14A}$, wherein: z is 1-4, and R$^{14A}$ is —NH₂ or —N⁺H₃;
(iii) —(CH₂)$_z$—R$^{14B}$, wherein: z is 1-4, and R$^{14B}$ is —N(CH₃)₂ or —N⁺(CH₃)₃; or
(iv) —CH₂—NH—C(O)—[(CH₂)$_y$—O—]₂—(CH₂)₂—R$^{14C}$ wherein, y' is 1 to 6, and R$^{14C}$ is —NH₂, —N⁺H₃, or —N⁺(CH₃)₃;

B is:
(a) a moiety of the formula:

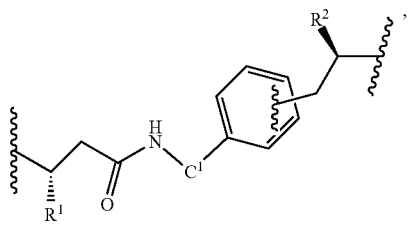

wherein:
R¹ is —H or —NH—C(O)—CH₃;
R² is —H or —C(O)—R$^{15A}$, wherein R$^{15A}$ is —NH₂, —N⁺H₃, or —N⁺(CH₃)₃; and
C¹ is —CH₂— or —(CH₂)₂—O—; or
(b) a moiety of the formula:

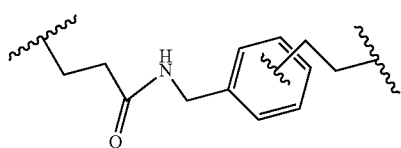

D is:
(a) a moiety of the formula:

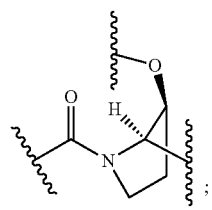

or (b) a moiety of the formula:

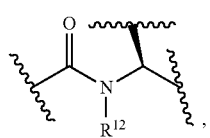

wherein $R^{12}$ is —H or —CH$_3$; and

E is:

(a) a moiety of the formula:

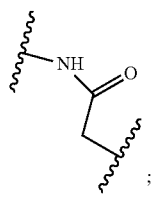 [SMILES: *CC(=O)N*]

or (b) a moiety of the formula:

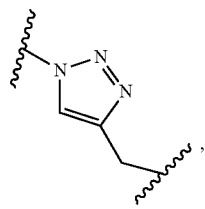 [SMILES: *Cc1cn(*)nn1]

or a pharmaceutically acceptable salt thereof.

2. A compound of claim 1 having the formula of Formula II:

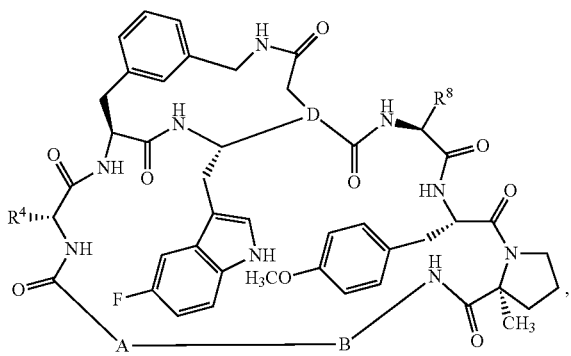

Formula II or a pharmaceutically acceptable salt thereof.

3. A compound of claim 2, or a pharmaceutically acceptable salt thereof, wherein $R^4$ is:

(a) —CH$_3$;

(b) —CH(CH$_3$)$_2$;

(c) —(CH$_2$)$_x$—R$^{13b}$, wherein: x is 1-4, and R$^{13b}$ is —NH$_2$ or —N$^+$H$_3$; (d) —CH$_2$NH—C(O)—O—C(CH$_3$)$_3$; or (iv) —CH$_2$—NH—C(O)—[(CH$_2$)$_2$—O—]$_2$—(CH$_2$)$_2$—R$^{13}$, wherein R$^{13c}$ is —NH$_2$, —N$^+$H$_3$, or —N$^+$(CH$_3$)$_3$.

4. A compound of claim 2, or a pharmaceutically acceptable salt thereof, wherein R$^8$ is a moiety of the formula:

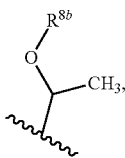

wherein $R^{8b}$ is —H, —CH$_3$, or —C(CH$_3$)$_3$.

5. A compound of claim 2, or a pharmaceutically acceptable salt thereof,

Wherein:

A is a moiety of the formula:

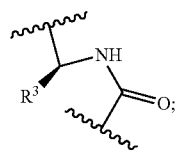

and $R^3$ is (i) —CH$_3$;

(ii) —CH(CH$_3$)$_2$;

(iii) —(CH$_2$)$_z$—R$^{13a}$, wherein: z is 1-4, and R$^{13a}$ is —NH$_2$ or —N$^+$H$_3$; or (iv) —CH$_2$—NH—C(O)—[(CH$_2$)$_2$—O—]$_2$—(CH$_2$)$_2$—R$^{13c}$, wherein R$^{13c}$ is —NH$_2$, —N$^+$H$_3$, or —N$^+$(CH$_3$)$_3$.

6. A compound of claim 2 having the formula of Formula III:

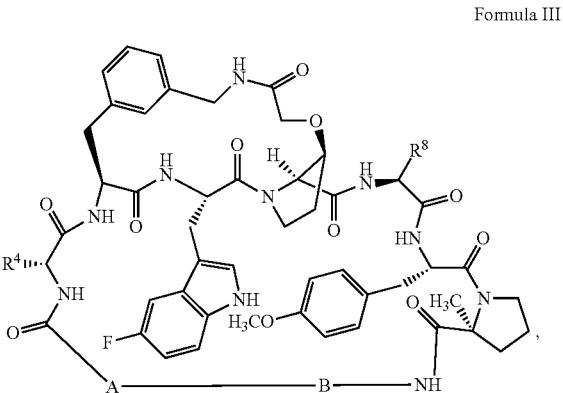

Formula III or a pharmaceutically acceptable salt thereof.

7. A compound of claim 1 having the Formula IV:
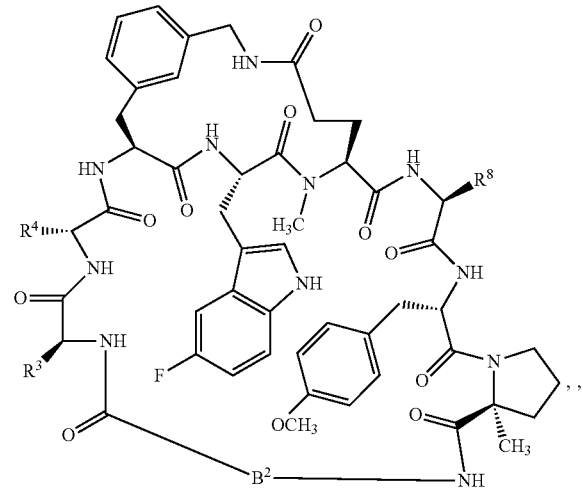
Formula IV
wherein:
B² is:
(a) a moiety of the formula:
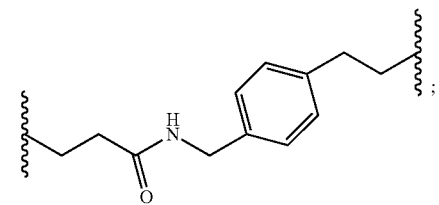 [SMILES: *CCC(=O)NCc1ccc(CC*)cc1]
or
(b) a moiety of the formula:
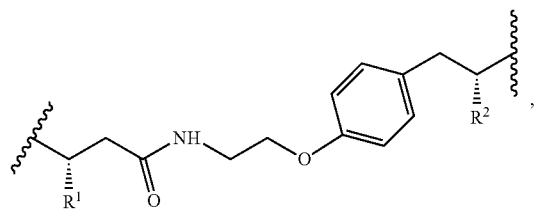
wherein:
R¹ is —H or —NH—C(O)—CH₃;
R² is —H or —C(O)—R$^{16A}$ NH₂ R$^{16A}$ is —NH₂, —N⁺H₃, —N(CH₃)₂, or —N⁺(CH₃)₃,
or a pharmaceutically acceptable salt thereof.
8. A compound of claim 1, which is selected from the group consisting of:
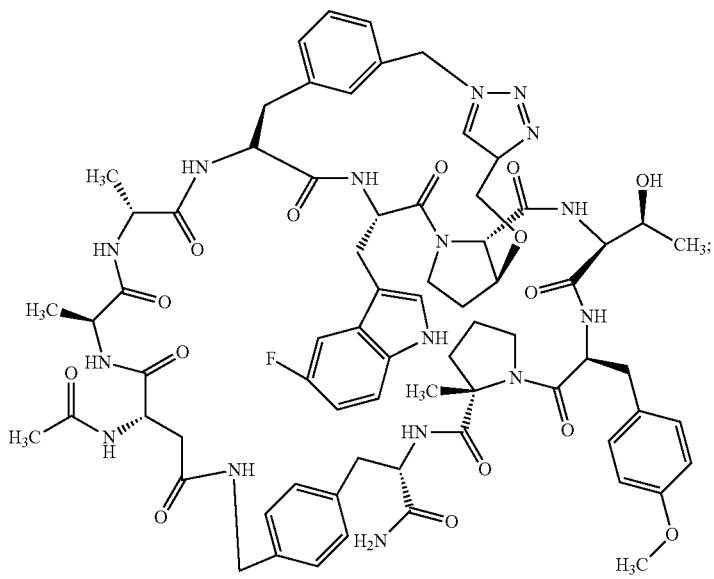

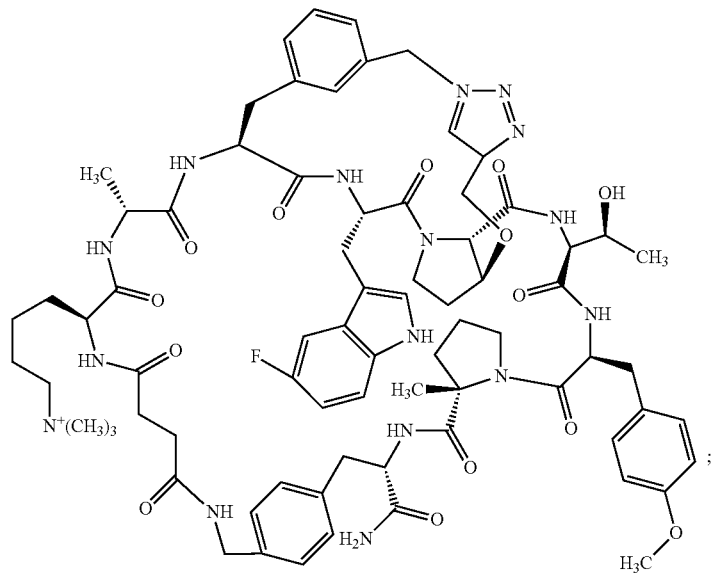
;
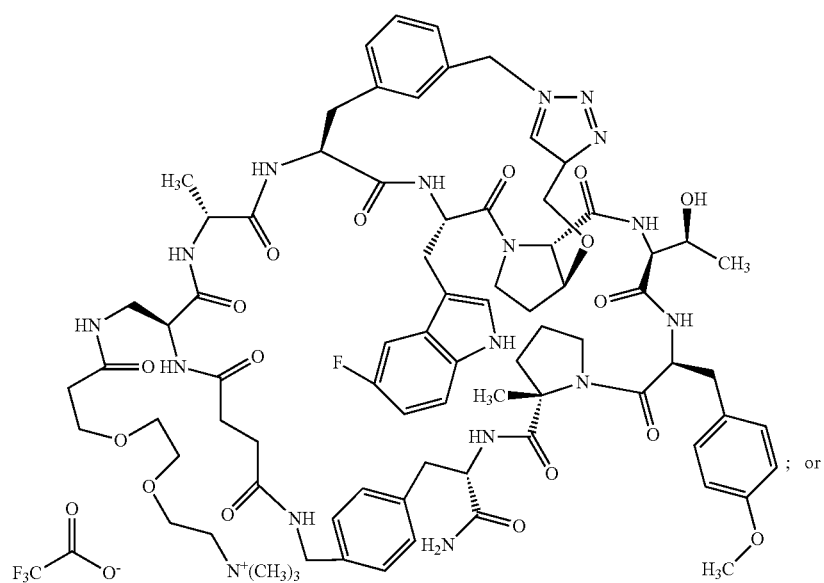
; or

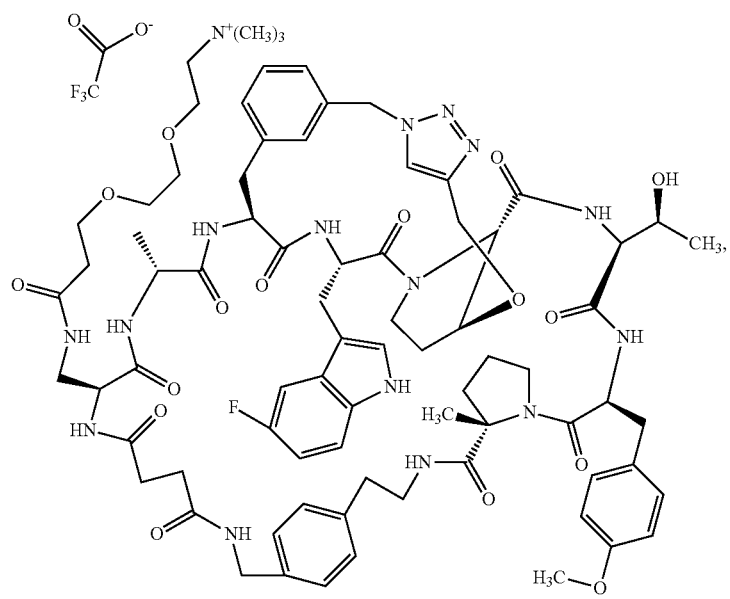
or a pharmaceutically acceptable salt thereof.
9. A compound of claim 1, which is selected from the group consisting of
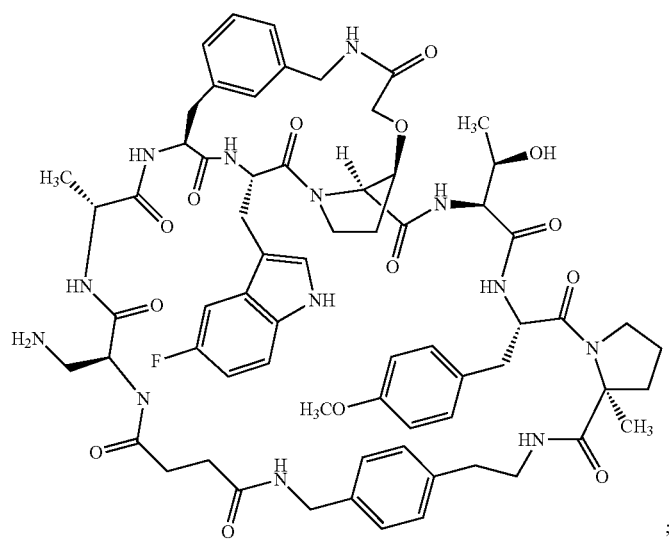
;

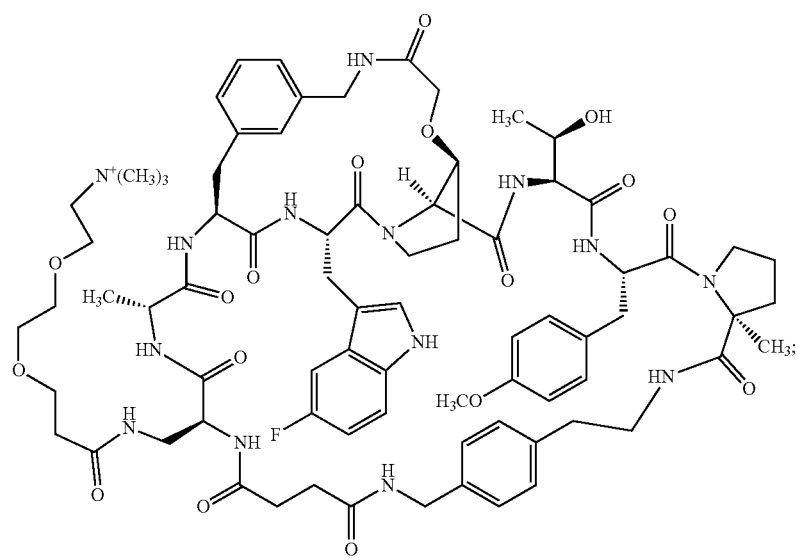
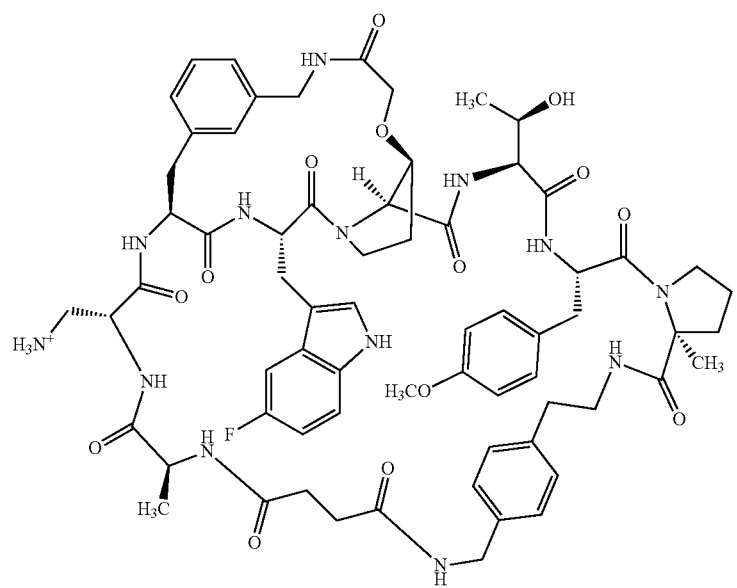
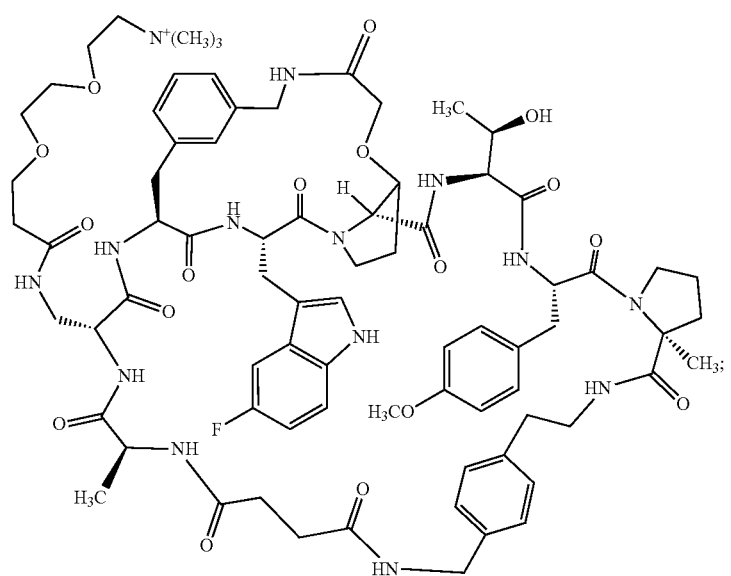

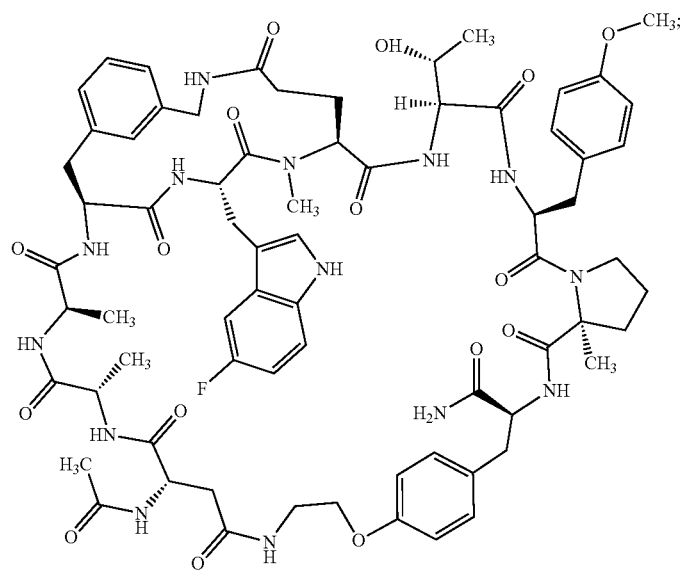
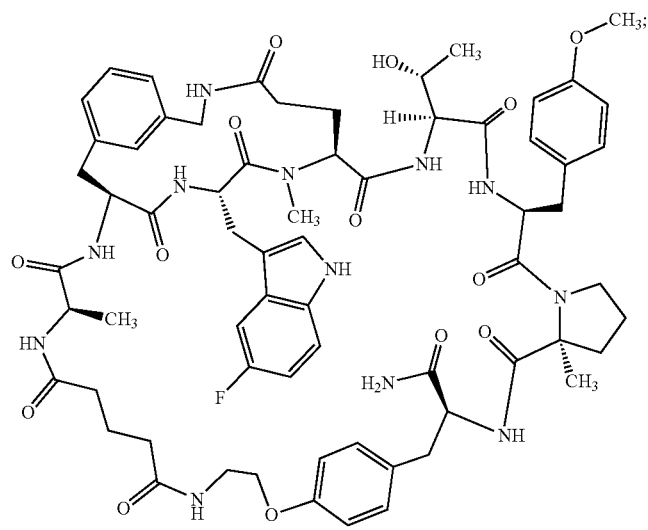
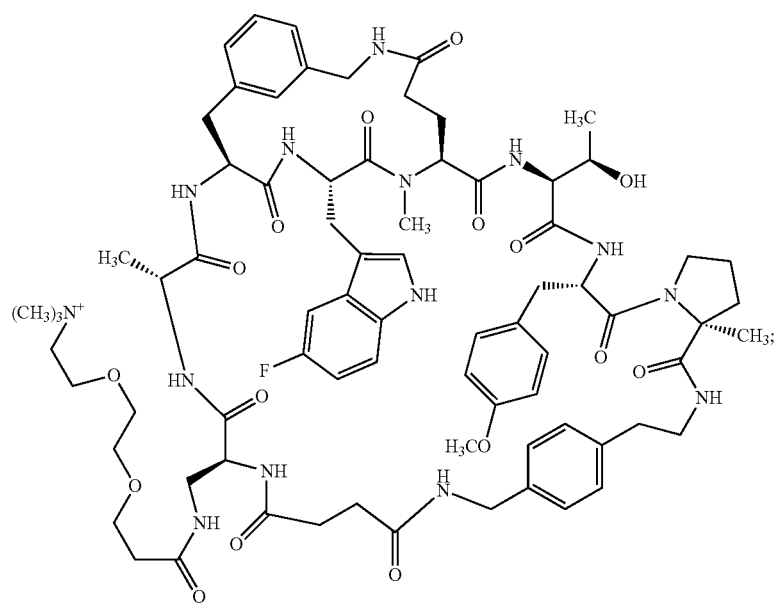

-continued
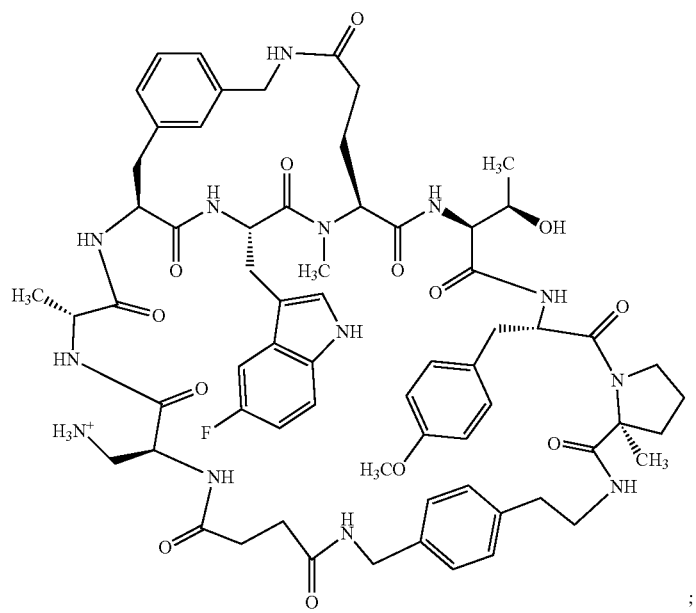
;
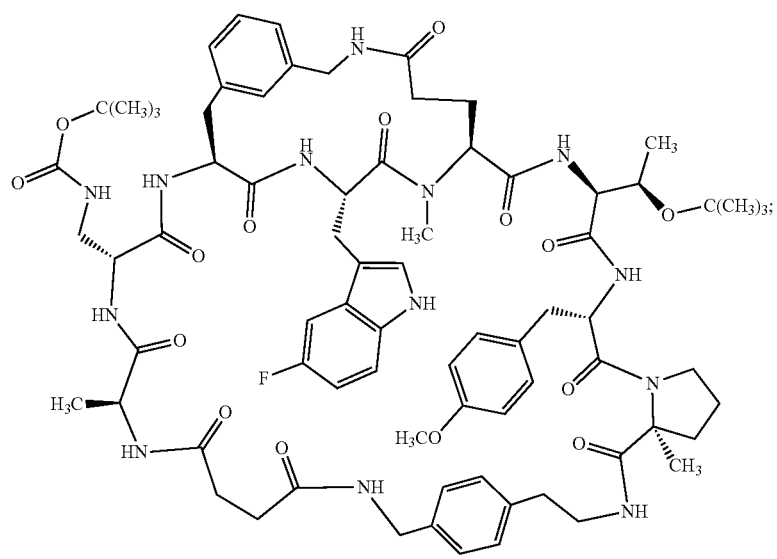
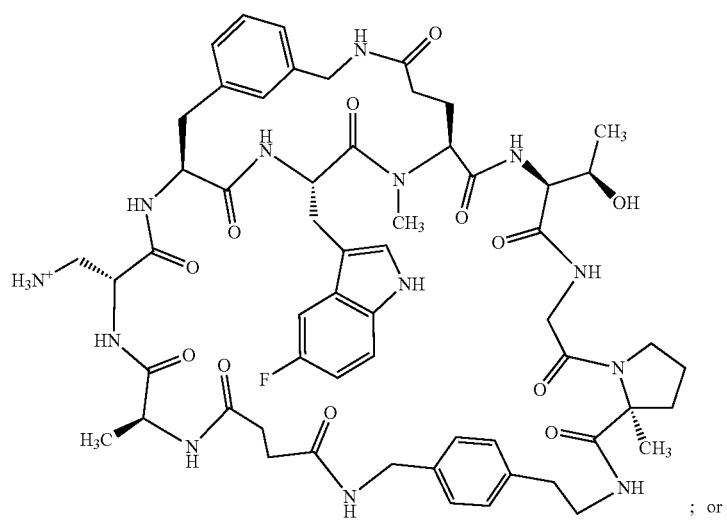
; or

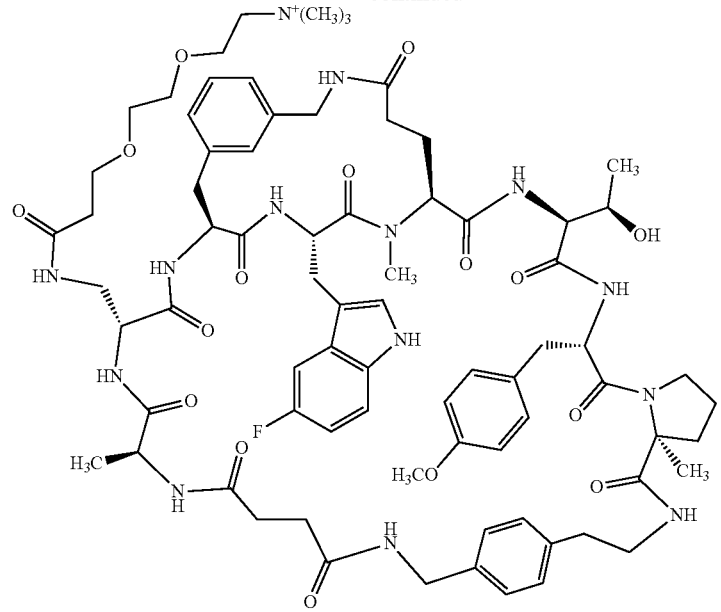

or a pharmaceutically acceptable salt thereof.

10. A composition comprising at least one compound of claim 1, or a pharmaceutically acceptable salt thereof, and at least one pharmaceutically acceptable excipient.

11. A method of treating hypercholesterolemia, comprising administering to a patient in need thereof a therapeutically effective amount of a composition of claim 10.

12. A method of treating hypercholesterolemia, comprising administering to a patient in need thereof a therapeutically effective amount of a compound of claim 1.

13. A compound according to claim 1, or a pharmaceutically acceptable salt thereof, for use in therapy.

14. A compound according to claim 1, or a pharmaceutically acceptable salt thereof, for treating hypercholesterolemia.

15. A compound of claim 1, wherein the compound is

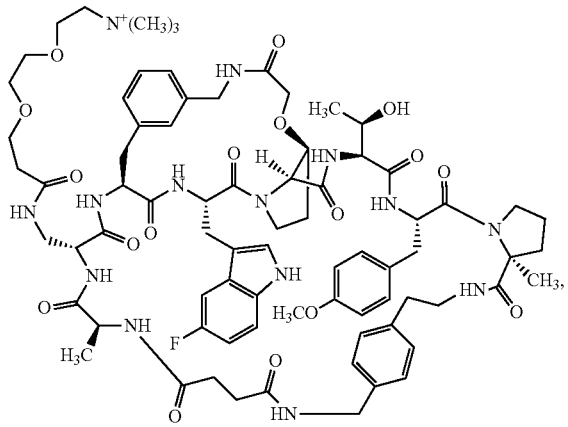

or a pharmaceutically acceptable salt thereof.

* * * * *